US011219525B2

(12) United States Patent
Vesely et al.

(10) Patent No.: US 11,219,525 B2
(45) Date of Patent: Jan. 11, 2022

(54) APPARATUS AND METHODS FOR TREATING A DEFECTIVE CARDIAC VALVE

(71) Applicant: CroiValve Ltd., Dublin (IE)

(72) Inventors: Ivan Vesely, Gaithersburg, MD (US); Conor Quinn, Malahide (IE); Aoife Mulligan, Sandymount (IE); Paul Heneghan, Raheny (IE); Patrick Quinn, Howth (IE); Stephen O'Sullivan, Clontarf (IE)

(73) Assignee: CroiValve Ltd., Dublin (IE)

( * ) Notice: Subject to any disclaimer, the term of this patent is extended or adjusted under 35 U.S.C. 154(b) by 0 days.

(21) Appl. No.: 17/107,565

(22) Filed: Nov. 30, 2020

(65) Prior Publication Data

US 2021/0077257 A1 Mar. 18, 2021

Related U.S. Application Data

(63) Continuation of application No. PCT/IB2020/057368, filed on Aug. 4, 2020.
(Continued)

(51) Int. Cl.
*A61F 2/24* (2006.01)

(52) U.S. Cl.
CPC ............ *A61F 2/2466* (2013.01); *A61F 2/243* (2013.01); *A61F 2/2418* (2013.01);
(Continued)

(58) Field of Classification Search
CPC ...... A61F 2/2427; A61F 2/243; A61F 2/2439; A61F 2/2466
See application file for complete search history.

(56) References Cited

U.S. PATENT DOCUMENTS

| 2,684,069 A | 7/1954 | Shearman et al. |
| 3,689,942 A | 9/1972 | Rapp |

(Continued)

FOREIGN PATENT DOCUMENTS

| AU | 2016200392 B2 | 12/2017 |
| CA | 2705942 A1 | 5/2009 |

(Continued)

OTHER PUBLICATIONS

Berger et al., Comparison of results and complications of surgical and Amplatzer device closure of atrial septal defects, J. Thorac. Cardiovasc. Surg., 118(4):674-8 (1999).
(Continued)

*Primary Examiner* — William H Matthews
(74) *Attorney, Agent, or Firm* — Eversheds Sutherland (US) LLP; Christopher C. Bolten; Albert K. Heng

(57) ABSTRACT

Apparatus and methods for repairing a cardiac valve, e.g., a tricuspid valve, are provided. The apparatus may include a prosthetic device coupled to an elongated support to suspend and maintain the prosthetic device within the cardiac valve. The support may include a proximal elongated shaft detachably coupled, in a delivery state, to a distal elongated shaft coupled to the prosthetic device. The proximal elongated shaft may detach from the distal elongated shaft at a detachment area within the patient responsive to actuation and components of the distal elongated shaft may lock to implant the prosthetic device and the distal elongated shaft within the patient. The prosthetic device may be formed of biocompatible material coupled to a frame, and may have prosthetic leaflets that allows blood to flow through in one direction during a phase of the cardiac cycle (e.g., diastole) but prevent blood regurgitation during the other phase (e.g., systole).

30 Claims, 47 Drawing Sheets

Related U.S. Application Data

(60) Provisional application No. 62/882,961, filed on Aug. 5, 2019.

(52) U.S. Cl.
CPC .......... *A61F 2/2427* (2013.01); *A61F 2/2439* (2013.01); *A61F 2220/0016* (2013.01)

(56) References Cited

U.S. PATENT DOCUMENTS

| | | |
|---|---|---|
| 3,746,003 A | 7/1973 | Blake et al. |
| 5,509,428 A | 4/1996 | Dunlop |
| 5,792,179 A | 8/1998 | Sideris |
| 6,168,614 B1 | 1/2001 | Andersen et al. |
| 6,332,893 B1 | 12/2001 | Mortier et al. |
| 6,461,366 B1 | 10/2002 | Seguin |
| 6,527,800 B1 | 3/2003 | McGuckin, Jr. et al. |
| 6,540,782 B1 | 4/2003 | Snyders |
| 6,582,462 B1 | 6/2003 | Andersen et al. |
| 6,629,534 B1 | 10/2003 | St. Goar et al. |
| 6,752,813 B2 | 6/2004 | Goldfarb et al. |
| 6,764,510 B2 | 7/2004 | Vidlund et al. |
| 6,821,297 B2 | 11/2004 | Snyders |
| 6,893,459 B1 | 5/2005 | MacOviak |
| 6,955,689 B2 | 10/2005 | Ryan et al. |
| 7,077,862 B2 | 7/2006 | Vidlund et al. |
| 7,678,145 B2 | 3/2010 | Vidlund et al. |
| 7,704,277 B2 | 4/2010 | Zakay et al. |
| 7,785,366 B2 | 8/2010 | Maurer et al. |
| 7,854,762 B2 | 12/2010 | Speziali et al. |
| 7,901,454 B2 | 3/2011 | Kapadia et al. |
| 8,070,805 B2 | 12/2011 | Vidlund et al. |
| 8,216,303 B2 | 7/2012 | Navia |
| 8,449,606 B2 | 5/2013 | Eliasen et al. |
| 8,460,370 B2 | 6/2013 | Zakay et al. |
| 8,470,028 B2 | 6/2013 | Thornton et al. |
| 8,475,525 B2 | 7/2013 | Maisano et al. |
| 8,480,730 B2 | 7/2013 | Maurer et al. |
| 8,486,136 B2 | 7/2013 | Maurer et al. |
| 8,506,624 B2 | 8/2013 | Vidlund et al. |
| 8,579,967 B2 | 11/2013 | Webler et al. |
| 8,758,432 B2 | 6/2014 | Solem |
| 8,888,844 B2 | 11/2014 | Eliasen et al. |
| 8,894,705 B2 | 11/2014 | Eliasen et al. |
| 8,923,973 B2 | 12/2014 | Gross |
| 8,932,348 B2 | 1/2015 | Solem et al. |
| 8,961,596 B2 | 2/2015 | Maisano et al. |
| 8,968,395 B2 | 3/2015 | Hauser et al. |
| 8,979,922 B2 | 3/2015 | Jayasinghe et al. |
| 8,992,605 B2 | 3/2015 | Zakai et al. |
| 9,005,279 B2 | 4/2015 | Gabbay |
| 9,011,523 B2 | 4/2015 | Seguin |
| 9,132,007 B2 | 9/2015 | Menk et al. |
| 9,161,837 B2 | 10/2015 | Kapadia |
| 9,232,998 B2 | 1/2016 | Wilson et al. |
| 9,232,999 B2 | 1/2016 | Maurer et al. |
| 9,289,297 B2 | 3/2016 | Wilson et al. |
| 9,358,112 B2 | 6/2016 | Hlavka et al. |
| 9,370,424 B2 | 6/2016 | Call et al. |
| 9,414,918 B2 | 8/2016 | Chau et al. |
| 9,474,605 B2 | 10/2016 | Rowe et al. |
| 9,498,330 B2 | 11/2016 | Solem |
| 9,510,946 B2 | 12/2016 | Chau et al. |
| 9,545,305 B2 | 1/2017 | Wilson et al. |
| 9,579,199 B2 | 2/2017 | Hauser et al. |
| 9,629,720 B2 | 4/2017 | Nguyen et al. |
| 9,636,223 B2 | 5/2017 | Khalil et al. |
| 9,763,781 B2 | 9/2017 | Kramer |
| 9,763,782 B2 | 9/2017 | Solem |
| 9,827,101 B2 | 11/2017 | Solem et al. |
| 10,383,729 B2 | 8/2019 | Quinn |
| 10,682,231 B2 | 6/2020 | Quinn |
| 2002/0103532 A1 | 8/2002 | Langberg et al. |
| 2003/0105520 A1 | 6/2003 | Alferness et al. |
| 2004/0059351 A1 | 3/2004 | Eigler et al. |
| 2004/0127981 A1 | 7/2004 | Rahdert et al. |
| 2004/0138744 A1 | 7/2004 | Lashinski et al. |
| 2004/0153146 A1 | 8/2004 | Lashinski et al. |
| 2004/0210307 A1 | 10/2004 | Khairkhahan |
| 2004/0225354 A1 | 11/2004 | Allen et al. |
| 2004/0243229 A1 | 12/2004 | Vidlund et al. |
| 2005/0033446 A1 | 2/2005 | Deem et al. |
| 2005/0075723 A1 | 4/2005 | Schroeder et al. |
| 2005/0107810 A1 | 5/2005 | Morales et al. |
| 2005/0107871 A1 | 5/2005 | Realyvasquez et al. |
| 2005/0187616 A1 | 8/2005 | Realyvasquez |
| 2005/0222488 A1 | 10/2005 | Chang et al. |
| 2005/0228495 A1 | 10/2005 | MacOviak |
| 2006/0058871 A1 | 3/2006 | Zakay et al. |
| 2006/0178700 A1 | 8/2006 | Quinn |
| 2006/0193899 A1 | 8/2006 | Sawhney |
| 2006/0241745 A1 | 10/2006 | Solem |
| 2007/0093890 A1 | 4/2007 | Eliasen et al. |
| 2007/0185571 A1 | 8/2007 | Kapadia et al. |
| 2007/0198082 A1 | 8/2007 | Kapadia et al. |
| 2007/0232992 A1 | 10/2007 | Kutsko et al. |
| 2007/0255399 A1 | 11/2007 | Eliasen et al. |
| 2007/0265700 A1 | 11/2007 | Eliasen et al. |
| 2008/0033541 A1 | 2/2008 | Gelbart et al. |
| 2008/0243245 A1 | 10/2008 | Thambar et al. |
| 2009/0076600 A1 | 3/2009 | Quinn |
| 2009/0149949 A1 | 6/2009 | Quinn |
| 2009/0240326 A1 | 9/2009 | Wilson et al. |
| 2010/0185276 A1 | 7/2010 | Vidlund et al. |
| 2010/0217382 A1 | 8/2010 | Chau et al. |
| 2010/0262233 A1 | 10/2010 | He |
| 2010/0298929 A1 | 11/2010 | Thornton et al. |
| 2010/0298930 A1 | 11/2010 | Orlov |
| 2011/0022164 A1 | 1/2011 | Quinn et al. |
| 2011/0060407 A1 | 3/2011 | Ketai et al. |
| 2011/0112632 A1 | 5/2011 | Chau et al. |
| 2011/0224784 A1 | 9/2011 | Quinn |
| 2011/0257721 A1 | 10/2011 | Tabor |
| 2012/0010700 A1 | 1/2012 | Spenser |
| 2013/0018459 A1 | 1/2013 | Maisano et al. |
| 2013/0090728 A1 | 4/2013 | Solem |
| 2013/0172978 A1 | 7/2013 | Vidlund et al. |
| 2013/0310928 A1 | 11/2013 | Morriss et al. |
| 2013/0325110 A1 | 12/2013 | Khalil et al. |
| 2013/0338763 A1 | 12/2013 | Rowe et al. |
| 2014/0031928 A1 | 1/2014 | Murphy et al. |
| 2014/0039615 A1 | 2/2014 | Padala et al. |
| 2014/0135910 A1 | 5/2014 | Hauser et al. |
| 2014/0200657 A1 | 7/2014 | Maurer et al. |
| 2014/0207230 A1 | 7/2014 | Wilson et al. |
| 2014/0243968 A1 | 8/2014 | Padala |
| 2014/0257347 A1 | 9/2014 | Eidenschink |
| 2014/0276395 A1 | 9/2014 | Wilson et al. |
| 2014/0276971 A1 | 9/2014 | Kovach |
| 2014/0336751 A1 | 11/2014 | Kramer |
| 2014/0350662 A1 | 11/2014 | Vaturi |
| 2014/0379075 A1 | 12/2014 | Maurer et al. |
| 2015/0073547 A1 | 3/2015 | Eliasen et al. |
| 2015/0112429 A1 | 4/2015 | Khairkhahan et al. |
| 2015/0127097 A1 | 5/2015 | Neumann et al. |
| 2015/0134050 A1 | 5/2015 | Solem et al. |
| 2015/0202043 A1 | 7/2015 | Zakai et al. |
| 2015/0223934 A1 | 8/2015 | Vidlund et al. |
| 2015/0257884 A1 | 9/2015 | Subramanian et al. |
| 2015/0305861 A1 | 10/2015 | Annest |
| 2016/0030166 A1 | 2/2016 | Kapadia |
| 2016/0074164 A1 | 3/2016 | Naor |
| 2016/0081798 A1 | 3/2016 | Kocaturk |
| 2016/0089233 A1 | 3/2016 | Lee et al. |
| 2016/0089239 A1 | 3/2016 | Hauser et al. |
| 2016/0113762 A1 | 4/2016 | Clague et al. |
| 2016/0166380 A1 | 6/2016 | Seguin et al. |
| 2016/0166382 A1 | 6/2016 | Nguyen |
| 2016/0184098 A1 | 6/2016 | Vaturi |
| 2016/0193043 A1 | 7/2016 | Kim |
| 2016/0199181 A1 | 7/2016 | Kramer |
| 2016/0242909 A1 | 8/2016 | Ketai et al. |
| 2016/0262741 A1 | 9/2016 | Gilmore et al. |
| 2016/0262886 A1 | 9/2016 | Wang |

(56) References Cited

U.S. PATENT DOCUMENTS

| | | |
|---|---|---|
| 2016/0278920 A1 | 9/2016 | Braido et al. |
| 2016/0287387 A1 | 10/2016 | Wei |
| 2017/0035561 A1 | 2/2017 | Rowe et al. |
| 2017/0196687 A1 | 7/2017 | Braido et al. |
| 2017/0209265 A1 | 7/2017 | Karapetian et al. |
| 2017/0224444 A1 | 8/2017 | Viecilli et al. |
| 2017/0239041 A1 | 8/2017 | Quinn |
| 2017/0266003 A1 | 9/2017 | Hammer et al. |
| 2018/0168803 A1* | 6/2018 | Pesce .................... A61F 2/2409 |
| 2019/0209297 A1 | 7/2019 | Metchik et al. |

FOREIGN PATENT DOCUMENTS

| | | |
|---|---|---|
| CA | 2729027 A1 | 12/2009 |
| CA | 2863939 A1 | 8/2012 |
| CA | 2842288 A1 | 1/2013 |
| CA | 2871156 A1 | 11/2013 |
| CA | 2872611 A1 | 11/2013 |
| CN | 102781371 A | 11/2012 |
| CN | 202821715 U | 3/2013 |
| CN | 104768500 B | 10/2017 |
| DE | 102013017750 A1 | 4/2015 |
| DE | 102013017993 A1 | 6/2015 |
| EP | 1796597 A2 | 6/2007 |
| EP | 2032078 A1 | 3/2009 |
| EP | 2032080 A2 | 3/2009 |
| EP | 2150206 A1 | 2/2010 |
| EP | 2849681 A1 | 3/2015 |
| EP | 1871300 B1 | 4/2016 |
| EP | 3023117 A1 | 5/2016 |
| EP | 3042615 A1 | 7/2016 |
| EP | 3056170 A1 | 8/2016 |
| EP | 2023858 B1 | 10/2016 |
| EP | 3081195 A1 | 10/2016 |
| EP | 2032080 B1 | 5/2017 |
| EP | 3187150 A1 | 7/2017 |
| EP | 3241525 A1 | 11/2017 |
| ES | 2586111 T3 | 10/2016 |
| JP | 2013517830 A | 5/2013 |
| JP | 2016512721 A | 5/2016 |
| JP | 2016512726 A | 5/2016 |
| JP | 2016521633 A | 7/2016 |
| RU | 2014153781 A | 7/2016 |
| WO | WO-0060995 A2 | 10/2000 |
| WO | WO-03059209 A2 | 7/2003 |
| WO | WO-2004112658 A1 | 12/2004 |
| WO | WO-2005087140 A1 | 9/2005 |
| WO | WO-2006064490 A1 | 6/2006 |
| WO | WO-2006102329 A1 | 9/2006 |
| WO | WO-2006111391 A1 | 10/2006 |
| WO | WO-2007016097 A2 | 2/2007 |
| WO | WO-2007050256 A2 | 5/2007 |
| WO | WO-2007078772 A1 | 7/2007 |
| WO | WO-2007144865 A1 | 12/2007 |
| WO | WO-2008141322 A1 | 11/2008 |
| WO | WO-2009053952 A2 | 4/2009 |
| WO | WO-2011034973 A3 | 5/2011 |
| WO | WO-2012035279 A1 | 3/2012 |
| WO | WO-2013016618 A2 | 1/2013 |
| WO | WO-2013028387 A2 | 2/2013 |
| WO | WO-2015123597 A1 | 8/2015 |
| WO | WO-2016000274 A1 | 1/2016 |
| WO | WO-2016050751 A1 | 4/2016 |
| WO | WO-2016059533 A1 | 4/2016 |
| WO | WO-2016079734 A1 | 5/2016 |
| WO | WO-2016130706 A1 | 8/2016 |
| WO | WO-2017079234 A1 | 5/2017 |
| WO | WO-2019154927 A1 | 8/2019 |

OTHER PUBLICATIONS

Campelo-Parada, et al., First-in-Man Experience of a Novel Transcatheter Repair System for Treating Severe Tricuspid Regurgitation, J. Am. Coll. Cardiol., 66(22):2475-83 (2015).

Espiritu, et al., Transcatheter Mitral Valve Repair Therapies: Evolution, Status and Challenges, Annals of Biomedical Engineering, 45(2):332-359 (2017).

Extended European Search Report dated Sep. 7, 2018 in EP Patent Application Serial No. 18165070.6.

International Search Report and Written Opinion dated Nov. 17, 2020 in Int'l PCT Patent Appl. Serial No. PCT/IB2020/057368.

International Search Report and Written Opinion dated Jul. 10, 2019 in Int'l PCT Patent Appl. Serial No. PCT/EP2019/053038.

International Search Report dated Dec. 1, 2015 in Intl PCT Patent Appl. Serial No. PCT/EP2015/072388.

Peppas, et al., Preclinical in vivo long-term evaluation of the novel Mitra-Spacer technology: experimental validation in the ovine model, EuroIntervention, 13(3):272-279 (2017).

U.S. Appl. No. 15/514,204, filed Mar. 24, 2017 / Aug. 20, 2019.
U.S. Appl. No. 16/443,792, filed Jun. 17, 2019 / Jun. 16, 2020.
U.S. Appl. No. 16/900,791, filed Jun. 12, 2020.
U.S. Appl. No. 16/943,621, filed Jul. 30, 2020.

* cited by examiner

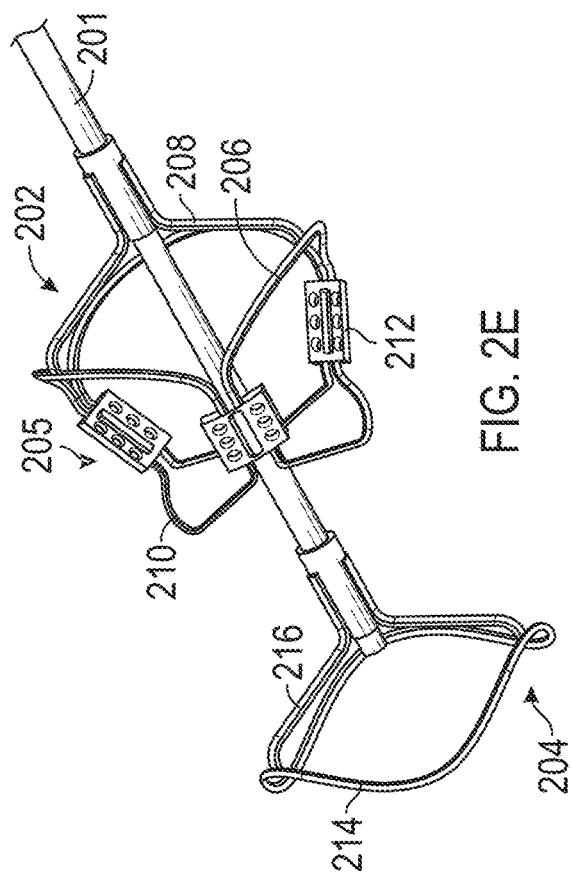
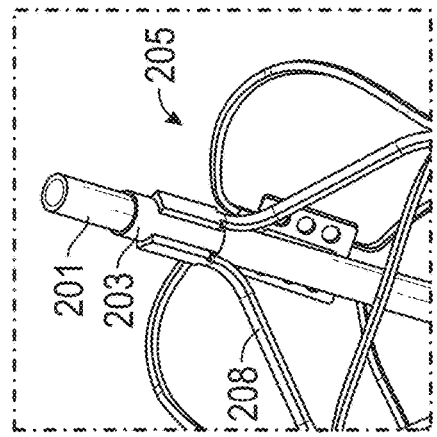
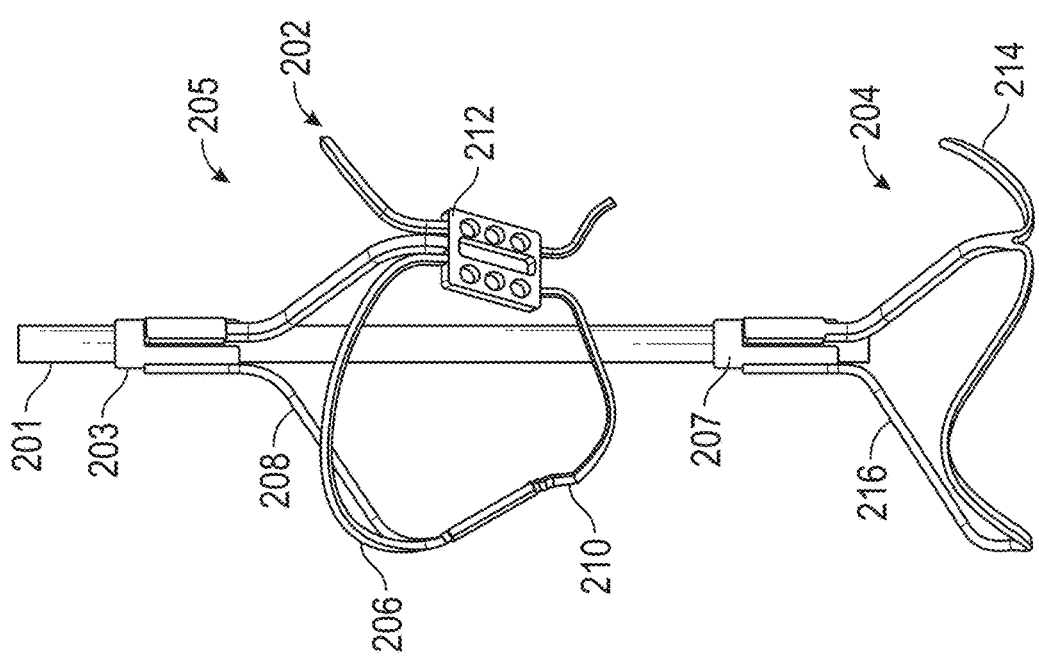

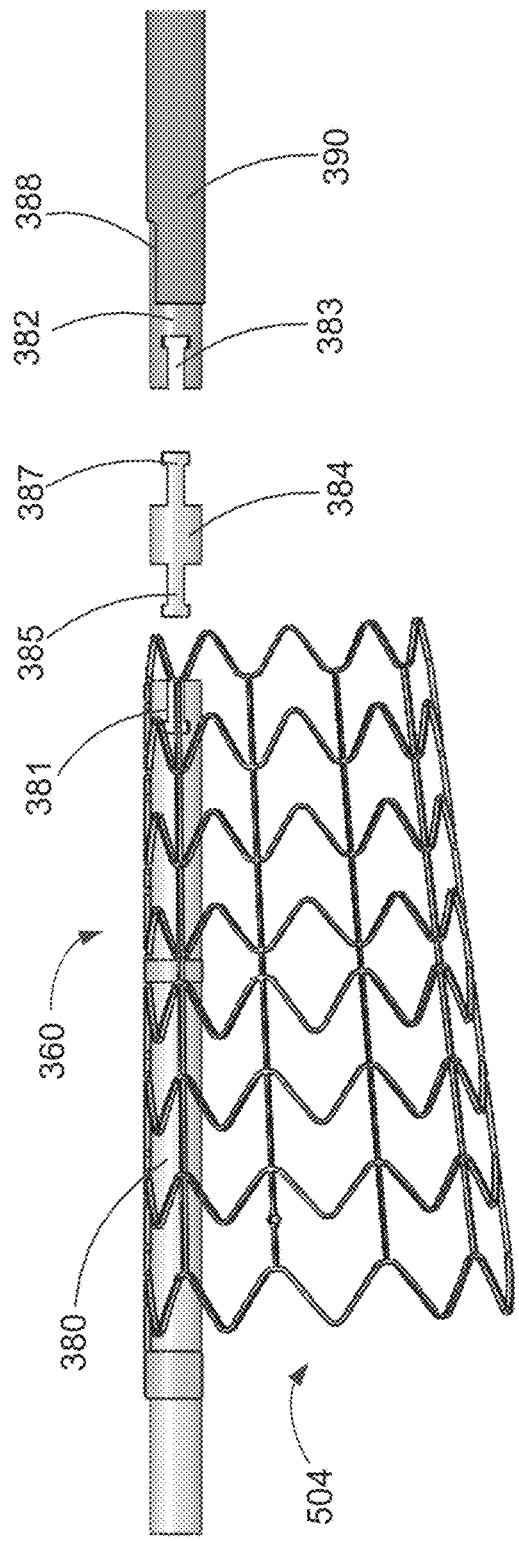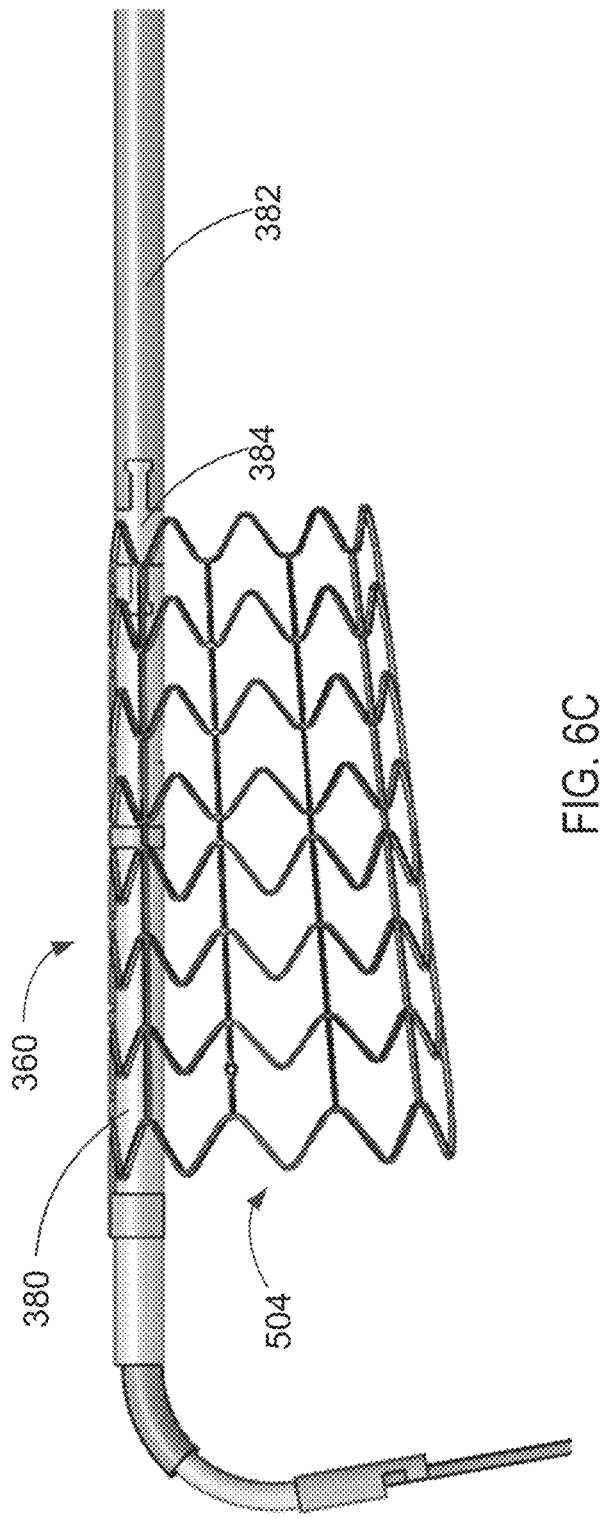
FIG. 6B
FIG. 6C

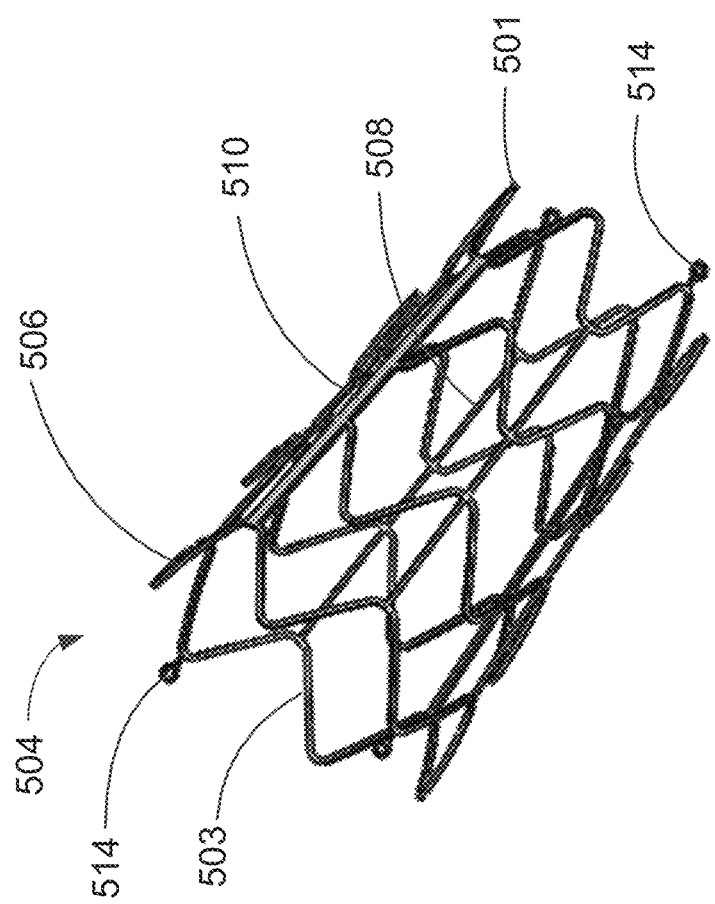

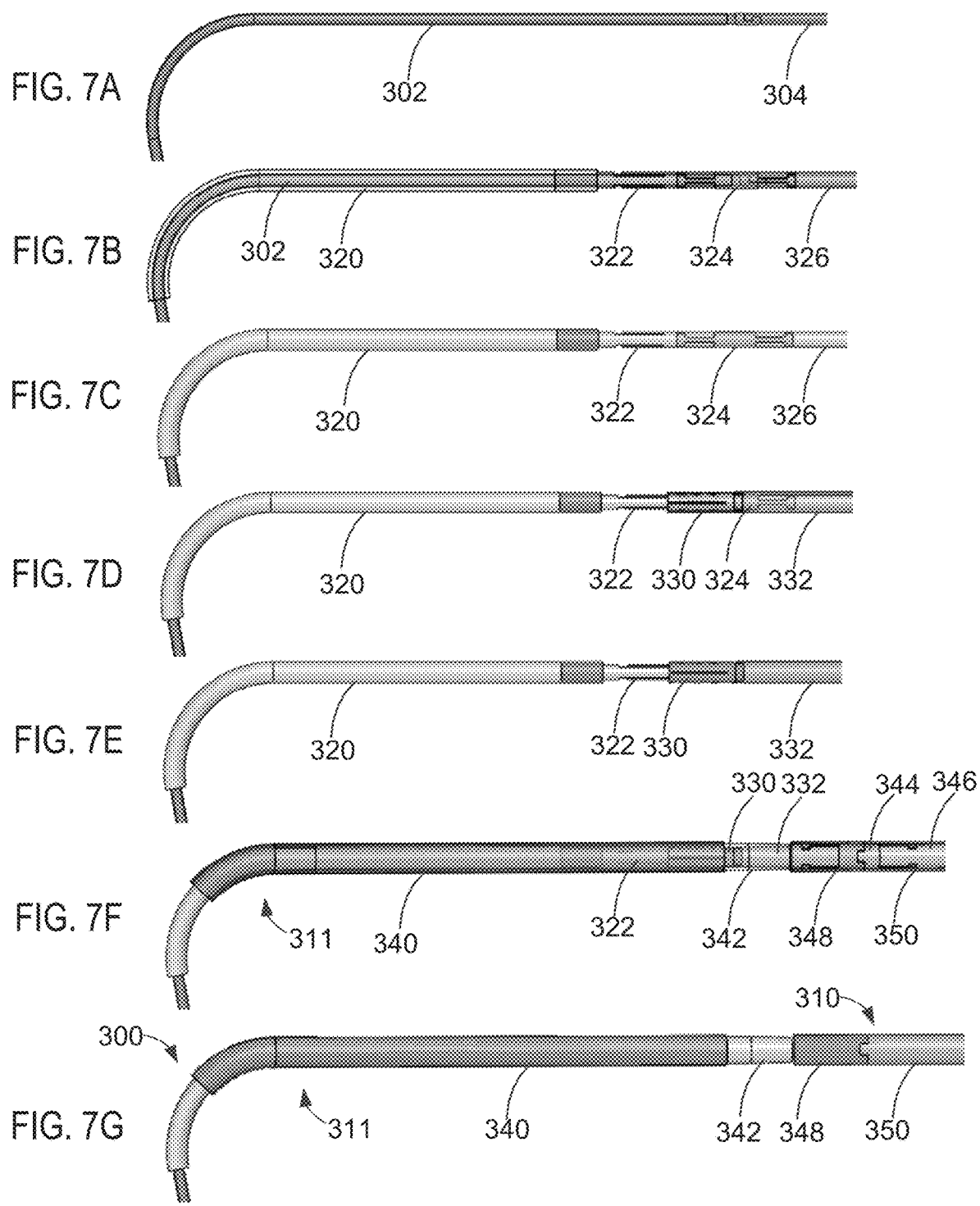

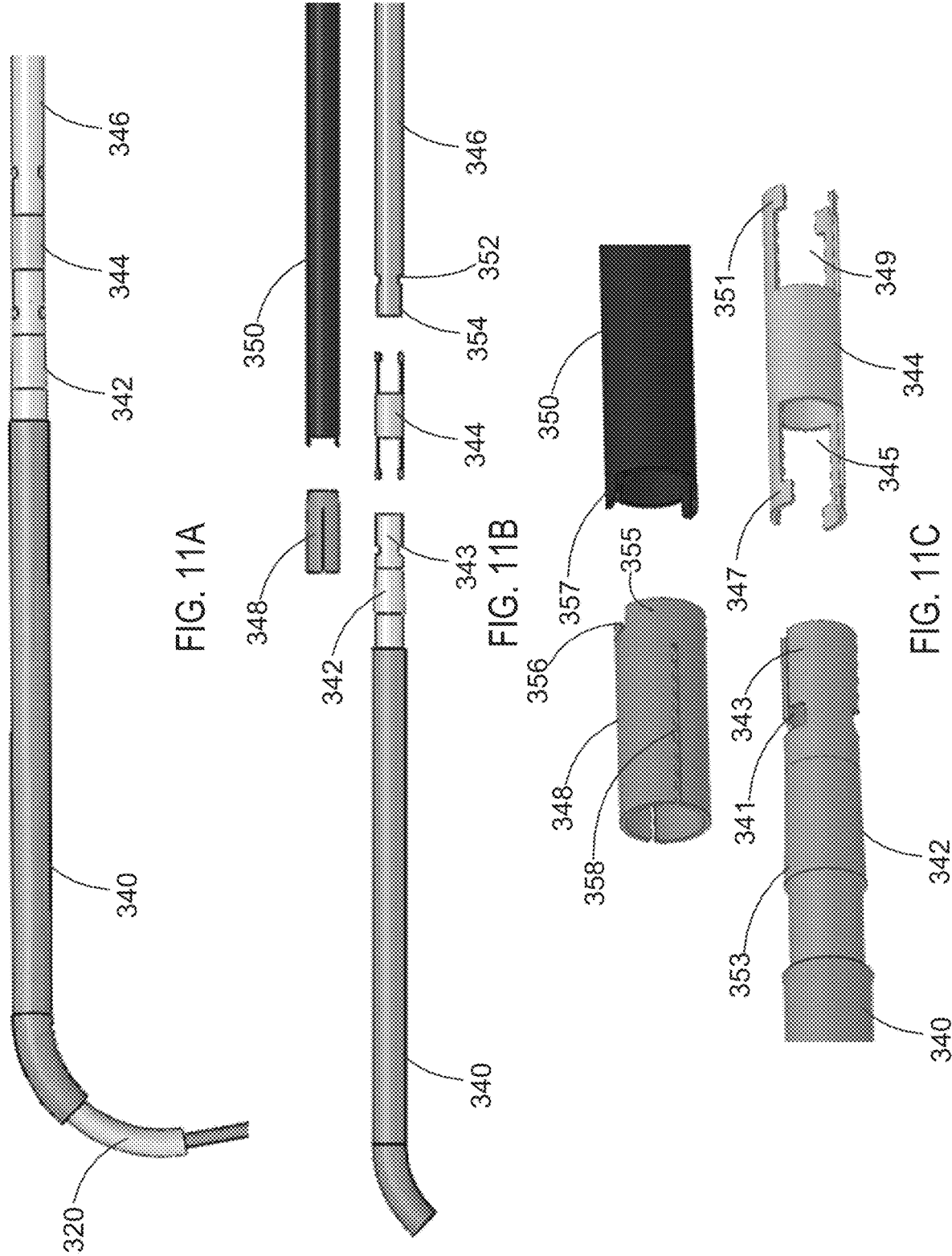

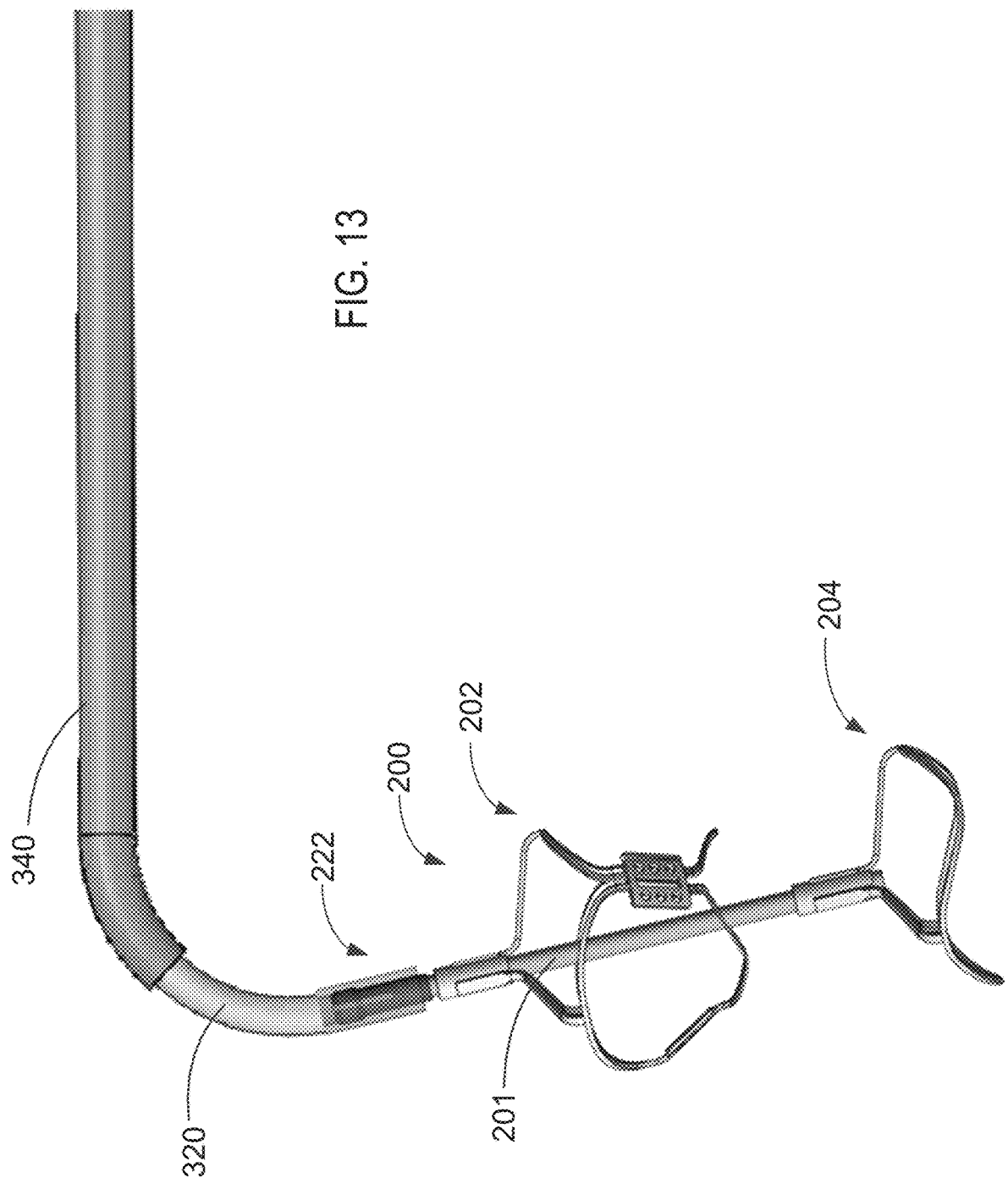

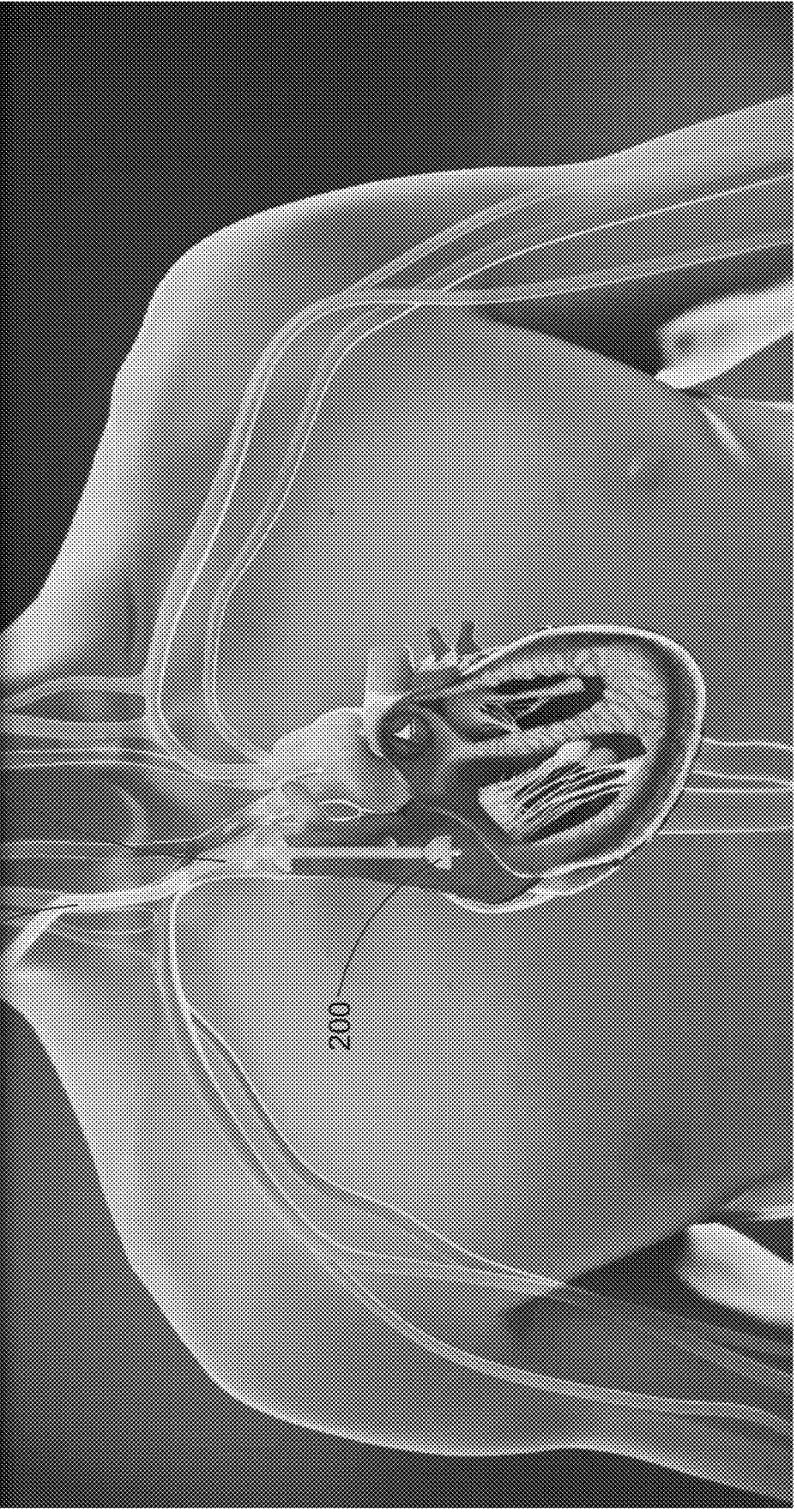

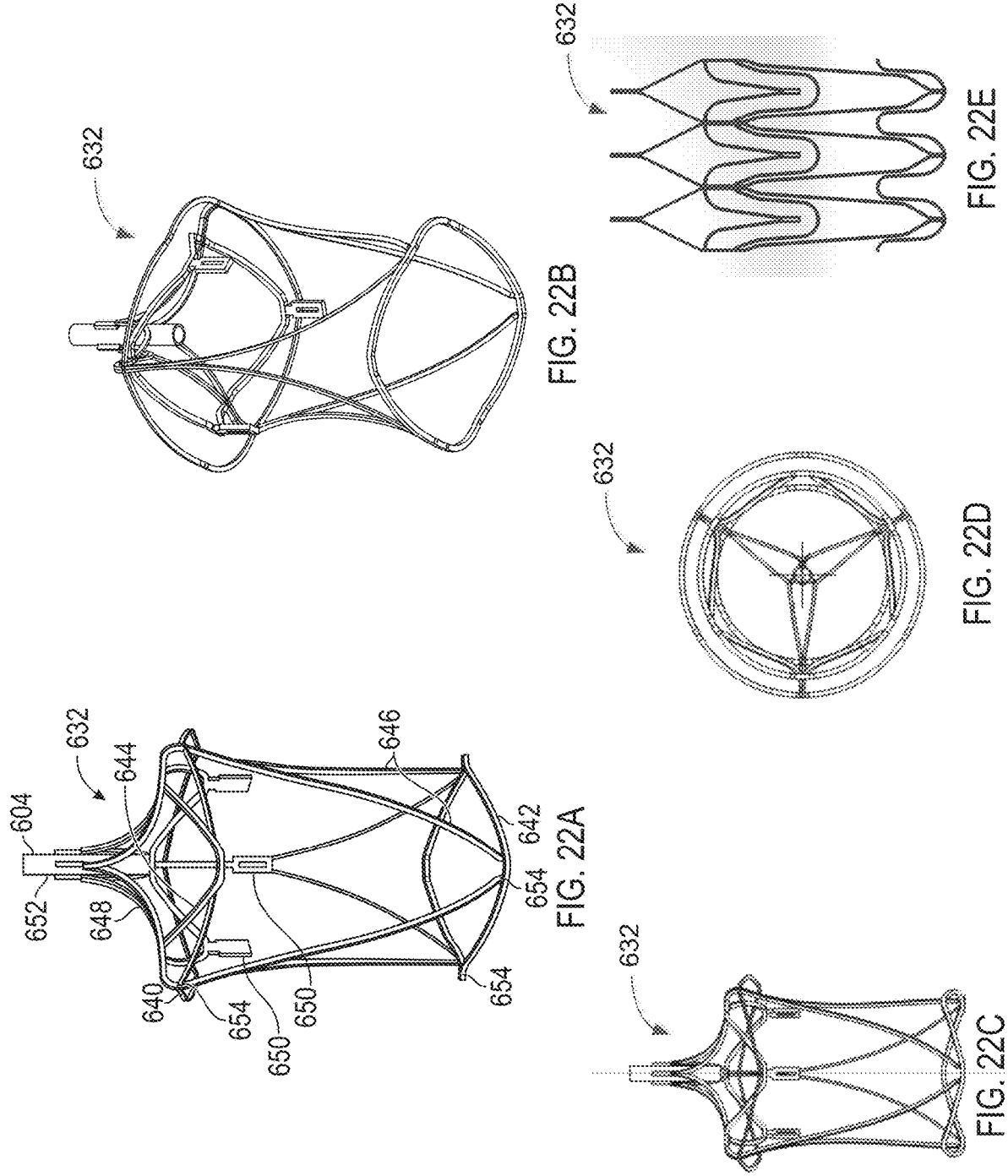

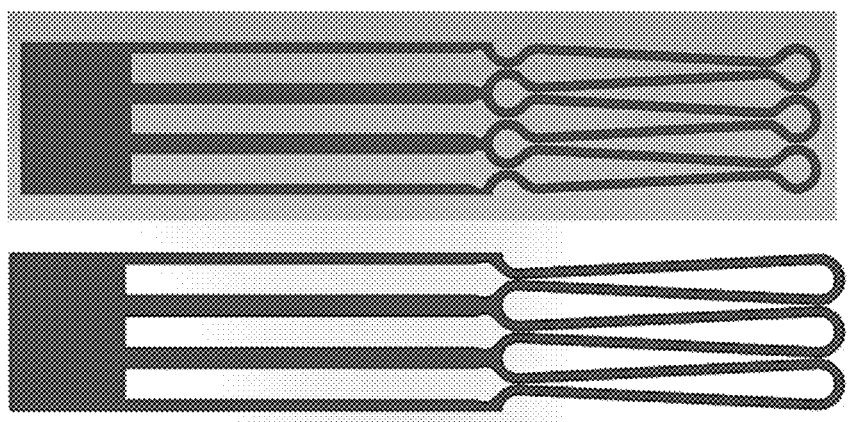
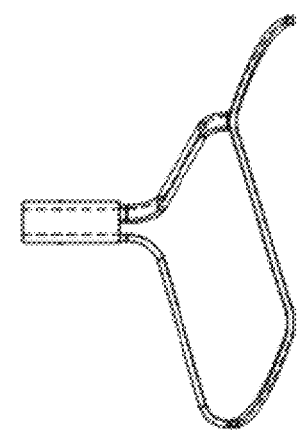
FIG. 23B
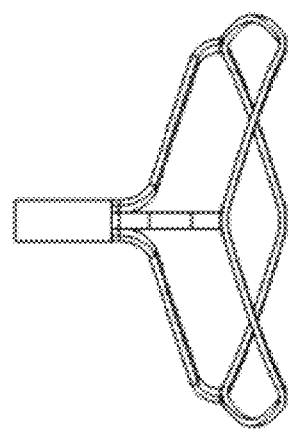
FIG. 23A
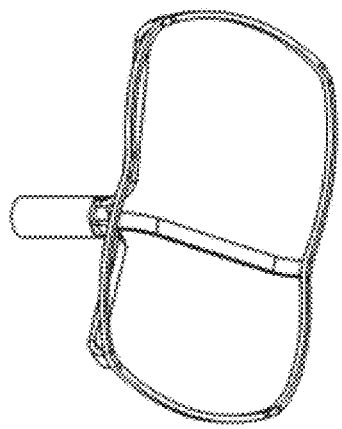
FIG. 23C
FIG. 23D  FIG. 23E

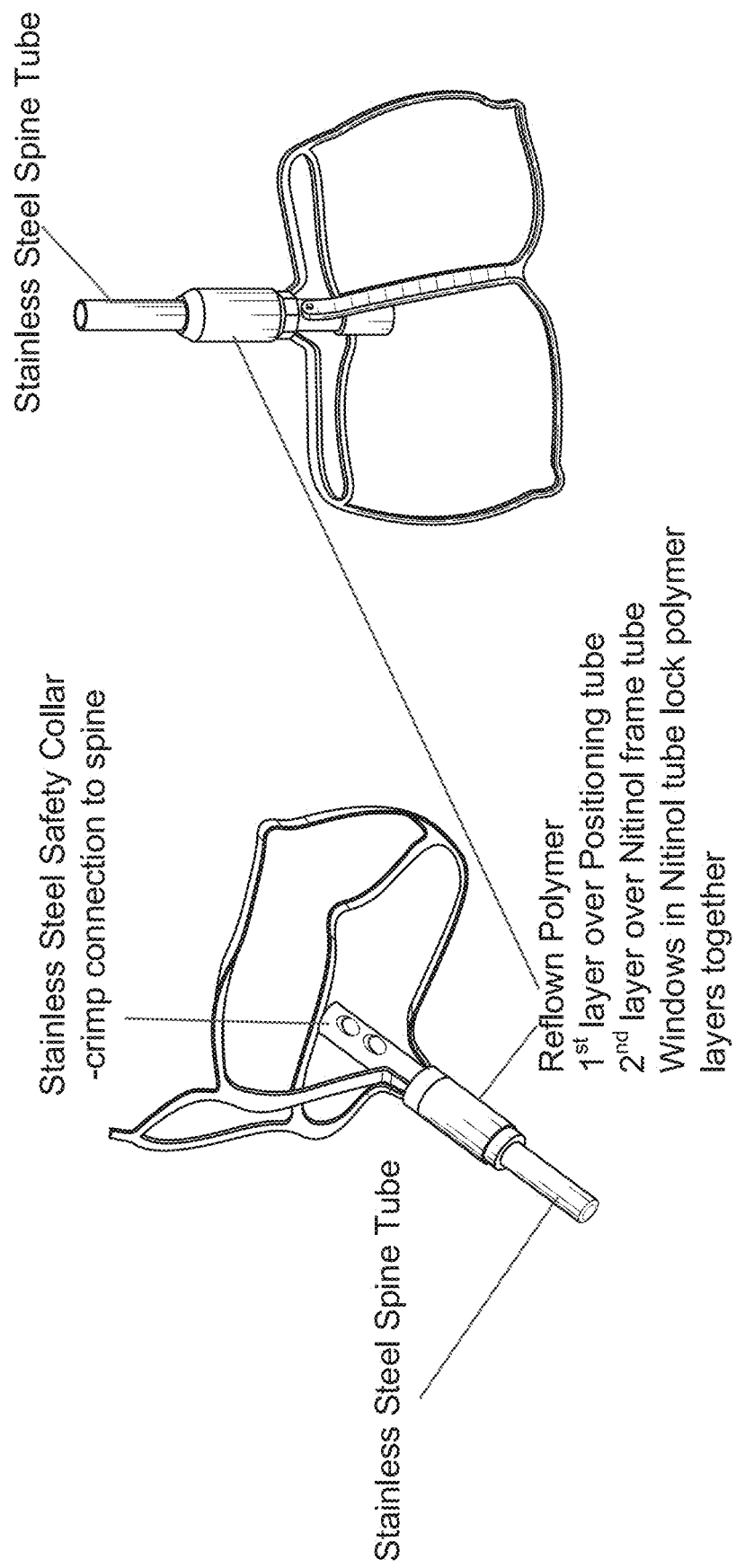

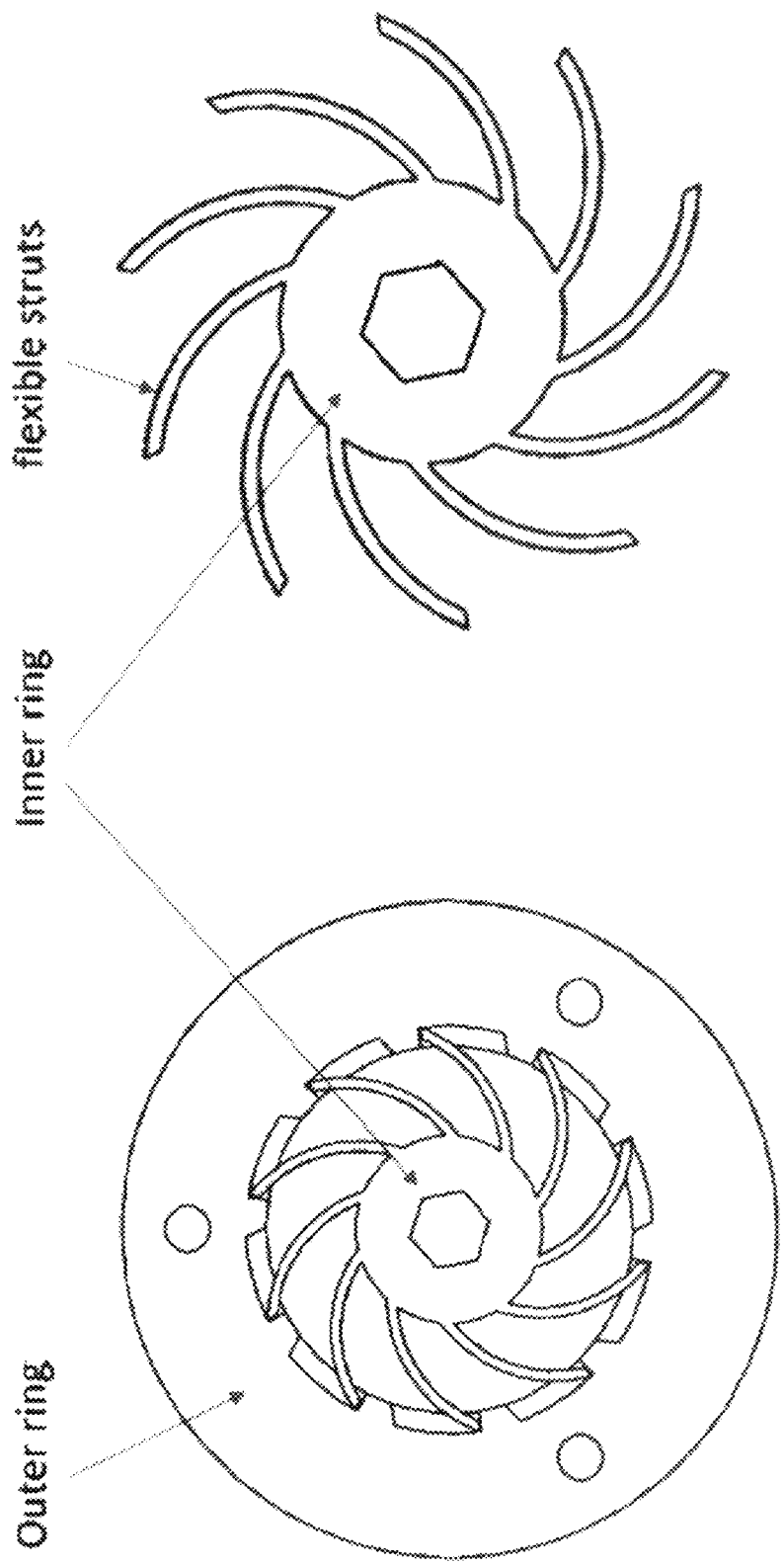

APPARATUS AND METHODS FOR TREATING A DEFECTIVE CARDIAC VALVE

CROSS-REFERENCE TO RELATED APPLICATIONS

This application is a continuation of International PCT Patent Application Serial No. PCT/IB2020/057368, filed Aug. 4, 2020, which claims the benefit of priority to U.S. Provisional Patent Application No. 62/882,961, filed Aug. 5, 2019, the entire contents of each of which are incorporated herein by reference.

FIELD OF THE INVENTION

This application generally relates to apparatus and methods for performing transcatheter or minimally invasive repair of a defective cardiac valve, such as the tricuspid, mitral, pulmonary, and aortic valves.

BACKGROUND OF THE INVENTION

The human heart has four major valves which moderate and direct blood flow in the cardiovascular system. These valves serve critical functions in assuring a unidirectional flow of an adequate blood supply through the cardiovascular system. The mitral valve and aortic valve control the flow of oxygen-rich blood from the lungs to the body. The mitral valve lies between the left atrium and left ventricle, while the aortic valve is situated between the left ventricle and the aorta. Together, the mitral and aortic valves ensure that oxygen-rich blood received from the lungs is ejected into systemic circulation. The tricuspid and pulmonary valves control the flow of oxygen-depleted blood from the body to the lungs. The tricuspid valve lies between the right atrium and right ventricle, while the pulmonary valve is situated between the right ventricle and the pulmonary artery. Together the tricuspid and pulmonary valves ensure unidirectional flow of oxygen-depleted blood received from the right atrium towards the lungs.

Heart valves are passive structures composed of leaflets that open and close in response to differential pressures on either side of the valve. The aortic, pulmonary, and tricuspid valves have three leaflets, while the mitral valve has only two leaflets. Dysfunction of the cardiac valves is common and can have profound clinical consequences. Regurgitation occurs when the valve leaflets do not meet, or "coapt" correctly, thus causing blood to leak backwards through the valve each time the heart pumps. Failure of the valves to prevent regurgitation leads to an increase in the pressure of blood in the lungs or liver and reduces forward blood flow, causing the heart to pump more blood to compensate for the loss of pressure. Such degradation may result in serious cardiovascular compromise or even death. Valvular dysfunction either results from a defect in the valve leaflet or supporting structure, or dilation of the fibrous ring supporting the valve. These factors lead to poor coaptation of valve leaflets, allowing blood to travel in the wrong direction.

Previously known medical treatments to address diseased valves generally involve either repairing the diseased native valve or replacing the native valve with a mechanical or biological valve prosthesis. Previously-known valve prostheses have some disadvantages, such as the need for long-term maintenance with blood thinners, the risk of clot formation, limited durability, etc. Accordingly, valve repair, when possible, usually is preferable to valve replacement. However, most dysfunctional valves are too diseased to be repaired using previously known methods and apparatus. Accordingly, a need exists for a prosthesis capable of assisting heart valve function that enables treatment of a larger patient population, while reducing the need to fully supplant the native heart valve.

For many years, the standard treatment for such valve dysfunction called for surgical repair or replacement of the valve during open-heart surgery, a procedure conducted under general anesthesia. An incision is made through the patient's sternum (sternotomy), and the heart is accessed and stopped while blood flow is rerouted through a heart-lung bypass machine. When replacing the valve, the native valve is excised and replaced with either a mechanical or biological prosthesis. However, these surgeries are prone to many complications and long hospital stays for recuperation.

More recently, transvascular techniques have been developed for introducing and implanting a replacement valve, using a flexible catheter in a manner less invasive than open-heart surgery. In such techniques, a replacement valve is mounted in a compressed state at the end of a flexible catheter and advanced through the blood vessel of a patient until the prosthetic valve reaches the implantation site. The valve then is expanded to its functional size at the site of the defective native valve, usually by inflating a balloon within where the valve has been mounted. By expanding the prosthetic valve, the native valve leaflets are generally pushed aside and rendered ineffective. Examples of such devices and techniques, wherein the native valve is replaced in its entirety by a substitute tissue valve, are described, for example, in U.S. Pat. Nos. 6,582,462 and 6,168,614 to Andersen.

Prostheses have been produced and used for over sixty years to treat cardiac disorders. They have been made from a variety of materials, both biological and artificial. Mechanical or artificial valves generally are made from non-biological materials, such as plastics or metals. Such materials, while durable, are prone to blood clotting and thrombus formation, which in turn increases the risk of embolization and stroke or ischemia. Anticoagulants may be taken to prevent blood clotting that may result in thromboembolic complications and catastrophic heart failure, however, such anti-clotting medication may complicate a patient's health due to the increased risk of hemorrhage.

In contrast, "bio-prosthetic" valves are constructed with prosthetic leaflets made of natural tissue, such as bovine, equine or porcine pericardial tissue, which functions very similarly to the leaflets of the natural human heart valve by imitating the natural action of the heart valve leaflets, coapting between adjacent tissue junctions known as commissures. The main advantage of valves made from tissue is they are not as prone to blood clots and do not absolutely require lifelong systemic anticoagulation.

In recent years, bio-prosthetic valves have been constructed by integrating prosthetic leaflets made from natural tissue into a stent-like supporting frame, which provides a dimensionally stable support structure for the prosthetic leaflets. In more advanced prosthetic heart valve designs, besides providing dimensionally stable support structure for the prosthetic leaflets, the stent-like supporting frame also imparts a certain degree of controlled flexibility, thereby reducing stress on the prosthetic leaflet tissue during valve opening and closure and extending the lifetime of the prosthetic leaflets. In most designs, the stent-like supporting frame is covered with a biocompatible cloth (usually a polyester material such as Dacron™ or polytetrafluoroethylene (PTFE)) that provides sewing attachment points for the prosthetic leaflet commissures and prosthetic leaflets themselves. Alternatively, a cloth-covered suture ring may be attached to the stent-like supporting frame, providing a site for sewing the valve structure in position within the patient's heart during a surgical valve replacement procedure.

While iterative improvements have been made on surgical bio-prosthetic valves over the last several decades, existing bio-prosthetic valves still have drawbacks. In most designs, the bio-prosthetic valve is implanted as a replacement for the native valve, filling the entire space the native valve had occupied. One drawback to this procedure is the mismatch in size and mass between opposing surfaces of the stent-like supporting frame. The mismatch is often due to the variability in the shapes and mechanical characteristics of the stent-like supporting frame. For prosthetic valves with balloon-expandable stent-like supporting frames, the recoil of the supporting frames post-balloon-inflation may lead to perivalvular leaks around the circumference of the prosthetic valve and potential slippage and migration of the valve post-implantation. Another risk associated with prosthetic valves having balloon-expandable supporting frames is potential damage to the prosthetic leaflets of the prosthesis during implantation, when the prosthetic leaflets may be compressed between the balloon and the supporting frame. For prosthetic valves with self-expanding stent-like supporting frames, mismatch may arise due to the deformation/movement of the supporting frame, e.g., slight deformation of the frame into a less than circular shape during normal cardiac movement. Such mismatch may lead to instability among components of a prosthetic valve, resulting in perivalvular leaks and uneven stress distribution in the prosthetic leaflets, resulting in accelerated wear of the valve.

Some innovation has addressed these problems by augmenting, rather than replacing, the native valve. The simplest of these devices is a plug suspended across the center of the valve that allows the native leaflets to coapt against the plug body to block regurgitation, as described in U.S. Pat. No. 7,854,762 to Speziali. Though the plug design helps to prevent regurgitation, the major drawback is that it also blocks some of the blood flow during diastole. Improved prostheses are described in U.S. Pat. Nos. 10,383,729 and 10,682,231 to Quinn and WO 2019/154927, the entire contents of each of which are incorporated herein by reference.

It would be desirable to further enhance designs to, for example, allow easier delivery of a prosthetic device to a cardiac valve, provide a robust structure that ensures integrity of an implanted prosthetic including its prosthetic leaflets, and improve coaptation of the device with the native leaflets to reduce regurgitation.

SUMMARY OF THE INVENTION

The present disclosure provides improved heart valve repair apparatus and methods that, for example, allow more reliable delivery of the prosthetic device to the cardiac valve, provide robust structure, and minimize regurgitation. In accordance with the principles of the present disclosure, the apparatus and methods may be optimized for use in treating cardiac valve regurgitation when the native leaflets of the cardiac valve do not coapt correctly, thus causing blood to leak backwards through the valve as the heart pumps. Advantageously, apparatus of the present disclosure are configured for implantation at a cardiac valve within a blood flow path such that the native leaflets abut the apparatus during the portion of the cardiac cycle when the cardiac valve attempts to close, thereby enhancing native leaflet coaptation and minimizing regurgitation.

In accordance with one aspect of the present invention, a system is provided for implanting a therapeutic heart valve device at a native heart valve (e.g., tricuspid, mitral, pulmonary, or aortic valve) of a patient's heart. The system may include a prosthetic device (e.g., a prosthetic valve) that is implanted at the native heart valve, a support coupled to the prosthetic device, and an actuator coupled to the support. The support may include a delivery portion that is used for delivery and an implantable portion that remains coupled to the prosthetic device after delivery and stays implanted with the prosthetic device. During delivery, the delivery portion is attached to the implantable portion and, after suitable placement of the prosthetic device at the native heart valve, the portions are detached and the delivery portion is removed from the patient. For example, the support may have an elongated shaft with a proximal, delivery portion and a distal, implantable portion that is structured to maintain the prosthetic device at the native heart valve. The actuator may be actuated to cause the components of the distal, implantable portion to lock together, and cause the proximal, delivery portion to detach from the distal, implantable portion at an area (e.g., the detachment area within a blood vessel coupled to the heart such as the inferior vena cava or superior vena cava) responsive to actuation such that the proximal, delivery portion may be removed from the patient while the distal, implantable portion remains implanted within the patient. For example, a clinician may actuate one or more knobs, sliders, buttons, or the like on an actuator, e.g., one or more handles, coupled to the support. The one or more knobs, sliders, buttons, or the like on the actuator may be the same for locking and detachment or may be different. For example, a knob(s) and/or button(s) may be moved in a first direction on the actuator to lock and moved in a second direction (e.g., opposite direction) to detach. The distal, implantable portion of the support may then remain implanted with the prosthetic device to anchor the prosthetic device at a suitable position within the native heart valve.

The support may also permit steering of the prosthetic device during delivery for suitable positioning for implantation. The elongated rail of the support is expected to provide enhanced steering although alternative or additional mechanisms may be used such as pull wire steering. The support further allows for extension and telescoping to increase and/or decrease the length of support for suitable positioning of the prosthetic device at the native cardiac valve. For example, the body support catheter may be capable of telescoping to move the prosthetic device into the suitable position within the native cardiac valve.

The support may include an elongated rail having an elongated rail distal portion at the distal, implantable portion of the elongated shaft and an elongated rail proximal portion at the proximal, delivery portion of the elongated shaft. The elongated rail distal portion may be attached to the elongated rail proximal portion during delivery and detached at the detachment area by the actuator for implantation of the elongated rail distal portion.

In addition, the support may include a body support catheter having a body support catheter distal portion at the distal, implantable portion of the elongated shaft and a body support catheter proximal portion at the proximal, delivery portion of the elongated shaft. The body support catheter distal portion may be attached to the body support catheter proximal portion during delivery and detached at the detachment area by the actuator for implantation of the body support catheter distal portion. For example, the body support catheter distal portion may include a distal body support locking portion and a distal body support connection portion. Additionally, the body support catheter proximal portion may include a distal body support locking portion, and the body support catheter may include a body support catheter lock that may move from a first delivery position to a second locked position over the distal body support locking portion to lock the body support catheter distal portion in an implantable configuration.

In addition, the body support catheter distal portion may include a distal body support connection portion proximal to the distal body support locking portion, and the body support catheter proximal portion may include a body support catheter connection that is transitionable between a collapsed configuration where the body support catheter connection has features that engage and interlink with reciprocal features in the distal body support connection portion of the body support catheter distal portion and an expanded or otherwise releasing configuration where the body support catheter connection disengages with the distal body support connection portion of the body support catheter distal portion.

Additionally, the body support catheter proximal portion may include a body support catheter pusher that may move the body support catheter lock from the first delivery position where the body support catheter connection is maintained in its collapsed configuration, to the second locked position where the body support catheter lock is positioned over the distal body support locking portion of the body support catheter distal portion to lock the body support catheter distal portion in the implantable configuration. The body support catheter pusher may be retracted proximally to expose the body support catheter connection such that the body support catheter connection may transition from the collapsed or otherwise interlinked configuration to the expanded or otherwise disengaged configuration. When the body support catheter lock is in the second locked position, the body support catheter distal portion locks to the elongated rail distal portion and to the shaping catheter distal portion.

Moreover, the support may include a shaping catheter having a shaping catheter distal portion at the distal, implantable portion of the elongated shaft and a shaping catheter proximal portion at the proximal, delivery portion of the elongated shaft. The shaping catheter distal portion may be attached to the shaping catheter proximal portion during delivery and detached at the detachment area by the actuator for implantation of the shaping catheter distal portion. The shaping catheter distal portion may further include a distal shaping locking portion and the shaping catheter may include a shaping catheter lock that may move from a first delivery position to a second locked position over the distal shaping locking portion to lock the shaping catheter distal portion in an implantable configuration. In addition, the shaping catheter distal portion may include a distal shaping connection portion proximal to the distal shaping locking portion, and the shaping catheter proximal portion may include a shaping catheter connection that is transitionable between a collapsed or otherwise interlinked configuration where features of the shaping catheter connection engage with the reciprocal interlinking features of the distal shaping connection portion of the shaping catheter distal portion and an expanded or otherwise releasing configuration where the shaping catheter connection disengages with the distal shaping connection portion of the shaping catheter distal portion.

Additionally, the shaping catheter proximal portion may include a shaping catheter pusher that may move the shaping catheter lock from the first delivery position where the shaping catheter connection is maintained in its collapsed configuration, to the second locked position where the shaping catheter lock is positioned over the distal shaping locking portion of the shaping catheter distal portion to lock the shaping catheter distal portion in the implantable configuration. The shaping catheter pusher may be retracted proximally to expose the shaping catheter connection such that the shaping catheter connection may transition from the collapsed configuration to the expanded configuration. When the shaping catheter lock is in the second locked position, the shaping catheter distal portion locks to the anchor tube in the implantable configuration The support further may include an anchor for anchoring the support to an anchor site within the patient, e.g., to a blood vessel coupled to the heart. For example, the anchor may be a stent such as a self-expandable stent that may be tapered and may be coupled to the support adjacent to the detachment area. The anchor may have alternative or additional feature to enable robust mating to the anchor to specific location in the vessel where it is positioned. The detachment area may be within the anchor. Additionally, the support may include an anchor tube coupled to the distal, implantable portion of the elongated shaft of the support, such that the anchor is coupled to the anchor tube. The proximal, delivery portion of the support may detach from the distal, implantable portion within the anchor tube. The proximal end of the implantable anchor tube maybe fully enveloped by the anchor.

The anchor tube may include an anchor tube distal portion at the distal, implantable portion of the elongated shaft and an anchor tube proximal portion at the proximal, delivery portion of the elongated shaft. The anchor tube distal portion may be attached to the anchor tube proximal portion during delivery and detached at the detachment area by the actuator for implantation of the anchor tube distal portion. In addition, the anchor tube distal portion may include a distal anchor tube connection portion, and the proximal anchor tube may include an anchor tube connection that is transitionable between a collapsed configuration where the anchor tube connection engages with the distal anchor tube connection portion and an expanded configuration where the anchor tube connection disengages with the distal anchor tube connection portion. Moreover, the anchor tube further may include an anchor tube sleeve that may move from a first delivery position where anchor tube connection is maintained in the collapsed configuration, to a second retrieval position such that the anchor tube connection transitions from its collapsed configuration to the expanded configuration.

In some examples, the support includes an elongated rail disposed within a first catheter disposed within a second catheter, such that the distal portions of each of the elongated rail, the first catheter, and the second catheter may lock together within the patient responsive to actuation. In this manner, the distal portions of the elongated rail, the first catheter, and the second catheter remain implanted with the prosthetic device while proximal portions of the elongated rail, the first catheter, and the second catheter are not implanted.

The prosthetic device may include a frame forming a conduit, an outer skirt, and a plurality of prosthetic leaflets. For example, the prosthetic device may be a prosthetic valve with a plurality of prosthetic leaflets that open and close during the cardiac cycle responsive to natural pressure changes at the cardiac valve that cause the native leaflets to open and close. The frame may include a proximal ring and a distal ring. The proximal ring may be coupled to a plurality of prosthetic leaflet anchors, and the plurality of prosthetic leaflet anchors may include a plurality of suture eyelets for permitting suturing of the plurality of prosthetic leaflets to the frame. In addition, the frame further may include an inner ring disposed distal to the proximal ring, the inner ring coupled to the proximal ring via the plurality of prosthetic leaflets anchors.

The frame of the prosthetic valve also may include a spine that may be coupled to the support. The frame may be formed from a single piece or multiple pieces. For example, the spine may include a spine elongated shaft that extends through the prosthetic device. The proximal ring may be coupled to the spine via a plurality of proximal tethers, and the distal ring may be coupled to the spine via a plurality of distal tethers. Moreover, the spine may include a spine connector having a first geometry, and a distal end of the support may include a support connector having a second geometry that may engage or interlink with the first geometry of the spine connector. For example, the support further may include a sleeve, which may cover and compress, or an otherwise radially constrained feature that may be disposed over the support connector and the spine connector when the support connector is engaged with the spine connector.

In accordance with another aspect of the present invention, the spine connector may include at least one prong and sleeve or at least two prongs, each of the prongs having an snap fit portion, and the support connector may have a cavity having a first portion with a first cross-sectional area and a second portion with a second cross-sectional area larger than the first cross-sectional area. Accordingly, the spine connector may be inserted within the cavity of the support connector such that the prongs bend radially inward until the snap fit portion of the prongs engages with the second portion of the cavity. In accordance with another aspect of the present invention, the spine connector may include a first threaded portion, and the support connector may include a second threaded portion that may mate with the first threaded portion of the spine connector. Moreover, the system may include an inner torque limiting ring and an outer torque limiting ring coupled to the inner torque limiting ring via a plurality of flexible struts, such that the inner torque limiting ring may engage with the first and second threaded portions to permit tightening of a connection between the first and second threaded portions while limiting torque applied to the first and second threaded portions via the outer torque limiting ring. In an alternative approach the male and female threaded sections may include features that serve to compress or deflect during engagement in a manner that prevent loosening or disengagement when the connector is subjected to vibration or cyclic loading associated with the cardiac cycle. Example embodiments may be a compressible o-ring or a spring washer.

In accordance with another aspect of the present invention, a delivery system for implanting a therapeutic heart valve device at a native heart valve of a patient's heart is provided. The delivery system includes a proximal elongated shaft that may be detachably coupled, in a delivery state, to a distal elongated shaft that may be coupled to a prosthetic device. The proximal elongated shaft and the distal elongated shaft have a length, when coupled, to percutaneously deliver the prosthetic device to the native heart valve for implantation. The delivery system further may include an actuator coupled to the proximal elongated shaft. The actuator may be actuated to cause the proximal elongated shaft to detach from the distal elongated shaft at a detachment area within the patient responsive to actuation to implant the prosthetic device and the distal elongated shaft within the patient in the deployed state. For example, the proximal elongated shaft may include an elongated rail disposed within a body support catheter disposed within a shaping catheter, each structured to attach to a corresponding component in the distal elongated shaft during delivery and to detach for implantation.

In accordance with another aspect of the present invention, a method for implanting a therapeutic heart valve device at a native heart valve of a patient's heart is provided. The method may include advancing the prosthetic device to the native heart valve, anchoring the distal, implantable portion of the support within the patient to maintain the prosthetic device at the native heart valve, and actuating the actuator coupled to the support to cause the proximal, delivery portion to detach from the distal, implantable portion at a detachment area within the patient responsive to actuation.

In accordance with another aspect of the present invention, the system for implanting a therapeutic heart valve device at a native heart valve of a patient's heart may include a prosthetic device that may be implanted at the native heart valve, and a support coupled to the prosthetic device and including an elongated shaft having a distal, implantable portion having a lock. The support maintains the prosthetic device at the native heart valve. The system further may include an actuator coupled to the support. The actuator may be actuated to activate the lock to lock the distal, implantable portion in an implantable configuration within the patient responsive to actuation. In addition, the support may include an elongated rail disposed within a first catheter disposed within a second catheter, such that the distal portions of each of the elongated rail, the first catheter, and the second catheter may lock together within the patient responsive to actuation. Moreover, the system may include a second lock that may lock the distal, implantable portion to an anchor system within the patient responsive to actuation at the actuator. The elongated shaft of the support may include a proximal, delivery portion, such that the actuator may be actuated to cause the proximal, delivery portion to detach from the distal, implantable portion at a detachment area within the patient responsive to actuation.

In accordance with some aspects of the present invention, the prosthetic device may be a prosthetic coaptation body that may be a plug/spacer or may be a prosthetic valve contained in a conduit to reduce regurgitation, that is inserted through a blood vessel on a support that may extend out of the heart for anchoring in the blood vessel. The conduit is preferably designed to allow the native leaflets to continue to move and coapt against the outer surface of the conduit when the native leaflets naturally close during the cardiac cycle. The outer surface may be designed to minimize trauma to the native leaflets by surface texturing or selection of material properties. The support may include a rail and/or a steerable catheter, which is coupled to the conduit and extends from the conduit's proximal end. The rail and/or steerable catheter may extend into a tube coupled to a stent, or otherwise anchoring embodiment, engaged to a blood vessel. The stent and tube act to stabilize the rail and/or steerable catheter and may bias it to one side of the vessel. The rail may have a predefined bend to properly position the conduit across the native valve. The steerable catheter may be used to position the conduit across the native valve and then can be locked in place. If the position of the conduit needs to be adjusted, the steerable catheter may be steered post-implantation through manual and/or motorized controls.

The support may have sufficient stiffness to suspend and maintain the prosthetic coaptation body across the native cardiac valve without contacting (or anchoring to) cardiac tissue such as the native valve annulus, atrial tissue, and/or ventricular tissue. The support may be anchored outside the heart, for example, in a blood vessel coupled to the heart such as the superior vena cava or inferior vena cava. Advantageously, this anchoring outside the heart and allowing the prosthetic coaptation body to be suspended in a free-standing manner in the heart reduces tissue damage inside the heart as compared to other prosthetic heart valve designs that are anchored to tissue within the heart. The support may be coupled to the prosthetic coaptation body by rigid or stiff tethers, which hold the conduit in place more accurately than the tensile wires used in previous designs. In some examples, the support does not extend distally past the prosthetic valve and may be coupled to the prosthetic coaptation body only at the prosthetic coaptation body's proximal end and distal end or only at the proximal end or only at the distal end. The support may be coupled to the inner ring of the frame via radially extending tether arms. The conduit shape is supported by a frame, which may be laser cut from a metal tube. In some examples, the frame has a proximal outer ring at its proximal end and a distal outer ring at its distal end.

The outer rings may be coupled together by longitudinal struts. The longitudinal struts may be angled, for example, towards one another to form a plurality of triangle-like shapes extending radially around the frame. Alternatively, the frame does not have struts between the proximal and distal rings such that the skirt is unsupported between the proximal and distal rings.

The outer surface of the prosthetic coaptation body may be formed by an outer skirt. The outer skirt may be made of rigid material or compliant material such as pericardium. The outer skirt may extend around the circumference of the frame to form an outer surface to which the native leaflets coapt when closed during the cardiac cycle. The side walls of the outer skirt may be formed from flexible material to enhance coaptation with the native leaflets when the native leaflets close. The frame also may contain an inner ring that may be located at its proximal end may be roughly concentric with the proximal outer ring. The frame may have predefined kink points to allow for reliable transition from the compressed delivery state into the expanded deployed state. The proximal outer ring, the inner ring, and/or the distal outer ring may exhibit a sinusoidal, triangular or other oscillating shape to further allow reliable compression and expansion.

The prosthetic coaptation body may include a proximal skirt that is coupled to and fills the space between the inner ring and proximal outer ring. The proximal skirt may be made of rigid material or of compliant material such as pericardium. The proximal skirt and outer skirt may be integrally formed of a single piece of material. The proximal skirt and outer skirt allow the native valves to coapt against the conduit to help prevent regurgitation. Prosthetic leaflets may be coupled to the inner ring thereby forming a valve. The prosthetic leaflets may also be coupled to slotted leaflet mounting features. The prosthetic leaflets are preferably made of compliant material such as pericardium and allow blood to flow distally through the conduit but prevent blood from flowing proximally through the conduit.

To implant the device, the rail and/or steerable catheter and the prosthetic coaptation body may be inserted into a delivery sheath. The prosthetic coaptation body collapses into its compressed delivery state. The anchor and anchor tube may be contained within the same delivery sheath. A sheath introducer may be percutaneously inserted into a blood vessel. The delivery sheath may be inserted through the sheath introducer and moved through the blood vessel to the heart. The prosthetic coaptation body is then exposed from the distal end of the sheath and expands into its expanded deployed state (e.g., self-expands or expands via an expandable device such as a balloon). The steerable catheter and/or rail is then manipulated to move the prosthetic coaptation body across the native valve. The delivery sheath is retracted, exposing the anchor, which expands and engages the walls of the blood vessel (e.g., superior vena cava (SVC) or inferior vena cava (IVC)). The anchor tube, which is coupled to the anchor, is also exposed and may contain the proximal end of the implantable portion of the rail and/or steerable catheter. An operator may use an actuator of a handle at the proximal region of the heart valve therapeutic device to control the movement of the steerable catheter to position the conduit or prosthetic coaptation body. Once the prosthetic coaptation body is properly positioned within the native valve and the anchor is anchored in the blood vessel, the steerable catheter may be locked. A catheter lock may be used to lock the anchor tube to the rail and/or steerable catheter maintaining the prosthetic coaptation body suspended across the native valve. The delivery sheath and sheath introducer may be removed once the prosthetic coaptation body and anchor are deployed and the proximal end of the implantable portion of the elongated support is implanted, thereby fully implanting components of the device. Subcutaneously implanted manual and/or motorized controllers may adjust the position of the conduit after implantation via the steerable catheter.

BRIEF DESCRIPTION OF THE DRAWINGS

FIGS. 2D and 2E are perspective views of an exemplary frame of the prosthetic device of FIGS. 2A-2C.

FIG. 2F is a close up view of an exemplary step up of the frame of the prosthetic device of FIGS. 2A-2C.

FIG. 6B is a perspective view of an exemplary components of the anchor tube of the detachable support.

FIG. 6C is a perspective view of the anchor tube of the detachable support in an engaged position without the anchor tube sleeve shown.

FIG. 6F is a perspective view of an exemplary stent of the anchor of FIG. 6A.

FIG. 7A illustrates an exemplary elongated rail of the detachable support of FIGS. 5A and 5B in the attached, delivery state in accordance with some aspects.

FIGS. 7B to 7E illustrate an exemplary body support catheter of the detachable support of FIGS. 5A and 5B in the attached, delivery state in accordance with some aspects.

FIGS. 7F and 7G illustrate an exemplary shaping catheter of the detachable support of FIGS. 5A and 5B in the attached, delivery state in accordance with some aspects.

FIG. 11A illustrates the shaping catheter of FIGS. 7F and 7G without the shaping catheter lock and shaping catheter pusher.

FIGS. 11B and 11C are perspective views of exemplary components of the shaping catheter of FIGS. 7F and 7G.

FIG. 13 illustrates the detachable support coupled to an exemplary frame of the prosthetic device.

FIGS. 17A to 17H are views of an exemplary method for introducing the prosthetic device of the heart valve therapeutic device across a native heart valve for implantation.

FIGS. 22A and 22B are perspective views of an exemplary frame of the prosthetic coaptation body of FIGS. 21A and 21B.

FIGS. 22C and 22D are, respectively, side and top views of the frame of FIGS. 22A and 22B, and FIG. 22E shows a laser-cut, flat pattern of the frame of FIGS. 22A and 22B.

FIGS. 23A, 23B, and 23C are perspective views of another exemplary frame of a prosthetic coaptation body for the heart valve therapeutic device that are well-suited for an acute treatment and FIGS. 23D and 23E show exemplary laser-cut, flat pattern of the exemplary frame.

FIGS. 23F and 23G show illustrative photos of the reflown polymer coatings over the Nitinol frame components and the stainless steel positioning tubes.

FIGS. 24B to 24D illustrate exemplary torque limiting systems that may be used to limit torqueing during coupling of the support to the prosthetic device.

DETAILED DESCRIPTION OF THE INVENTION

Figure 1:
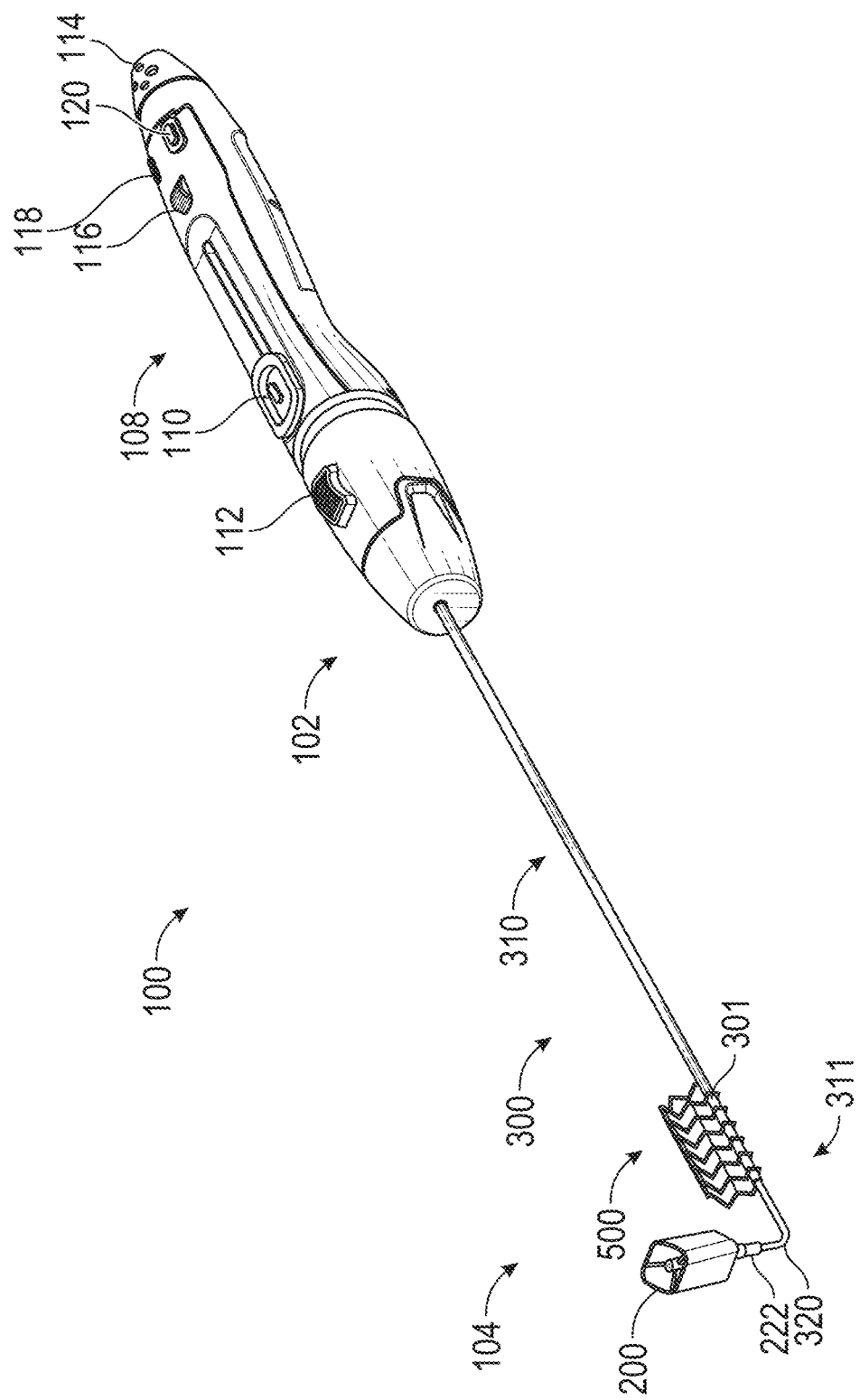
FIG. 1 is a perspective view of an exemplary heart valve therapeutic device for repairing a defective heart valve.

Embodiments of the present invention are directed to exemplary systems and methods for reducing cardiac valve regurgitation. Provided herein is a prosthetic device that may contain a prosthetic coaptation body to be positioned at a native cardiac valve. The prosthetic device may be suspended across the native heart valve by a support. For example, the support may be coupled to the prosthetic coaptation body and extend out of the heart into an adjacent blood vessel coupled to the heart (e.g., superior vena cava, inferior vena cava). The support may be coupled to the blood vessel with an anchor that preferably is expandable and has a stent structure. In some examples, the support is structured to suspend the prosthetic coaptation body in the native valve in a free-standing manner without anchoring to cardiac tissue, thereby minimizing damage to the heart. The prosthetic coaptation body may be formed from a frame (e.g., metal frame such as Nitinol) that is at least partially covered by a skirt made from biocompatible material, and also includes prosthetic leaflets. The frame, biocompatible material, and prosthetic leaflets may together form a conduit through which blood flows when the prosthetic leaflets open during the cardiac cycle.

The design of the prosthetic device improves coaptation with the native heart valve leaflets and allows for a more reliable delivery. The prosthetic device may be implanted percutaneously via a blood vessel, e.g., the jugular vein, femoral vein, femoral artery, for the treatment of a defective cardiac valve, e.g., tricuspid, mitral, pulmonary, or aortic valve. In one example, the prosthetic device may be used to treat symptomatic primary or functional (secondary) tricuspid regurgitation. For example, the prosthetic device may be positioned between the native tricuspid valve leaflets to restore the valve function without altering the native anatomy or obstructing flow during diastole and held in place by an anchor system deployed in an anchor site, e.g., within the heart and/or within a blood vessel coupled to the heart such as the superior vena cava (SVC).

The frame may be designed with predefined kink points or collapsible/expandable features to allow the conduit to be compressed into a delivery sheath without being damaged, and to more reliably expand upon delivery. The frame may have a proximal ring and a distal ring, as well as an inner ring coupled to the proximal ring via a plurality of skirt anchors to which the prosthetic valve leaflets may be attached. One or more of the rings may exhibit a scallop, sinusoidal, zig-zag shape or otherwise oscillating pattern in the expanded state to further improve the compression and expansion of the frame. The skirt of the prosthetic coaptation body may join the proximal ring to the distal ring to improve coaptation of the native valve against the skirt. The prosthetic coaptation body may be coupled to the support by a plurality of tethers that may be formed of shape-memory material such as Nitinol. The tethers may be rigid or stiff and hold the prosthetic coaptation body in position more accurately than tensile wires.

Referring to FIG. 1, an illustrative embodiment of exemplary heart valve therapeutic device 100 in accordance with the principles of the present disclosure is described. Illustratively, heart valve therapeutic device 100 is designed for repairing a defective tricuspid valve. As will be understood by a person having ordinary skill in the art, heart valve therapeutic device 100 may be readily adapted for other cardiac valves such as the mitral valve, aortic valve, or pulmonary valve.

As illustrated in FIG. 1, heart valve therapeutic device 100 may include prosthetic device 200 coupled to support 300 at distal region 104 of heart valve therapeutic device 100, as well as actuator 108 at proximal region 102 of heart valve therapeutic device 100. Actuator 108 may include one or more handles configured to be manipulated by a clinician to deliver the system for implantation. having a plurality of interfaces, Support 104 may include an elongated shaft including proximal, delivery portion 310 and distal, implantable portion 311, such that proximal, delivery portion 310 is removeably coupled to distal, implantable portion 311 at detachment area 301, and distal, implantable portion 311 is coupled to prosthetic device 200 at valve connection area 222. Heart valve therapeutic device 100 is structured to deliver prosthetic device 200 to a damaged native heart valve for an acute or chronic treatment, and certain components of heart valve therapeutic device 100 such as distal, implantable portion 311 of support 300 may be designed to be fully implanted long-term for the chronic treatment.

Distal, implantable portion 311 of support 300 further may include anchor 500. Anchor 500 may be formed of a stent structure and is preferably collapsible in a contracted, delivery state and expandable to an expanded, deployed state to anchor the prosthetic device at the native cardiac valve. For example, anchor 500 may contact the inner wall of a blood vessel (e.g., the SVC or IVC) to anchor distal, implantable portion 311 of support 300 intraluminally, thereby anchoring prosthetic device 200 in a free-standing, suspended manner in the native heart valve. As shown in FIG. 1, anchor 500 may be positioned on distal, implantable portion 311 adjacent to detachment area 301 of support 300. In some examples, detachment area 301 is located within anchor 500 such that the distal end of anchor 500 provides the distal-most position of the implantable portion of the device.

Actuator 108 is designed to be held and manipulated by a clinician and may include one or more interfaces such as interfaces 110, 112, 114, 116, 118, and 120. As illustrated, actuator 108 may be coupled to the proximal region support 300 and interfaces 110, 112, 114, 116, 118, and 120 may each be coupled to corresponding components of support 300 such that actuation of the interfaces cause movements described herein for delivery and implantation of prosthetic device 200. Interfaces 110, 112, 114, 116, 118, and 120 may be buttons, sliders, knobs, or the like that are actuated to deliver prosthetic device 200, manipulate support 300 for suitable implantation, lock distal components of distal, implantable portion 311 together, and/or to detach proximal, delivery portion 310 from distal, implantable portion 311. Accordingly, responsive to actuation of the interfaces of actuator 108, prosthetic device 200 may be manipulated for suitable positioning within the target native heart valve, the distal components of distal, implantable portion 311 may be locked together, and proximal, delivery portion 310 may be detached from distal, implantable portion 311. For example, interface 110 may be operatively coupled to the shaping catheter for making extension adjustments to extend prosthetic device 200 into implantation position. Interface 112 may be operatively coupled to the elongated rail for adjusting the angle of the rail for positing the prosthetic device 200 at the appropriate angle relative to the native heart valve. Interface 114 may be operatively coupled to the body support catheter for telescoping adjustments to extend or retract prosthetic device 200 to the native heart valve. Interface 116 may be operatively coupled to a first lock to lock distal, implantable components of the support together for implantation. For example, interface 116 may be operatively coupled to the body support catheter pusher for actuating the body support catheter lock. Interface 118 may be operatively coupled to a second lock to lock different distal, implantable components of the support together for implantation, such as locking to the anchor system. For example, interface 118 may be operatively coupled to the shaping catheter pusher for actuating the shaping catheter lock. Interface 120 may be operatively coupled to the anchor tube sleeve for disengaging the anchor tube, as described in further detail below.

In some configurations, an interface, e.g., interface 116, 118, may be moved distally along handle to cause portions of support 300 to move distally in a corresponding manner to facilitate locking of the distal components of distal, implantable portion 311 to secure the components in the implantable, locked position suitable for short-term (acute) or long-term (chronic) implantation of prosthetic device 200 at the native cardiac valve, as explained in detail below. Further, the same or different interface(s) may be moved proximally along the handle to cause detachment of the proximal, delivery portion 310 from distal, implantable portion 311 such that proximal, delivery portion 310 may be removed from the patient while distal, implantable portion 311 remains implanted, as explained in detail below. Interfaces 110, 112, 114, 116, 118, and 120 may be manually operated or controlled remotely using motorized controls, and actuator 108 may be actuated to reattach proximal, delivery portion 310 to distal, implantable portion 311 post-implantation in a follow-up procedure to permit adjustments after implantation of prosthetic device 200.

Prosthetic device 200 may be a prosthetic coaptation body 200, as illustrated, that includes a prosthetic valve structured to enhance the function of the native heart valve, which is described in further detail with regard to FIGS. 2A, 2B, and 2C below. Preferably, prosthetic coaptation body 200 works together with the native leaflets to both provide a surface for the native leaflets to coapt and to provide a prosthetic valve in a conduit formed by prosthetic coaptation body 200. Unlike prior prosthetic valves that do not use the native leaflets (e.g., because they are cut away or pushed aside by the implant), prosthetic coaptation body 200 may use both the native leaflets and the prosthetic leaflets in the same native heart valve, thereby creating a "double-valve" configuration in the single heart valve. As shown in FIG. 1, support 300 may be structured to suspend and maintain prosthetic coaptation body 200 across the native heart valve once it has been positioned appropriately. As will be understood by one skilled in the art, the illustrated prosthetic coaptation body 200 may be substituted for other prosthetic devices designed to be implanted at a cardiac valve such as a plug/spacer device that coapts with native leaflets to reduce regurgitation such as that shown in U.S. Pat. No. 7,854,762 to Speziali.

As described above, distal, implantable portion 311 of support 300 may be coupled to prosthetic coaptation body 200. Proximal, delivery portion 310 of support 300, may be operatively coupled to actuator 108 and removeably coupled to distal, implantable portion 311 during delivery, such that proximal, delivery portion 310 may be manipulated by actuator 108 to accurately position prosthetic coaptation body 200 across the native valve. Support 300 may have a predefined bend to improve positioning of prosthetic coaptation body 200 across the native valve, as described in further detail below. For example, the bend may be predefined for a specific patient anatomy. Moreover, the predefine bend permits steering of the support from the predefined shape; this may have the effect of reducing stresses and strain on the elongated rail for long-term implant. In addition, heart valve therapeutic device 100 may include one or more radiopaque markers for in-vivo visualization during delivery of prosthetic coaptation body 200.

Figure 2C:
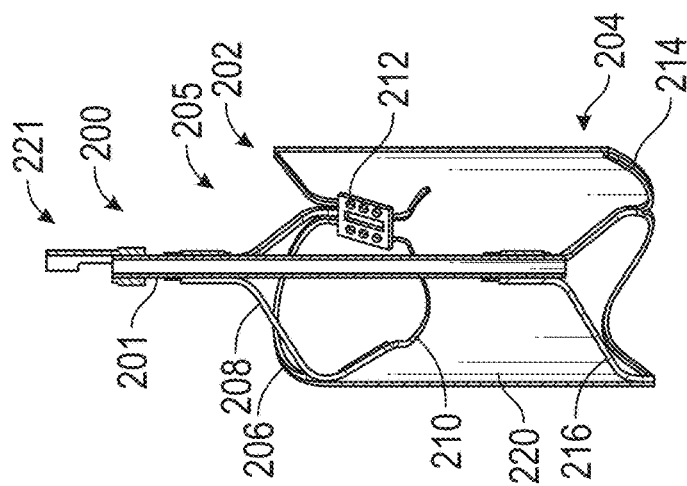
FIG. 2C is a cross-sectional view of the prosthetic device of FIGS. 2A and 2B.
Figure 2B:
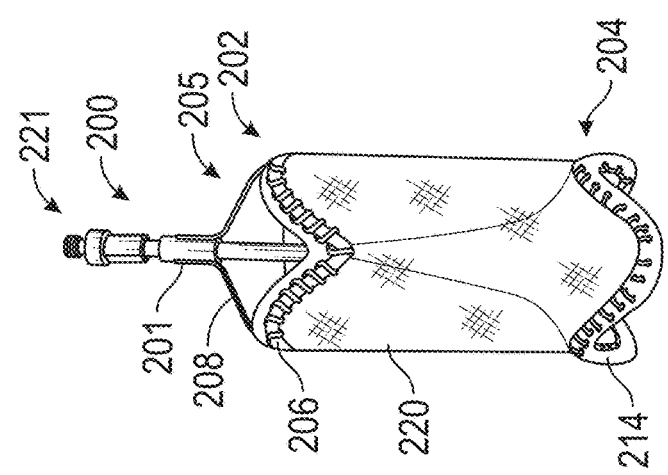
FIGS. 2A and 2B are perspective views of an exemplary prosthetic device of the heart valve therapeutic device of FIG. 1.
Figure 2A:
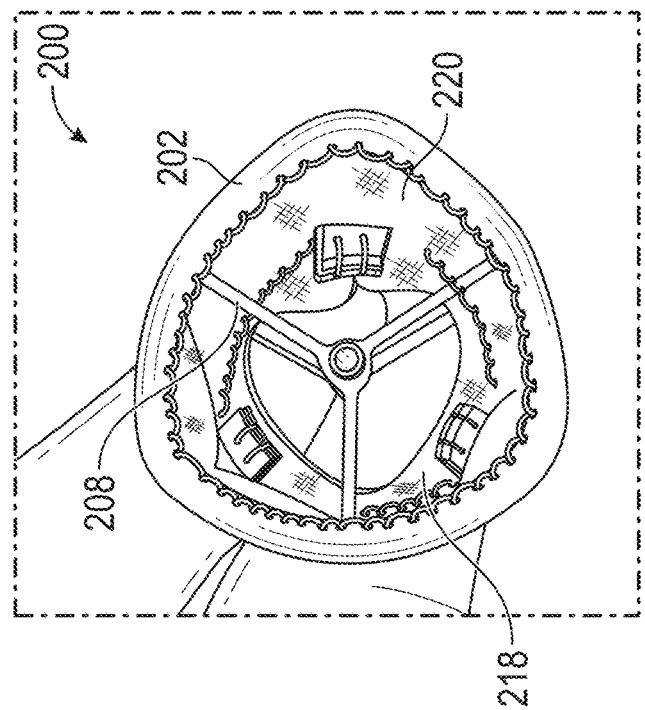

Referring now to FIGS. 2A, 2B and 2C, exemplary prosthetic coaptation body 200 of heart valve therapeutic device 100 is described. FIG. 2A shows prosthetic coaptation body 200 viewed from the distal end downward, FIG. 2B is a side view of prosthetic coaptation body 200, and FIG. 2C is a cross-sectional view of prosthetic coaptation body 200. Prosthetic coaptation body 200 preferably includes frame 205 having prosthetic leaflets 218 coupled thereto. Prosthetic leaflets 218 may be formed from natural tissue, such as bovine, equine, or porcine pericardial tissue, and/or manmade, synthetic material suitable for implantation such as ePTFE. Prosthetic coaptation body 200 may also contain one or more biocompatible materials, e.g., formed from the natural tissue and/or manmade material, coupled to frame 205 such as skirt 220. Prosthetic leaflets 218 and skirt 220 may be formed from the same material and may be integrally formed from a common piece of material or may be separate. Frame 205 further may include spine connector 221 for coupling with a support connector of support 300 as described in further detail below.

The shape of prosthetic coaptation body 200 is formed by frame 205, which is designed to transition from a contracted, delivery state to an expanded, deployed state and may be formed from shape memory material such as Nitinol. For example, frame 205 may form a conduit that, together with prosthetic leaflets 218 and the biocompatible material covering form a channel to allow blood to travel through prosthetic leaflets 218, when opened during the cardiac cycle, and through prosthetic coaptation body 200.

Skirt 220 may be a thin sheet of biocompatible material surrounding frame 205, extending from proximal ring 206 to distal ring 214 to form the outside surface of the conduit to which the native leaflets coapt when closed during the cardiac cycle. For example, skirt 220 may be sewn to proximal ring 206 and distal ring 214. Skirt 220 may be made of a rigid or compliant material. In some examples, skirt 220 expands and contracts responsive to pressure changes during the cardiac cycle. In this manner, skirt 220 may provide better coaptation with native leaflets. Accordingly, as prosthetic coaptation body 200 sits between the native tricuspid valve leaflets, it fills the regurgitant orifice area caused by right ventricular dilation. The native tricuspid valve leaflets seal against skirt 220 to prevent regurgitation between the native leaflets and prosthetic coaptation body 200 during systole. In addition, prosthetic leaflets 218 integrated within prosthetic coaptation body 200 supports flow during diastole. Prosthetic leaflets 218 may coapt onto the valve frame spine during systole to reduce regurgitation.

Referring now to FIGS. 2D, 2E, and 2F, frame 205 is described. Frame 205 may be made of metal, such as Nitinol or stainless steel. Frame 205 may be made of various components including wires, tubes, or flat strips. In a preferred embodiment, frame 205 is laser cut from one or more tubes of Nitinol. Frame 205 preferably includes spine 201, proximal portion 202 having proximal ring 206 and inner ring 210, and distal portion 204 having distal ring 214. Proximal ring 206 may be coupled to spine 201 via a plurality of proximal tethers 208 and step 203, as described in further detail below with regard to FIG. 2F, and distal ring 214 may be coupled to spine 201 via a plurality of distal tethers 216 and step 207. Alternatively, proximal tethers 208 and distal tethers 216 may be coupled directly to spine 201 without step 203 and step 207, respectively. Spine 201 may be an elongated shaft, e.g., formed from a metal tube such as stainless steel or Nitinol. As shown, spine 201 may extend generally through the middle of prosthetic coaptation body 200 to provide strength and support. In the illustrated example, spine 201 extends through prosthetic coaptation body 200 to the connection with distal ring 214 and proximally past the proximal end of prosthetic coaptation body to permit permanent, secure coupling between spine 201 and support 300. Preferably, proximal tethers 208 and distal tethers 216 are preferably formed of a rigid structure, and are compressible for delivery and may be self-expandable. Inner ring 210 may be positioned distal to and provide additional support to proximal ring 206, and may be coupled to proximal ring 206 via a plurality of slotted prosthetic leaflets anchors 212 having a plurality of suture eyelets to facilitate suturing of prosthetic leaflets 218 to frame 205. In a preferred embodiment, inner ring 210 has a diameter less than that of proximal ring 206 and may also have a diameter less than that of distal ring 214.

Proximal ring 202, distal ring 204, and inner ring 210 may have a generally-circular shape, but may be other shapes such as ovals or diamonds. As illustrated, proximal ring 206 may be scallop-shaped such that proximal ring 206 extends circumferentially from prosthetic leaflets anchor 212 proximally and radially outward, then distally and radially inward toward an adjacent prosthetic leaflets anchor 212. In a preferred embodiment, the proximal ends of proximal tethers 208 are coupled to spine 201 via step 203, and extend distally and radially outward such that the distal ends of proximal tethers 208 are coupled to prosthetic leaflets anchors 212. Accordingly, this configuration may optimize prosthetic leaflets shape, e.g., permits prosthetic leaflets anchors 212 to have a longer length with less angulation between spine 201 and proximal tethers 208, thereby reducing material strains and stresses during locking. Advantageously, the frame and ring structures are expected to maximize coaptation length while minimizing valve length and/or to create a coronary sinus-like region around the leaflet area (e.g., leaflet scallops) to maximize washout.

Inner ring 210 may extend circumferentially from prosthetic leaflets anchor 212 distally and radially outward, then proximally and radially inward toward an adjacent prosthetic leaflets anchor 212. Accordingly, inner ring 210 provides additional rigidity to proximal ring 206 and prosthetic leaflets anchors 212, which permits a reduction of overall size of frame 205, thereby reducing stress during collapse of frame 205, and improving durability of prosthetic coaptation body 200. As illustrated, distal ring 214 preferably has a sinusoidal wave shape around its circumference, such that distal tethers 216 are preferably coupled to distal ring 214 at a valley of the sinusoid. Distal ring 214 may have other oscillating shapes, which may be different in form to proximal ring 206. Thus, the proximal ends of distal tethers 216 are coupled to spine 201 via step 207, and extend distally and radially outward such that the distal ends of distal tethers 216 are coupled to the valley of distal ring 214.

As shown in FIG. 2F, the proximal ends of proximal tethers 208 may be coupled to spine 201 via step 203. Step 203 may be constructed from Nitinol and may be laser welded into place on spine 201, or alternatively, via molding or adhesive. Step 203 may have a wall thickness that is smaller, larger, or equal to the wall thickness of the cut tube from which frame 205 is formed. In addition, step 203 may include relief cuts to permit step 203 to be opened out onto spine 201 for optimal clearances for welding. Step 207 may be constructed similar to step 203.

Figure 3C:
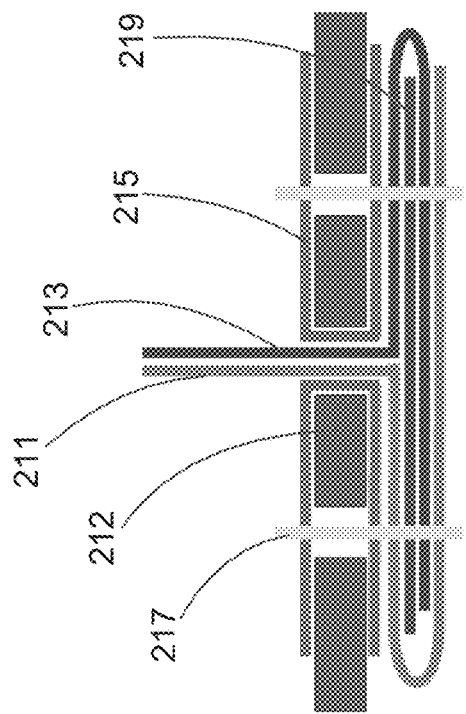
FIGS. 3A to 3D illustrates an exemplary method for suturing the prosthetic leaflets and skirt to the frame of the prosthetic device of FIGS. 2D and 2E.
Figure 3D:
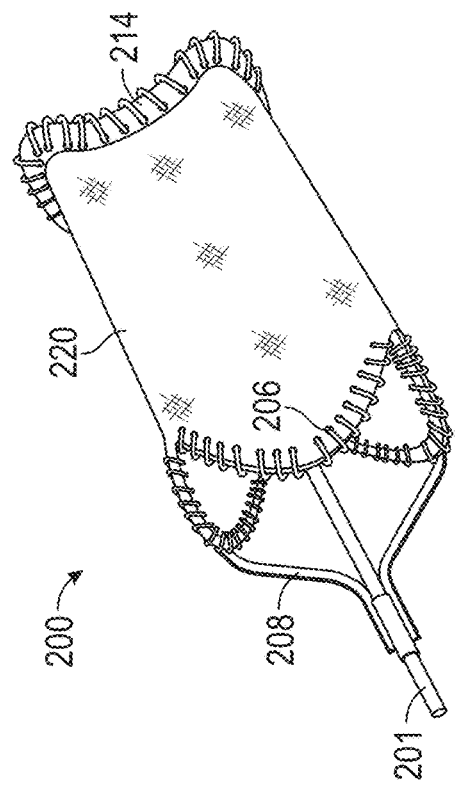
Figure 3A:
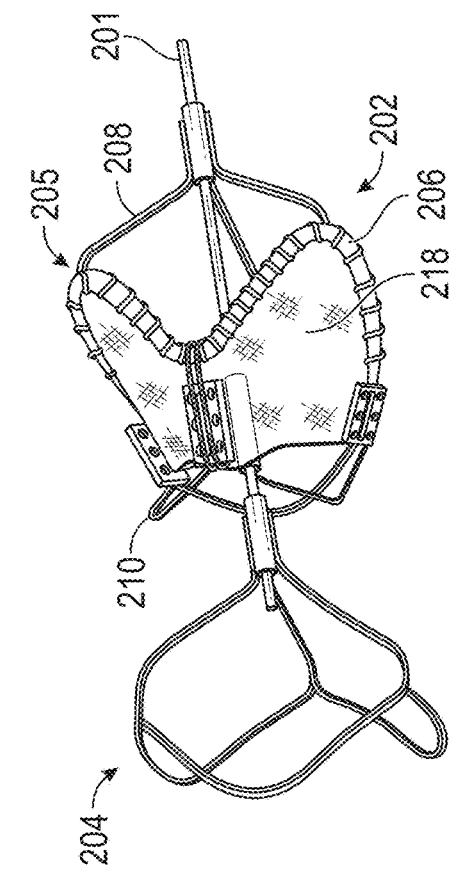
Figure 3B:
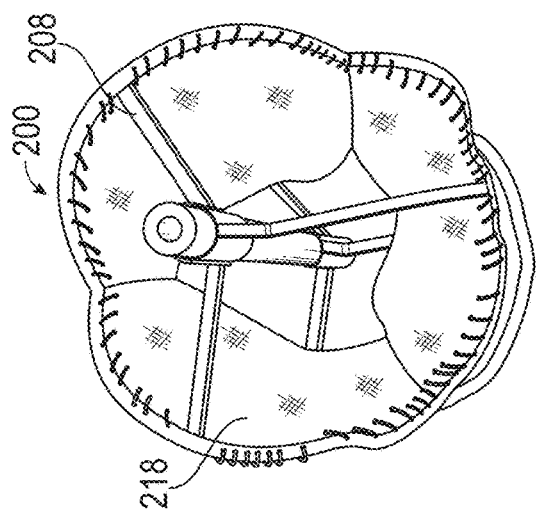

Referring now to FIGS. 3A to 3D, an exemplary method for attaching prosthetic leaflets 218 and skirt 220 to frame 205 is described. As shown in FIGS. 3A and 3B, prosthetic leaflets 218 may be coupled directly to proximal ring 206 and may also be coupled at their edges to prosthetic leaflets anchor 212. Coupling to prosthetic leaflets anchor 212 may improve coaptation of prosthetic leaflets 218. Accordingly, prosthetic leaflets 218 fill the space inside proximal ring 206 to form a prosthetic valve which allows blood to flow in the distal direction, but prevents blood from flowing in the proximal direction. Though three prosthetic leaflets 218 are shown in FIG. 3B, certain embodiments may have more or fewer prosthetic leaflets. Preferably, prosthetic leaflets 218 will match the number and arrangement of the native leaflets in the native valve.

As shown in FIG. 3C, commissure wrap 215 may be passed through an eyelet of prosthetic leaflets anchor 212, e.g., the longitudinal eyelet illustrated in FIG. 2D, such that commissure wrap 215 wraps around both surfaces of prosthetic leaflets anchor 212. First leaflet 211 and second leaflet 213 may be passed through the same eyelet of prosthetic leaflets anchor 212, e.g., through commissure wrap 215, and wrapped in an over-lapping fashion over leaflet pledget 219. Leaflet pledget 219 increases stability of prosthetic leaflets 218 and prevents pullout of first and second leaflets 211 and 213. Commissure wrap 215 and leaflet pledget 219 may be made of a biocompatible polymer, e.g., pericardium, or another fabric known in the art. Accordingly, commissure wrap 215 may protect leaflet commissures from damage resulting with contact with prosthetic leaflets anchor 212. Moreover, one or more sutures 217 may be used to sew prosthetic leaflets 218 to prosthetic leaflets anchor 212 and proximal ring 206 in a commissure suture pattern as shown in FIGS. 3A and 3B. As shown in FIG. 3D, skirt 220 may be sewn in a commissure suture pattern to both proximal ring 206 and distal ring 214 of frame 205, to ensure complete sealing of skirt 220 and prosthetic leaflets 218, and to form the outer surface of prosthetic coaptation body 200. Moreover, prosthetic leaflets anchor 212 may be tapered inward to avoid contact between prosthetic leaflets anchor 212 and skirt 220. In addition, as shown in FIG. 2A, an addition wrap, e.g., pericardium, may be sutured to cover distal ring 214 to provide a more atraumatic surface if it contacts the surrounding anatomy.

Figure 4A:
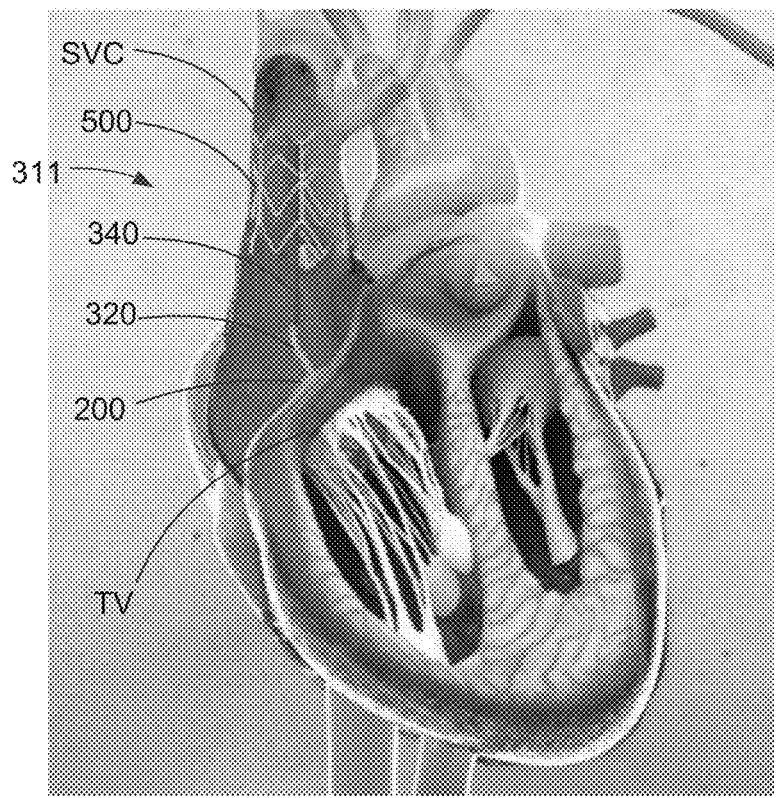
FIG. 4A illustrates the implantable portion of the heart valve therapeutic device of FIG. 1 implanted at a native heart valve.
Figure 4B:
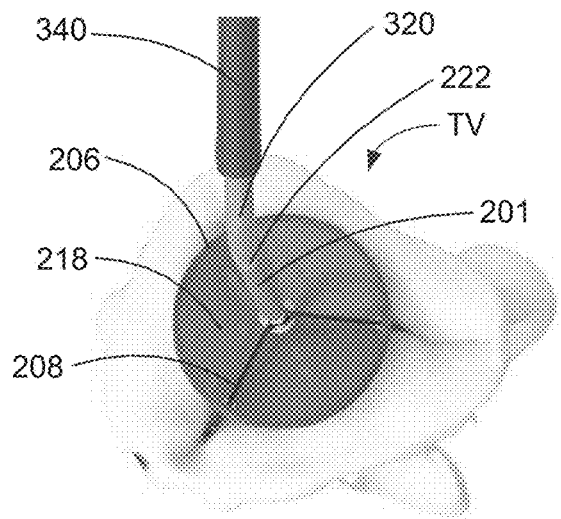
FIGS. 4B and 4C illustrate the heart valve therapeutic device at a native heart valve in a closed and open configuration, respectively.
Figure 4C:
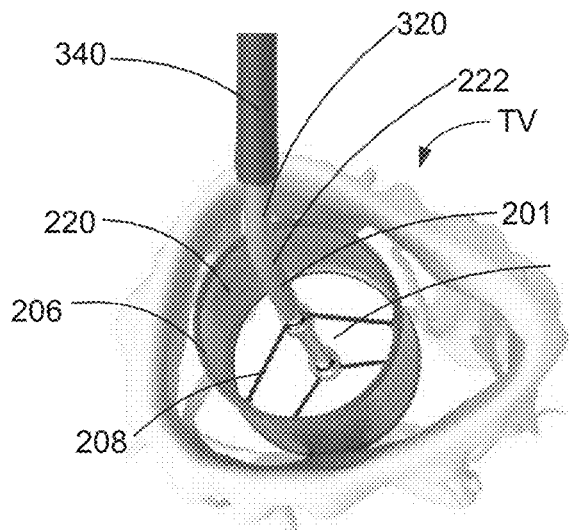

FIGS. 4A to 4C illustrate prosthetic coaptation body 200 implanted at a native heart valve. As shown in FIG. 4A, prosthetic coaptation body 200 is suspended within the native heart valve via distal, implantable portion 311 of support 300 and anchor 500. For example, anchor 500 may be implanted within SVC such that prosthetic coaptation body 200 is suspended within tricuspid valve TV via body support catheter 320, as described in further detail below. FIG. 4B shows prosthetic coaptation body 200 suspended within the tricuspid valve TV during systole whereby prosthetic leaflets 218 are in a closed configuration and the native valve leaflets are sealed against the outer surface of prosthetic coaptation body 200 to prevent regurgitation between the native leaflets and prosthetic coaptation body 200. FIG. 4C shows prosthetic coaptation body 200 suspended within the tricuspid valve TV during diastole whereby prosthetic leaflets 218 and the native valve leaflets are in an open configuration, thereby permitting flow therethrough. Advantageously, the prosthetic device sits across the native valve and contacts the native leaflets when they seal during systole, but the prosthetic device need not be in contact with the annulus. The anchoring system sits above the prosthetic device in the atrium and may extend up to the stent in the SVC or, alternatively, the IVC.

Figure 5A:
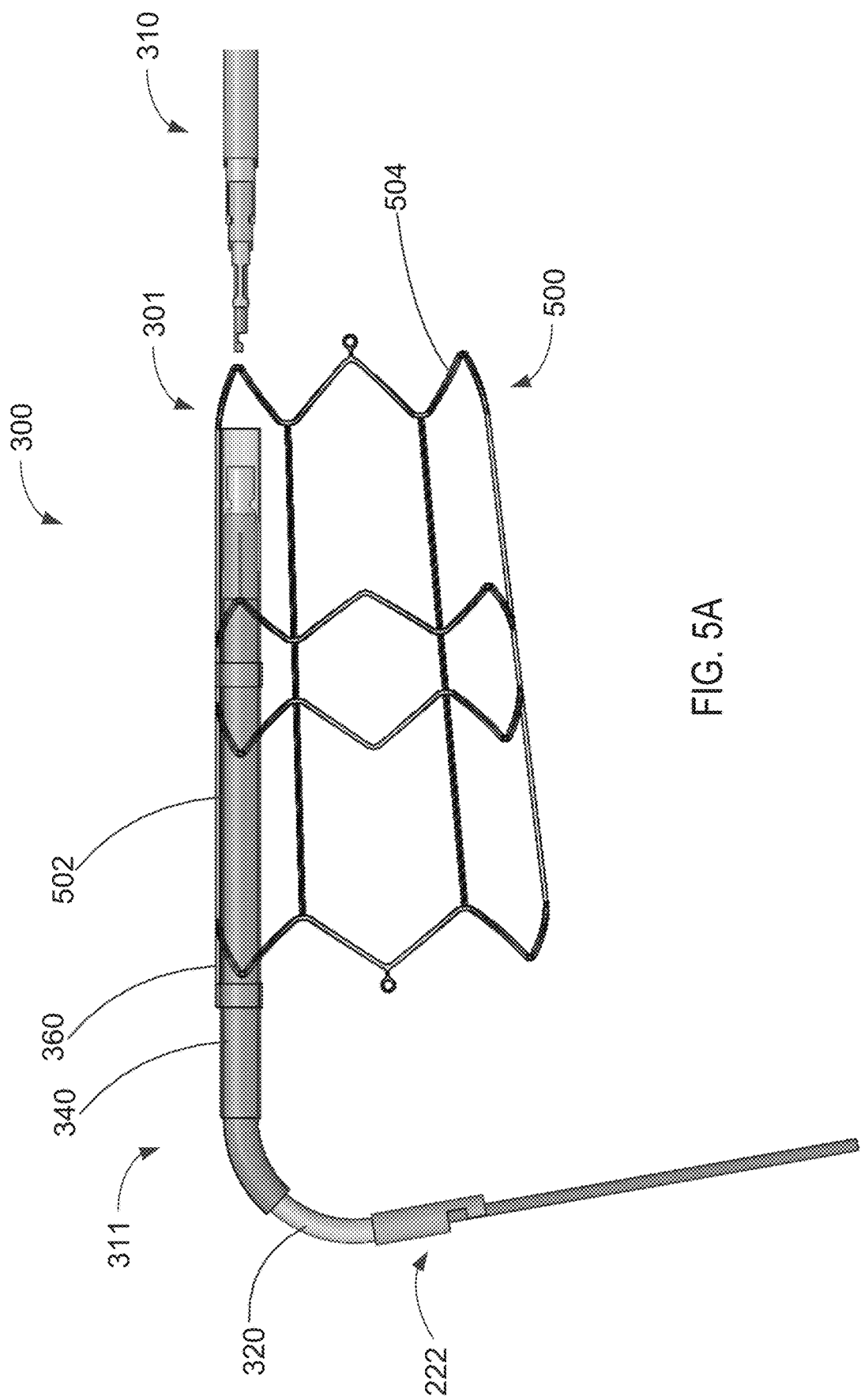
FIGS. 5A and 5B illustrate exemplary detachable supports constructed in accordance with the principles of the present invention.
Figure 5B:
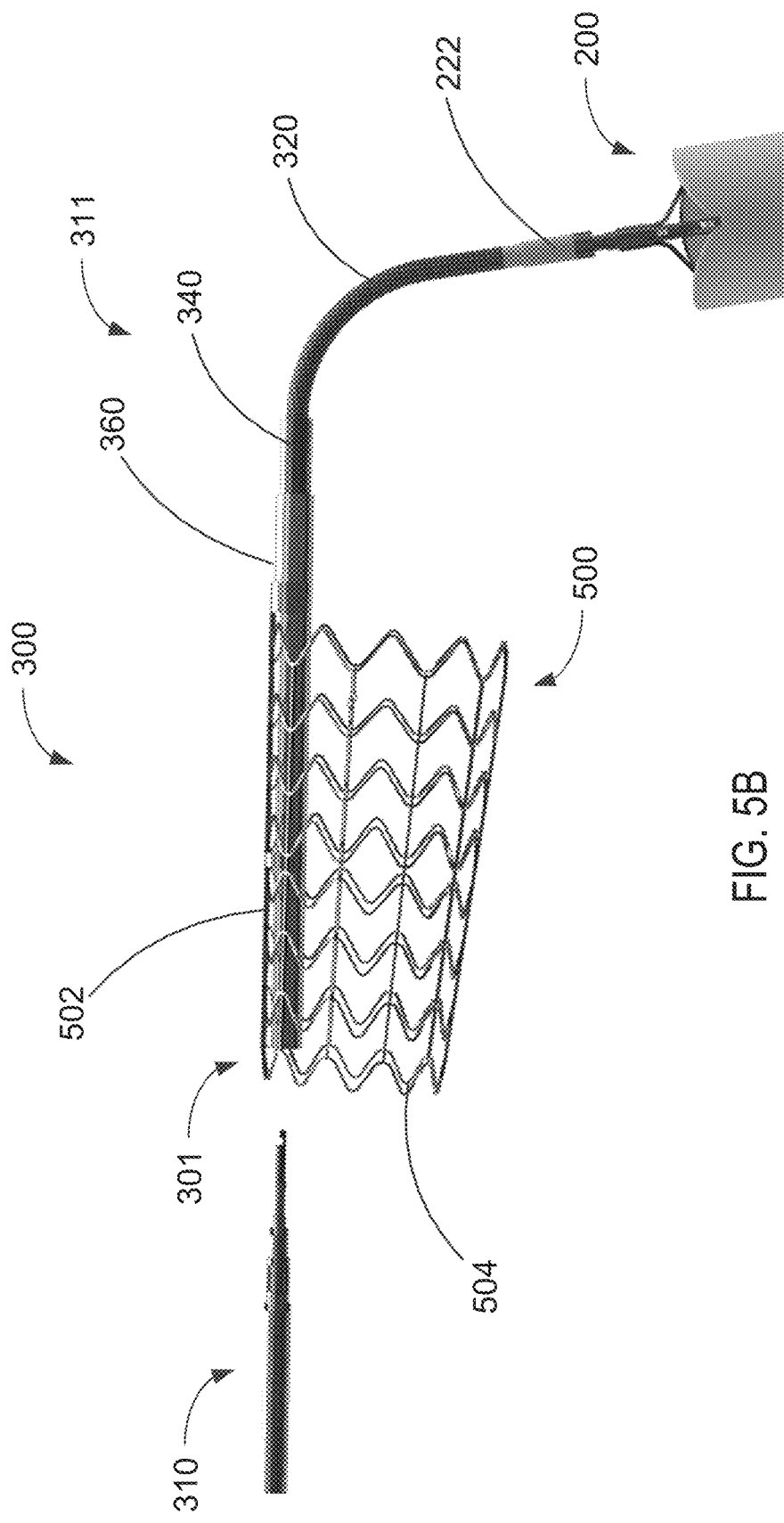

Referring now to FIGS. 5A and 5B, support 300 for delivering and implanting the prosthetic coaptation body is described. Support 300 includes an elongated shaft including proximal, delivery portion 310 and distal, implantable portion 311, and may be steered and manipulated via actuator 108 (see FIG. 1). Proximal, delivery portion 310 may be removeably coupled to distal, implantable portion 311 at detachment area 301 during delivery of prosthetic coaptation body 200, and proximal, delivery portion 310 may be decoupled from distal, implantable portion 311 to thereby implant distal, implantable portion 311 and prosthetic coaptation body 200 in the desired location within the patient. Accordingly, proximal, delivery portion 310 may be removed from the patient, while distal, implantable portion 311 and prosthetic coaptation body 200 remain fully implanted.

As shown in FIGS. 5A and 5B, distal, implantable portion 311 of support 300 includes valve connection area 222 for coupling with prosthetic coaptation body 200 (e.g., via spine connector 221), anchor 500 including stent 504 coupled to anchor tube 360 via anchor support 502, and a plurality of catheters including body support catheter 320 and shaping catheter 340 for maneuvering and implanting prosthetic coaptation body 200, as described in further detail below. FIG. 5A shows an exemplary tapered stent design and FIG. 5B shows another exemplary stent design.

Figure 6A:
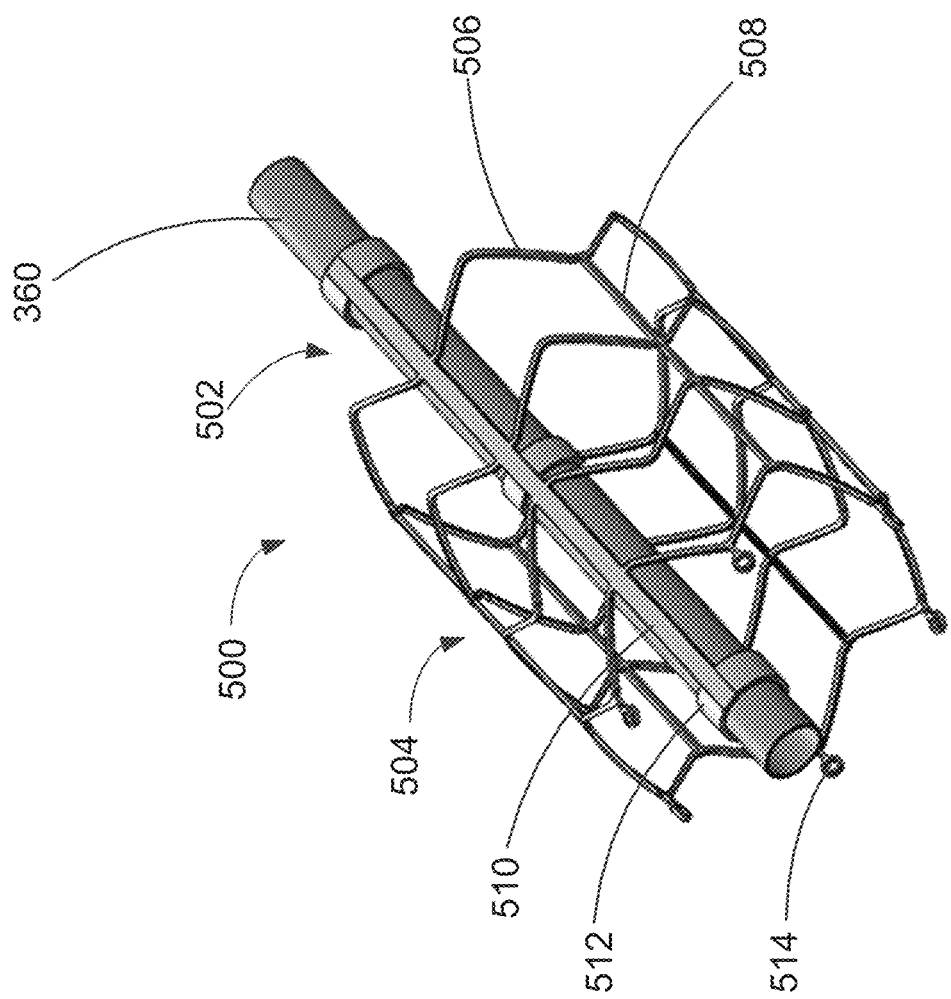
FIG. 6A is a perspective view of an exemplary anchor and anchor tube of the detachable support of FIGS. 5A and 5B.

Referring now to FIGS. 6A to 6G, anchor 500 is described. As shown in FIG. 6A, anchor 500 includes stent 504 coupled to anchor tube 360 via anchor support 502. Anchor tube 360 has a lumen sized and shaped to receive shaping catheter 340 therethrough. Anchor tube 360 may be coupled to one side of stent 504 to stabilize distal, implantable portion 311 of support 300 and bias it to one side of the blood vessel. For example, stent 504 may include longitudinal stent spine 510. Stent spine 510 may be formed with stent 504 as a single component, or may be a separate component affixed to stent 504. Stent spine 510 may be coupled to one or more anchor tube cuffs 512 for clamping stent 504 to anchor tube 360. For example, anchor tube cuffs 512 may have a lumen sized and shaped to receive anchor tube 360 therethrough. Anchor tube cuffs 512 may be coupled to anchor tube 360 such that relative movement between anchor tube cuffs 512 and anchor tube 360 is prevented. Although only three anchor tube cuffs 512 are illustrated in FIG. 6A, a person having ordinary skill in the art would understand that anchor tube cuffs 512 may include less than three cuffs, e.g., one or two cuffs, or more than three cuffs, e.g., four, five, six cuffs or more as necessary.

Referring now to FIGS. 6B to 6E, an exemplary anchor tube is described. Referring to FIG. 6B, the anchor tube is shown with components separated for clarity. As shown in FIG. 6B, support 300 may include anchor tube 360 having anchor tube distal portion 380 at distal, implantable portion 311 of support 300, and anchor tube proximal portion 382 at proximal, delivery portion 310 of support 300. Anchor tube 360 may extend from actuator 108 toward prosthetic coaptation body 200 where it may be coupled to stent 504. Anchor tube proximal portion 382 may be attached to anchor tube distal portion 380 via anchor tube connection 384 during delivery. For example, anchor tube distal portion 380 may have distal anchor tube connection portion 381 having a first geometry, and anchor tube connection 384 may have distal anchor tube interlinking portion 385 having a second geometry corresponding with the first geometry of distal anchor tube connection portion 381 such that, in the delivery configuration, distal anchor tube connection portion 381 engages with distal anchor tube interlinking portion 385. In addition, anchor tube proximal portion 382 may have proximal anchor tube connection portion 383 having a third geometry, and anchor tube connection 384 may have proximal anchor tube interlinking portion 387 having a fourth geometry corresponding with the third geometry of proximal anchor tube connection portion 383 such that, in the delivery configuration, proximal anchor tube connection portion 383 engages with proximal anchor tube interlinking portion 387. As shown in FIG. 6B, anchor tube 360 further may include anchor tube sleeve 390, which may be slidably disposed over at least anchor tube proximal portion 382 and anchor tube connection 384. FIG. 6C illustrates the components of anchor tube 360 in an engaged delivery position, without anchor tube sleeve 390 for clarity.

Figure 6D:
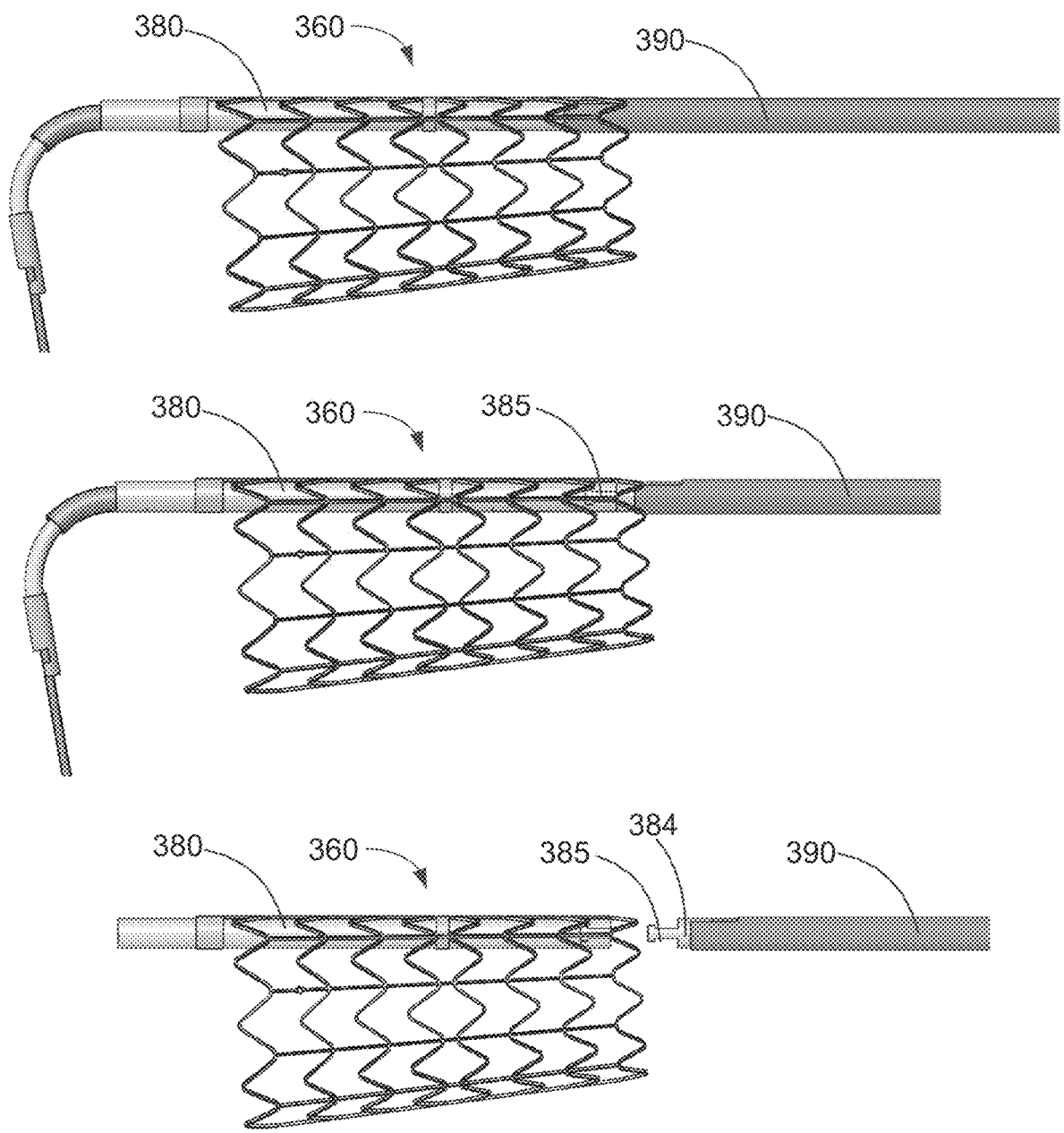
FIGS. 6D and 6E illustrate the anchor tube in an engaged configuration suitable for delivering the prosthetic device to the cardiac valve and a disengaged configuration where the distal, implantable portion remains implanted and the proximal, delivery portion can be removed from the patient.
Figure 6E:
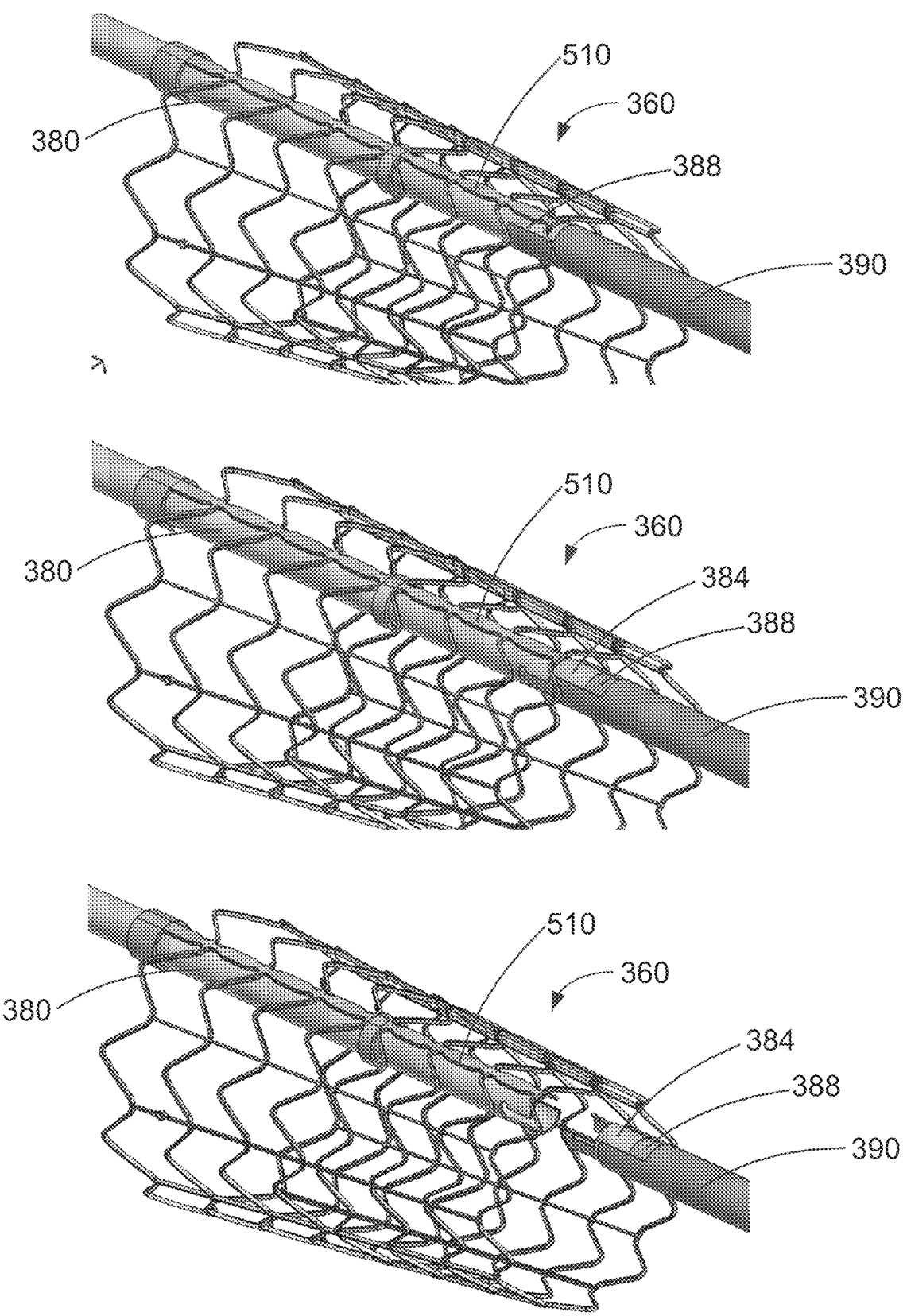

Referring now to FIGS. 6D and 6E, an exemplary method for detaching the proximal components of anchor tube 360 from anchor tube distal portion 380 such that anchor tube distal portion 380 may be implanted within the patient is described. As shown in the top illustration of FIG. 6D, in the delivery configuration, anchor tube sleeve 390 is disposed over anchor tube proximal portion 382 and anchor tube connection 384 while anchor tube connection 384 is engaged with anchor tube distal portion 380. Next, as shown in the middle illustration of FIG. 6D, anchor tube sleeve 390 may be retracted proximally responsive to actuation of actuator 108, e.g., by actuating an interface on actuator 108, to expose distal anchor tube interlinking portion 385 of anchor tube connection 384. Distal anchor tube interlinking portion 385 may self-expand from a collapsed delivery state within anchor tube sleeve 390 to an expanded state upon exposure from anchor tube sleeve 390, such that distal anchor tube interlinking portion 385 disengages with anchor tube distal portion 380. As shown in the bottom illustration of FIG. 6D, anchor tube proximal portion 382, anchor tube connection 384, and anchor tube sleeve 390 may be removed from the patient while anchor tube distal portion 380 remains implanted within the patient. Preferably, retraction of anchor tube sleeve 390 is limited such that anchor tube sleeve 390 remains disposed over proximal anchor tube interlinking portion 387 and anchor tube proximal portion 382.

FIG. 6E illustrates a perspective view of the exemplary method of FIG. 6D for detaching the proximal components of anchor tube 360 from anchor tube distal portion 380. As shown in FIG. 6E, the distal end of anchor tube sleeve 390 may include opening 388, such that when anchor tube sleeve 390 is disposed over anchor tube connection 384 in the delivery configuration, anchor tube sleeve 390 avoids collision with the stent spine of the stent of anchor 500.

Referring now to FIG. 6F, an exemplary stent is described. As shown in FIG. 6F, stent 504 may be formed by a plurality of sinusoidal or zig-zag or otherwise oscillating circumferential pattern of struts 506, interconnected via a plurality of longitudinal struts 508. One of the plurality of longitudinal struts 508 may be stent spine 510, or alternatively, stent spine 510 may be affixed to one of the plurality of longitudinal struts 508. Although only four circumferential struts 506 are illustrated in FIG. 6F, a person having ordinary skill in the art would understand that stent 504 may include less than four circumferential struts, e.g., two or three circumferential struts, or more than four circumferential struts, e.g., five, six, seven, eight circumferential struts or more as necessary. In accordance with one aspect of the present invention, the pattern of struts 596 and longitudinal struts 508 are formed such that the length of stent 504 may be the same in its collapsed, delivery state within the delivery sheath, as in its expanded, deployed state.

Stent 504 may be self-expandable such that stent 504 transitions from a collapsed, delivery state within a delivery sheath, to an expanded, deployed state within the target blood vessel for anchoring support 300. Stent 504 may have a variable stiffness around its circumference and along its length. For example, the width of the frame forming circumferential struts 506, the longitudinal length of a strut of the plurality of circumferential struts 506, and/or the radius of curvature of the plurality of circumferential struts 506 may be varied to achieve the desired stiffness of stent 504. In addition, stent 504 may have a plurality of loops for radiopaque markers, e.g., gold markers 514, to assist in visualization during delivery of prosthetic coaptation body 200. As shown in FIG. 6F, proximal end 501 of stent 504 may have a smaller diameter than distal end 503 of stent 504. This tapered configuration may improve anchoring within a patient's blood vessel. Moreover, stent 504 may have a plurality of barbs extending from its outer surface to improve migration resistance. In a further embodiment the stent may have a variable diameter along its length to improve anchoring.

Figure 6H:
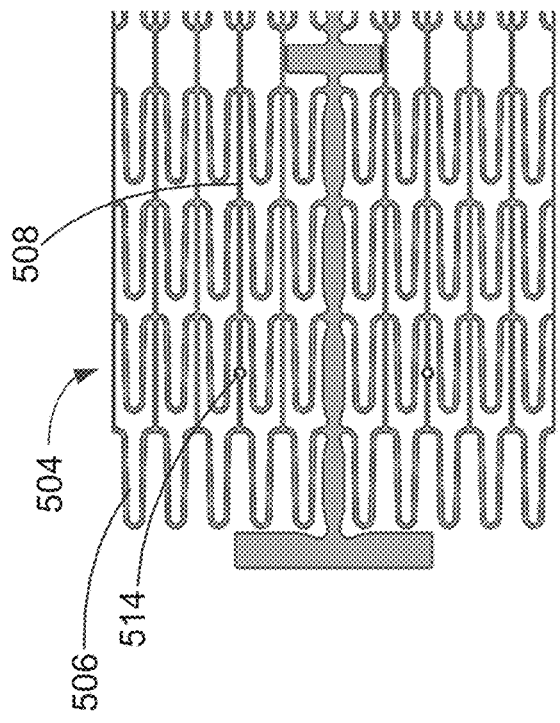
FIGS. 6G to 6J illustrate various configurations of frames for the stent of the anchor.
Figure 6J:
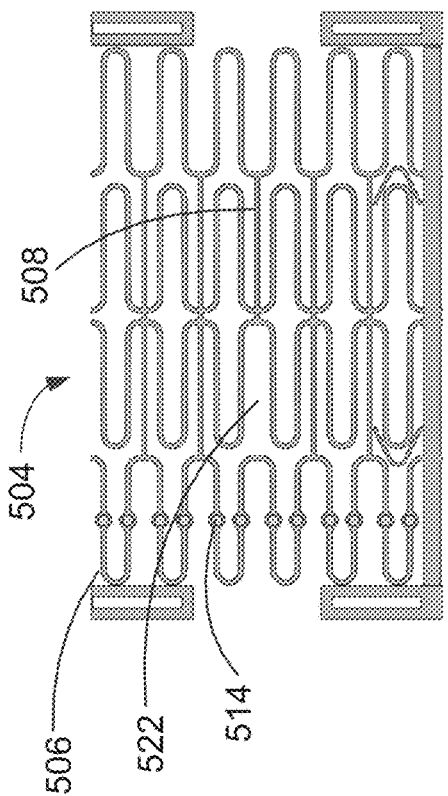
Figure 6G:
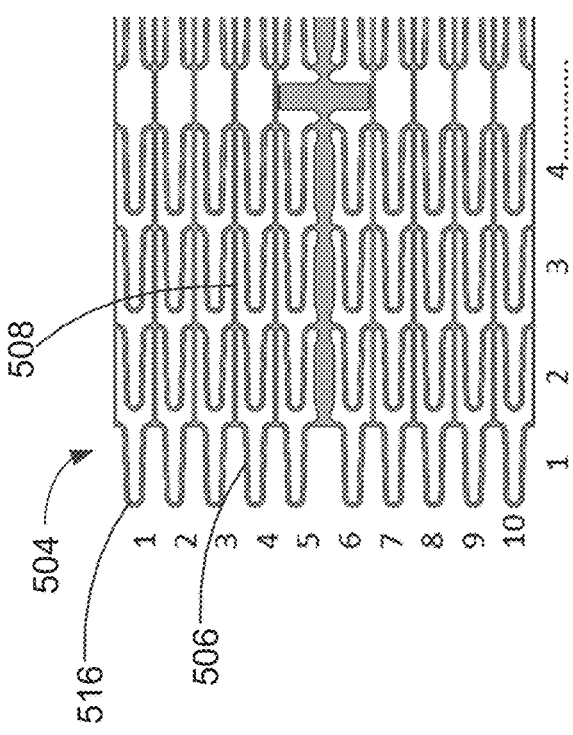
Figure 6I:
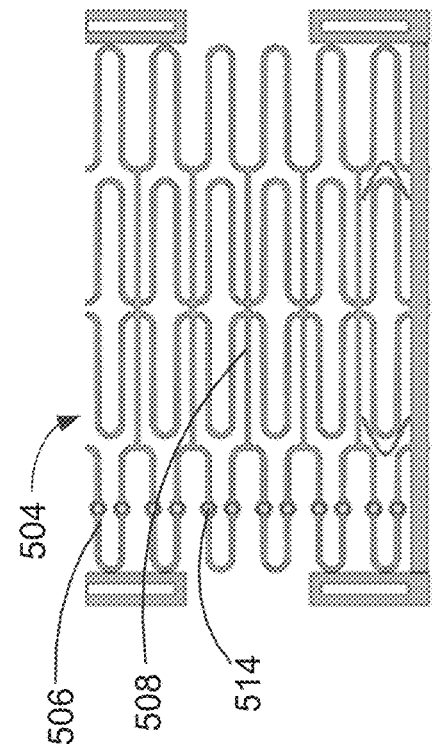

FIGS. 6G to 6J illustrate various configurations of the frame of the stent of the anchor. As shown in FIG. 6G, circumferential struts 506 of stent 504 may include N numbers of sinusoids 516 along its circumferential length, and stent 504 may include N number of circumferential struts 506 along its longitudinal length. As shown in FIG. 6H, markers 514 may be positioned along plurality of longitudinal struts 508. Alternatively, as shown in FIG. 6I, markers 514 may be positioned along plurality of circumferential struts 506. As shown in FIG. 6J, longitudinal struts 508 may not extend across every circumferential struts 506, thereby creating space 522 without a longitudinal strut extending thereacross, which may improve distribution of strain on stent 504. In some embodiments, stent 504 may not have any longitudinal struts.

Figure 6K:
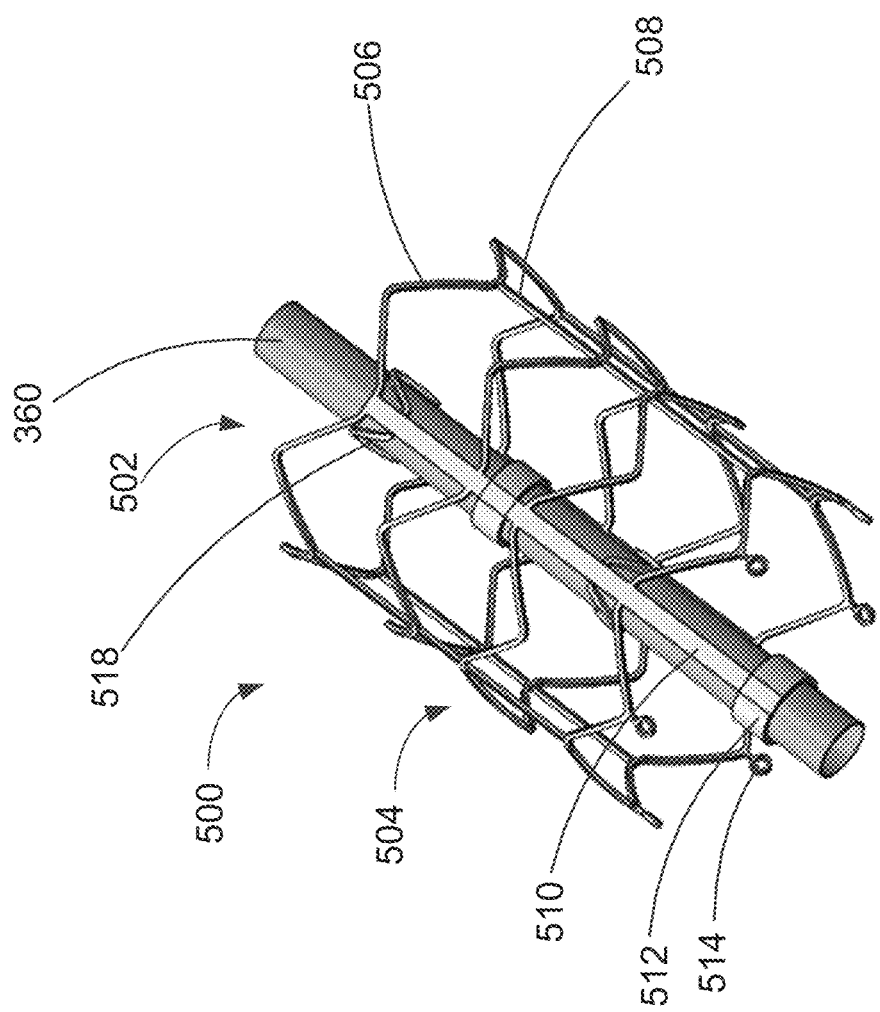
FIG. 6K is a perspective view of another exemplary anchor.

FIG. 6K illustrates anchor 500 having an alternative coupling mechanism between stent spine 510 and anchor tube 360. For example, anchor 500 further may include a plurality of v-shaped cuffs 518 for clamping stent spine 510 to anchor tube 360. As shown in FIG. 6K, anchor 500 may include v-shaped cuffs 518 in addition to anchor tube cuffs 512. Alternatively, anchor 500 may only include v-shaped cuffs 518 and no anchor tube cuffs 512. Moreover, any number of v-shaped cuffs 518 and/or anchor tube cuffs 512 may be used to stabilize stent 504 relative to anchor tube 360.

Referring now to FIGS. 7A to 12F, a plurality of catheters that may be included in support 300 are described. As shown in FIG. 7A, support 300 may include an elongated rail having elongated rail distal portion 302 at distal, implantable portion 311 of support 300, and elongated rail proximal portion 304 at proximal, delivery portion 310 of support 300. The elongated rail may be solid or it may have a tube shape. The elongated rail may extend from actuator 108 to prosthetic coaptation body 200, and may have a pre-formed bend area to facilitate delivery of prosthetic coaptation body 200 to the native heart valve. In addition, the pre-formed bend may reduce the stress required to position prosthetic coaptation body 200 during delivery. For example, the elongated rail may be an elongated shaft made of metal (e.g., Nitinol) that is preformed to a predetermined angle (e.g., 50-150 degree bend, 100 degree bend). The body support catheter may be coaxial to the preformed rail and the shaping catheter and may be attached to the prosthetic device to facilitate telescoping of the prosthetic device beyond the bend. The shaping catheter may be coaxial to the preformed rail and the body support catheter. The distal end of the shaping catheter may have a collar that is used to bend and straighten the preformed rail based on the relative axial position between the two responsive to actuation at the handle. For example, as the shaping catheter is advanced distally over the preformed bend of the elongated rail, the elongated rail straightens, and as the shaping catheter is retracted proximally relative to the elongated rail, the elongated rail returns to its natural state with the preformed bend. As will be understood by a person having ordinary skill in the art, the rail may be moved while the shaping catheter remains stationary within the patient to bend and straighten the preformed rail.

The prosthetic device may be secured on the distal end of the anchor system using the implantable support catheter connected to a Nitinol Stent with a disconnectable proximal section to support delivery. The support catheter may be used to deliver and adjust and finally stabilize the position the prosthetic device across the native cardiac valve. The anchor system may be used to deploy, position, and support the prosthetic device, attached to the distal end. Once the prosthetic device has been positioned, a self-expanding Nitinol stent may be deployed in the tissue (e.g., SVC or IVC) which may be attached to the support catheter. The position of the prosthetic device can be further adjusted after the stent is deployed. The stent may be supported by the anchor tube component of the support catheter. The support catheter may have a steerable distal portion that is controlled by the handle to ensure optimal positioning. This can avoid hooks, screws or clamps in the thin, frail structures of the dilated right heart and allows the system to accommodate cardiac and respiratory motion. After deployment and final positioning of the prosthetic device, the position is locked and the delivery section of the anchor system, proximal to the stent, is disconnected and removed.

Advantageously, the anchor system can allow for deflection from a straight configuration through 100 degrees of angulation so that the prosthetic device can be positioned coaxial to the tricuspid annulus; telescoping of the prosthetic device down, towards the apex of the ventricle, into the tricuspid annulus so that it is positioned properly between the tricuspid valve leaflets; extension and rotation of the position of the bend relative to the stent so that the prosthetic device can cross the tricuspid valve perpendicular to it, and so the clinician may freely position the stent to a preferred location; stabilizing of the prosthetic device in position by anchoring against the tissue (e.g., wall of a blood vessel such as the SVC or IVC); fixing the selected position, angulation and telescoping, of the prosthetic device. The positioning of the prosthetic device is helped by the native valve leaflets which naturally direct and center it within the central gap of the leaflets. The distal portion of the anchor system has sufficient stiffness to maintain the prosthetic device in position during the cardiac cycle, as well as sufficient flexibility to permit the prosthetic device to "self-center" within the native valve during systole. This distal portion of the anchor system may be connected to support the prosthetic device and stabilized in the SVC by the stent anchor. The sterilization process for the anchor system and its accessories may be Ethylene Oxide (ETO) or radiation sterilized. This sterilization process is standard for catheter systems.

Figure 8A:
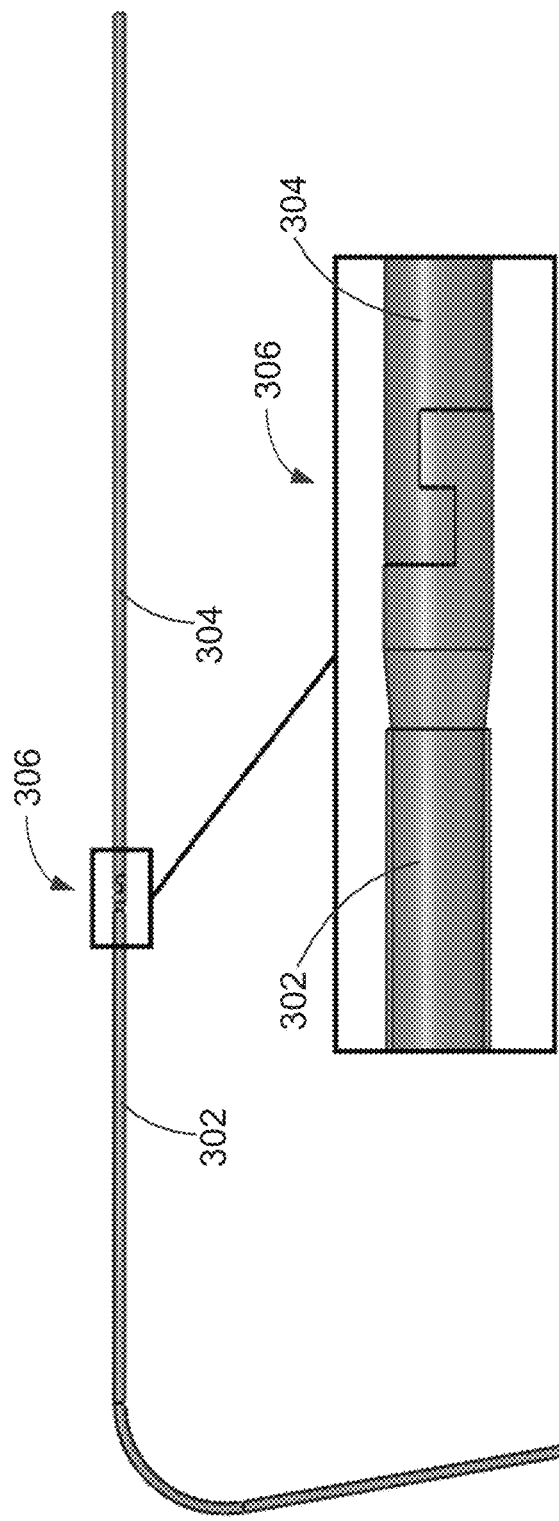
FIGS. 8A and 8B illustrate the elongated rail of FIG. 7A in an engaged and a disengaged configuration, respectively.
Figure 8B:
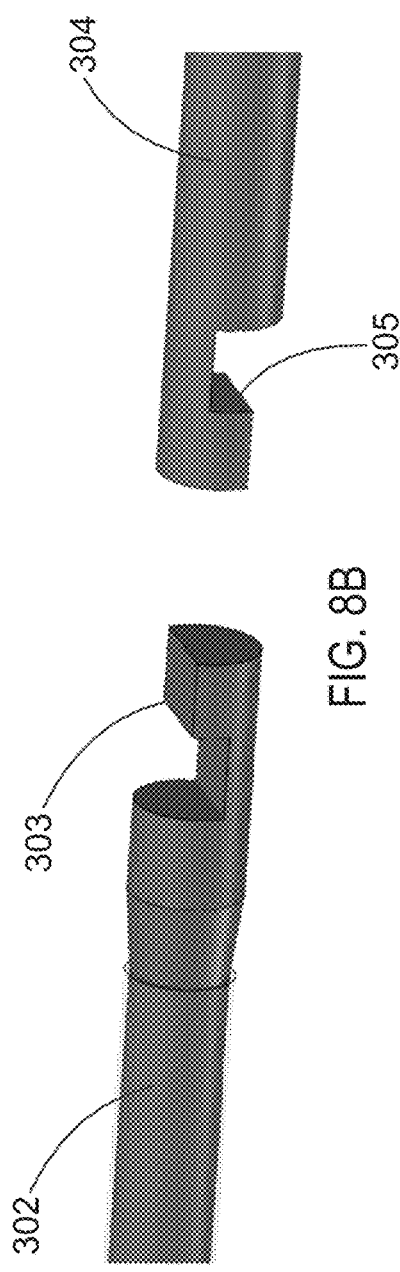

As shown in FIGS. 8A and 8B, elongated rail distal portion 302 and elongated rail proximal portion 304 may be removably attached together at elongated rail detachment area 306. For example, elongated rail distal portion 302 may have first geometry 303, and elongated rail proximal portion 304 may have second geometry 305 corresponding to first geometry 303 such that elongated rail distal portion 302 may engage with elongated rail proximal portion 304 during delivery as shown in FIG. 8A. For example, first and second geometries 303, 305 may be notches and teeth, wherein a tooth of first geometry 303 fits in the notch of second geometry 305 and a tooth of second geometry 305 fits in the notch of first geometry 303, thereby attaching the elongated rail during delivery. Elongated rail distal portion 302 may be disengaged from elongated rail proximal portion 304 for implantation of elongated rail distal portion 302 as shown in FIG. 8B. For example, the distal and proximal portions of the elongated rail may detach responsive to actuation at the handle. As explained below, the body support catheter may be used to maintain the engagement between the distal and proximal portions of the elongated rail and the elongated rail detaches responsive to detachment of the body support catheter.

Referring back to FIGS. 7B to 7E, support 300 may include a body support catheter having body support catheter distal portion 320 and body support catheter lock 330 at distal, implantable portion 311 of support 300, and body support catheter proximal portion 326, body support catheter connection 324, and body support catheter pusher 332 at proximal, delivery portion 310 of support 300. The body support catheter may extend from actuator 108 to prosthetic coaptation body 200.

Figure 9A:
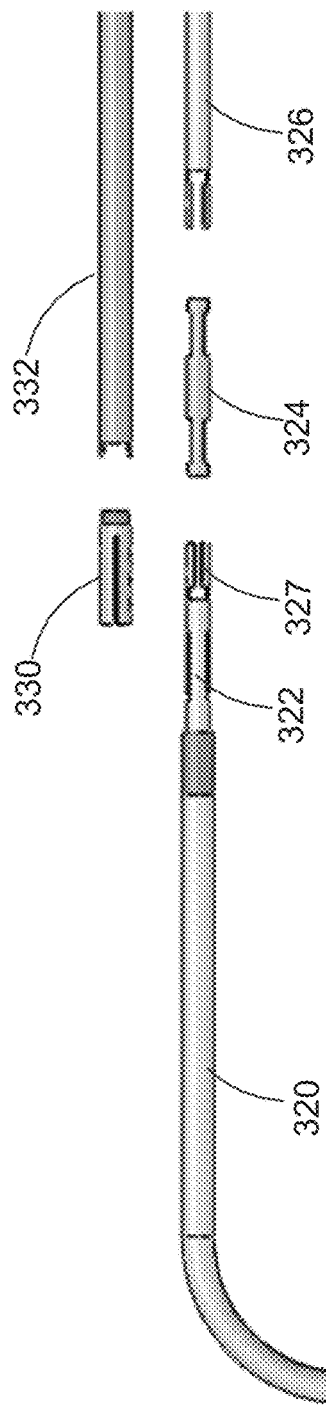
FIGS. 9A and 9B are perspective views of exemplary components of the body support catheter of FIGS. 7B to 7E.
Figure 9B:
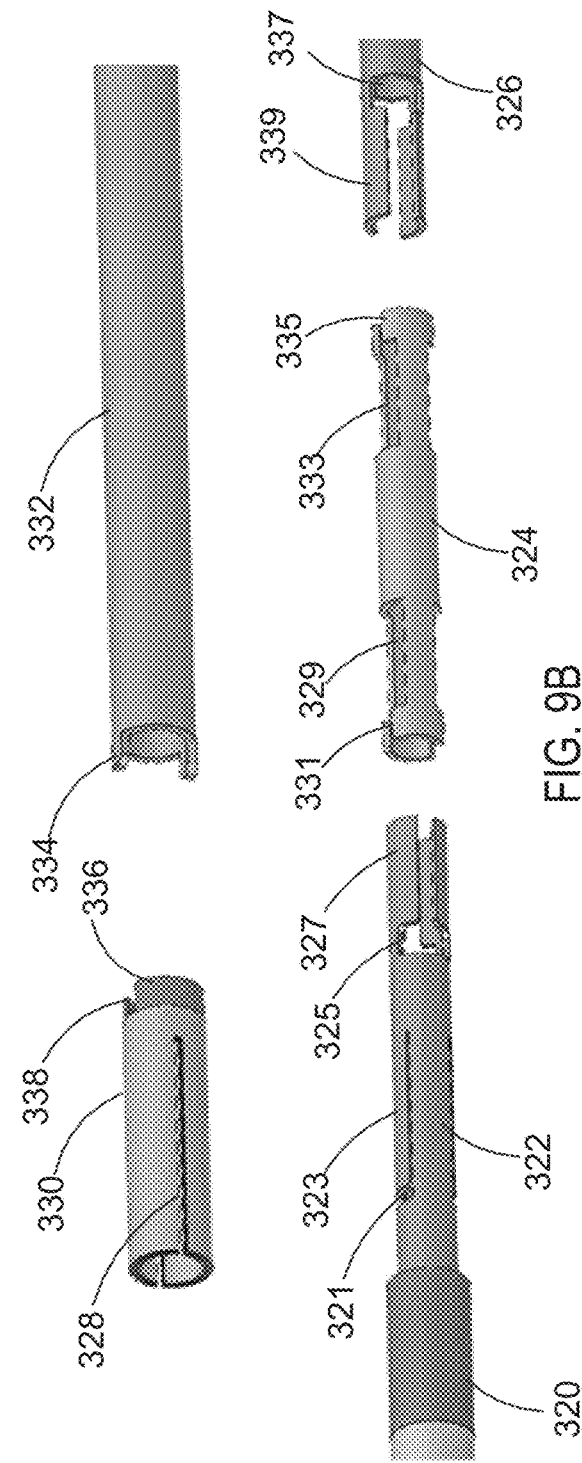

Referring now to FIGS. 9A and 9B, the body support catheter is shown with components separated for clarity. Body support catheter distal portion 320, body support catheter connection 324, and body support catheter pusher 332 have a lumen sized and shaped to receive the elongated rail therethrough. The distal end of body support catheter distal portion 320 may include a support connector for coupling with prosthetic coaptation body 200, and the proximal end of body support catheter distal portion 320 may include distal body support locking portion 322 and distal body support connection portion 327. Distal body support locking portion 322 and distal body support connection portion 327 may be formed of a single piece and may have an outer diameter that is smaller than the outer diameter of body support catheter distal portion 320. Alternatively, distal body support locking portion 322 and distal body support connection portion 327 may be separate components that are conjoined together. The tube formed by distal body support locking portion 322 and distal body support connection portion 327 may extend at least partially through the lumen of body support catheter distal portion 320. Accordingly, distal body support locking portion 322 and distal body support connection portion 327 may have a lumen sized and shaped to receive the elongated rail therethrough.

As shown in FIG. 9B, distal body support locking portion 322 may include slit 321 forming interference locking portion 323. For example, slit 321 may be U-shaped, which defines the shape of interference locking portion 323. In accordance with some embodiments, interference locking portion 323 may be a wedged portion that has a thickness that is greater than the thickness of distal body support locking portion 322 and distal body support connection portion 327, such that the wedged portion may be pushed radially inward to lock body support catheter distal portion 320 to elongated rail distal portion 302, as described in further detail below. In some embodiments, a separate wedged material may be disposed under interference locking portion 323 of distal body support locking portion 322, such that when interference locking portion 32 is pushed radially inward, the separate wedged material lock body support catheter distal portion 320 to elongated rail distal portion 302. Distal body support connection portion 327 may include opening 325, e.g., a T-shaped opening, sized and shaped to interlink with body support catheter connection 324.

Body support catheter connection 324 may include distal body support interlinking portion 331 defined by opening 329 and optional proximal body support interlinking portion 335 defined by opening 333. Distal body support interlinking portion 331 may be biased radially outward, and may transition from the expanded state to a collapsed state upon application of a radially inward force, as described in further detail below. Moreover, distal body support interlinking portion 331 has a shape that corresponds with the shape of opening 325 of distal body support connection portion 327, such that when distal body support interlinking portion 331 is in its collapsed state, distal body support interlinking portion 331 interlinks with distal body support connection portion 327. When interlinked, distal body support connection portion 327 fits within opening 329 of body support catheter connection 324, and distal body support interlinking portion 331 of body support catheter connection 324 fits within opening 325 of distal body support connection portion 327. For example, distal body support connection portion 327 and distal body support interlinking portion 331 may have a T-shape.

Proximal body support interlinking portion 335 of body support catheter connection 324 may have a shape that corresponds with the shape of opening 337 of body support catheter proximal portion 326 such that proximal body support interlinking portion 335 may interlink with body support catheter proximal portion 326. When interlinked, proximal interlinking portion 335 fits within opening 337 of body support catheter proximal portion 326, and proximal body support connection portion 339 of body support catheter proximal portion 326 fits within opening 333 of body support catheter connection 324. For example, proximal body support connection portion 339 and proximal body support interlinking portion 335 may have a T-shape. Moreover, body support catheter connection 324 may be made of a different material from body support catheter proximal portion 326.

Body support catheter lock 330 may include proximal portion 336 having one or more openings 338 sized and shaped to receive one or more prongs 334 of body support catheter pusher 332. In addition, body support catheter lock 330 and body support catheter pusher 332 have a lumen sized and shaped to receive distal body support locking portion 322, distal body support connection portion 327, body support catheter connection 324, and body support catheter proximal portion 326. Accordingly, body support catheter pusher 332 may be advanced distally responsive to actuation at actuator 108, e.g., by actuating a knob or button on actuator 108 in a first direction, such that one or more prongs 334 engage with one or more openings 338 to push body support catheter lock 330 distally over body support catheter connection 324 and distal body support locking portion 322 to lock body support catheter distal portion 320 to elongated rail distal portion 302, as described with regard to FIGS. 10A to 10G. In addition, body support catheter distal portion 320 may act as an end stop, thereby prevent excessive distal movement of body support catheter lock 330 and body support catheter pusher 332.

Body support catheter lock 330 may include one or more longitudinal slits 328 which may permit the distal portion of body support catheter lock 330 to expand radially as body support catheter lock 330 is pushed over interference locking portion 323 of distal locking portion 322. As body support catheter lock 330 expands radially, it engages with the inner surface of the lumen of shaping catheter distal portion 340 to thereby lock body support catheter distal portion 320 to shaping catheter distal portion 340. FIG. 7E illustrates the body support catheter in the delivery state where body support catheter lock 330 is disposed over distal body support interlinking portion 331 of body support catheter connection 324 while distal body support interlinking portion 331 is in its collapsed state due to the force applied by body support catheter lock 330, and interlinked with distal body support connection portion 327.

Figure 10A:
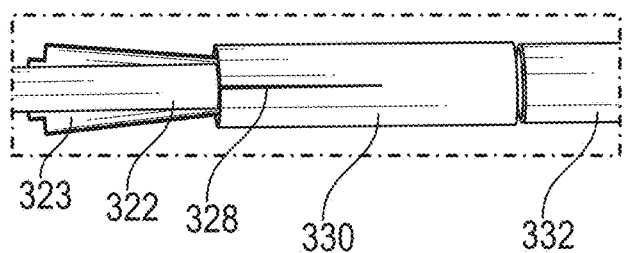
FIGS. 10A to 10G are views of an exemplary method for disengaging the distal, implantable portion from the proximal, delivery portion of the body support catheter and for locking components of the distal, implantable portion together for implantation.
Figure 10B:
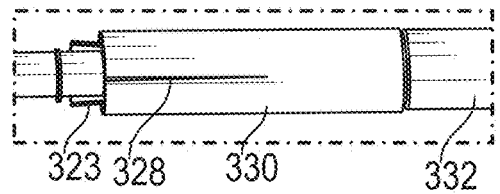
Figure 10C:
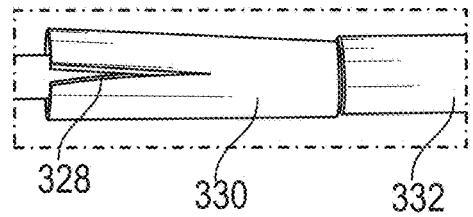

Referring now to FIGS. 10A to 10G, an exemplary method for detaching the body support catheter is described. As shown in FIG. 10A, body support catheter lock 330 is disposed over distal body support interlinking portion 331 of body support catheter connection 324 while distal body support interlinking portion 331 is in its collapsed state and interlinked with distal body support connection portion 327. As shown in FIG. 10A, interference locking portion 323 may have a thickness that increases in the distal direction, thereby forming a ramped outer surface. Accordingly, as body support catheter pusher 332 is advanced distally to push body support catheter lock 330 distally over interference locking portion 323 of distal body support locking portion 322, as shown in FIG. 10B, interference locking portion 323 is pushed radially inward toward the longitudinal axis of the body support catheter. The bottom surface of interference locking portion 323 will extend into the lumen of distal body support locking portion 322 where elongated rail distal portion 302 may be disposed, and thus, interference locking portion 323 will lock body support catheter distal portion 320 to elongated rail distal portion 302 when body support catheter lock 330 is positioned over interference locking portion 323. As shown in FIG. 10C, one or more longitudinal slits 328 may expand slightly as body support catheter lock 330 is advanced distally over interference locking portion 323 of distal locking portion 322, such that body support catheter lock 330 engages with the inner surface of the lumen of shaping catheter distal portion 340 (not shown) to thereby lock body support catheter distal portion 320 to shaping catheter distal portion 340. The thickness of interference locking portion 323 may dictate the force of locking between body support catheter distal portion 320, elongated rail distal portion 302, and shaping catheter distal portion 340. For example, body support catheter lock 330 may be a displacement-controlled lock such that as body support catheter lock 330 is advanced distally over interference locking portion 323, the force applied to body support catheter lock 330 rises and then reaches a plateau, rather than increasing the more it is pushed. As will be understood by a person having ordinary skill in the art, after advancement of body support catheter lock 330 is complete, relative motion between body support catheter distal portion 320 and elongated rail distal portion 302 is constrained, and thus telescoping is locked, and relative motion between body support catheter distal portion 320 and shaping catheter distal portion 340 is constrained, thereby locking the angle of the elongated rail.

Figure 10D:
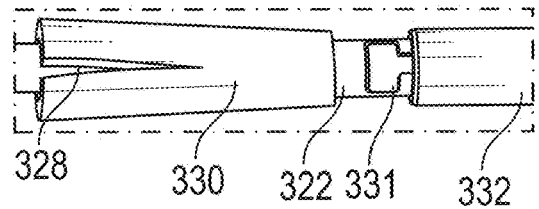
Figure 10E:
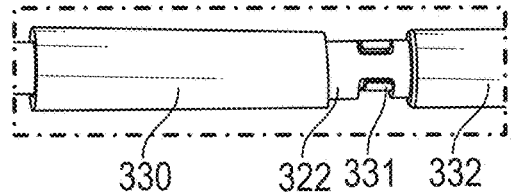
Figure 10F:
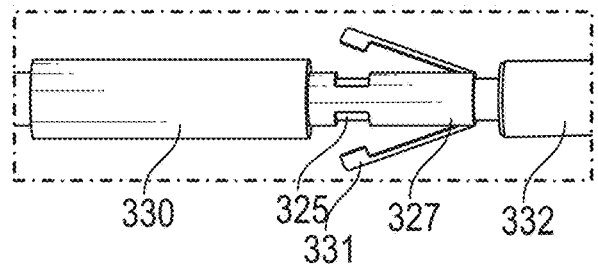
Figure 10G:
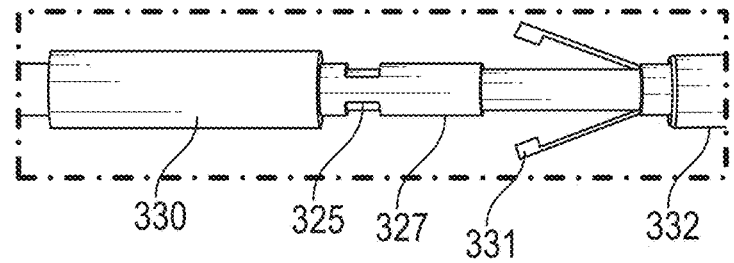

As shown in FIGS. 10D and 10E, while body support catheter lock 330 is positioned over interference locking portion 323 of distal body support locking portion 322 such that body support catheter distal portion 320 is locked to elongated rail distal portion 302 and to shaping catheter distal portion 340, body support catheter pusher 332 may be retracted proximally responsive to actuation at actuator 108, e.g., by actuating a knob or button on actuator 108 in a second direction opposite to the first direction, to thereby expose distal body support interlinking portion 331 of body support catheter connection 324. When body support catheter pusher 332 is retracted proximally enough such that distal body support interlinking portion 331 is entirely exposed, distal body support interlinking portion 331 may self-expand from its collapsed state within body support catheter pusher 332 to its expanded state, thereby disengaging with distal body support connection portion 327, as shown in FIG. 10F. Preferably, body support catheter pusher 332 only exposes distal body support interlinking portion 331, and remains disposed over proximal body support interlinking portion 335 and proximal body support connection portion 339. Alternatively, distal body support interlinking portion 331 may be shape set to expand radially inwards or in another direction to disengage with distal body support connection portion 327. When distal body support interlinking portion 331 is disengaged from distal body support connection portion 327, body support catheter pusher 332, body support catheter proximal portion 326 and body support catheter connection 324 may be removed from the patient, while body support catheter distal portion 320 remains implanted within the patient, as shown in FIG. 10G. Further, elongated rail proximal portion 304 may be detached from elongated rail distal portion 302 as described above and removed from the patient.

As will be understood by a person having ordinary skill in the art, after distal body support interlinking portion 331 is disengaged from distal body support connection portion 327, elongated rail proximal portion 304 must be disengaged from elongated rail distal portion 302 so that elongated rail proximal portion 304 may be removed from the patient, while elongated rail distal portion 302 remains implanted within the patient.

Referring back to FIGS. 7F and 7G, support 300 may include a shaping catheter having shaping catheter distal portion 340 and shaping catheter lock 348 at distal, implantable portion 311 of support 300, and shaping catheter proximal portion 346, shaping catheter connection 344, and shaping catheter pusher 350 at proximal, delivery portion 310 of support 300. The shaping catheter may extend from actuator 108 toward prosthetic coaptation body 200.

Referring now to FIG. 11A, the shaping catheter is illustrated with shaping catheter distal portion 340 engaged with shaping catheter proximal portion 346 via shaping catheter connection 344. Referring to FIGS. 11B and 11C, the shaping catheter is shown with components separated for clarity. Shaping catheter distal portion 340, shaping catheter connection 344, and shaping catheter pusher 346 have a lumen sized and shaped to receive the body support catheter therethrough. The distal end of shaping catheter distal portion 340 preferably does not extend all the way to prosthetic coaptation body 200, such that body support catheter distal portion 320 extends beyond a distal end of shaping catheter distal portion 340 to be coupled to prosthetic coaptation body 200. As described above, the distal end of shaping catheter distal portion 340 may include a collar for facilitating straightening and bending of elongated rail distal portion 302 based on the relative position of shaping catheter distal portion 340 and elongated rail distal portion 302.

The proximal end of shaping catheter distal portion 340 may include distal shaping catheter locking portion 342 and distal shaping catheter connection portion 343. Distal shaping locking portion 342 and distal shaping connection portion 343 may be formed of a single piece and may have an outer diameter that is smaller than the outer diameter of shaping catheter distal portion 340. Alternatively, distal shaping locking portion 342 and distal shaping connection portion 343 may be separate components that are conjoined together. The tube formed by distal shaping locking portion 342 and distal shaping connection portion 343 may extend at least partially through the lumen of shaping catheter distal portion 340. Accordingly, distal shaping locking portion 342 and distal shaping connection portion 343 may have a lumen sized and shaped to receive the body support catheter therethrough.

As shown in FIG. 11C, distal shaping locking portion 342 may include features, e.g. bumps, wedges, or otherwise, to increase the effective diameter of the section, as realized per wedged portion 353. In some embodiments, wedged portion 353 may be formed similar to the wedged portion of interference locking portion 323 of the body support catheter. Distal shaping connection portion 343 may include opening 341, e.g., a T-shaped opening, sized and shaped to interlink with shaping catheter connection 344.

Shaping catheter connection 344 may include distal shaping interlinking portion 347 defined by opening 345 and proximal shaping interlinking portion 351 defined by opening 349. Distal shaping interlinking portion 347 may be biased radially outward, and may transition from the expanded state to a collapsed state upon application of a radially inward force, as described in further detail below. Moreover, distal shaping interlinking portion 347 has a shape that corresponds with the shape of opening 341 of distal shaping connection portion 343, such that when distal shaping interlinking portion 347 is in its collapsed state, distal shaping interlinking portion 347 interlinks with distal shaping connection portion 343. When interlinked, distal shaping connection portion 343 fits within opening 345 of shaping catheter connection 344, and distal shaping interlinking portion 347 of shaping catheter connection 344 fits within opening 341 of distal shaping connection portion 343. For example, distal shaping connection portion 343 and distal shaping interlinking portion 347 may have a T-shape.

Proximal shaping interlinking portion 351 of shaping catheter connection 344 may have a shape that corresponds with the shape of opening 352 of shaping catheter proximal portion 346 such that proximal shaping interlinking portion 351 may interlink with shaping catheter proximal portion 346. When interlinked, proximal shaping interlinking portion 351 fits within opening 352 of shaping catheter proximal portion 346, and proximal shaping connection portion 354 of shaping catheter proximal portion 346 fits within opening 349 of shaping catheter connection 344. For example, proximal shaping connection portion 354 and proximal shaping interlinking portion 351 may have a T-shape.

Shaping catheter lock 348 may include proximal portion 355 having one or more openings 356 sized and shaped to receive one or more prongs 357 of shaping catheter pusher 350. In addition, shaping catheter lock 348 and shaping catheter pusher 350 have a lumen sized and shaped to receive distal shaping locking portion 342, distal shaping connection portion 343, shaping catheter connection 344, and shaping catheter proximal portion 346. Accordingly, shaping catheter pusher 350 may be advanced distally responsive to actuation at actuator 108, e.g., by actuating a knob or button on actuator 108 in a first direction, such that one or more prongs 357 engage with one or more openings 356 to push shaping catheter lock 348 distally over wedged portion 353 of distal shaping locking portion 342, thereby causing shaping catheter lock 348 to expand and engage with the inner surface of the lumen of anchor tube 360 to lock shaping catheter distal portion 340 to anchor tube 360. For example, shaping catheter lock 348 may include one or more longitudinal slits 358 which may permit the distal portion of shaping catheter lock 348 to expand radially as shaping catheter lock 348 is pushed over distal locking portion 342.

In addition, shaping catheter distal portion 340 may act as an end stop, thereby prevent excessive distal movement of shaping catheter lock 348 and shaping catheter pusher 350. FIG. 7G illustrates the shaping catheter in the delivery state where shaping catheter lock 348 is disposed over distal shaping interlinking portion 347 of shaping catheter connection 344 while distal shaping interlinking portion 347 is in its collapsed state due to the force applied by shaping catheter lock 348, and interlinked with distal shaping connection portion 343.

Figure 12A:
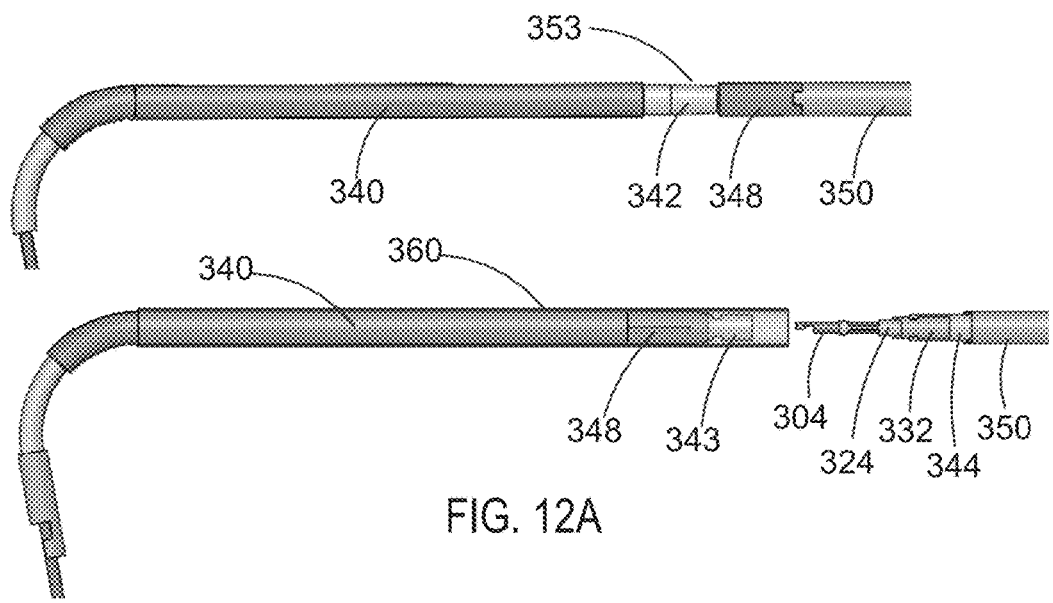
FIG. 12A illustrates the shaping catheter in an engaged configuration suitable for delivering the prosthetic device to the cardiac valve and a disengaged configuration where the distal, implantable portion remains implanted and the proximal, delivery portion can be removed from the patient.

Referring now to FIG. 12A, further details on the exemplary method for disengaging the shaping catheter are described, in accordance with some aspects. The top drawing illustrates the shaping catheter in an engaged configuration suitable for delivering the prosthetic device to the cardiac valve. Responsive to actuation at the actuator, e.g., at the handle, components of shaping catheter are moved to cause the distal portion of the shaping catheter to lock with the anchor tube, 360, and to cause the proximal portion to detach from the distal portion of the shaping catheter. For example, moving an interface (e.g., button, knob, etc.) on the actuator distally may push shaping catheter pusher 350 distally thereby pushing shaping catheter lock 348 distally causing the shaping catheter distal portion to lock with the anchor tube, 360. Further, moving the interface on the actuator proximally may cause shaping catheter pusher 350 to retract proximally, thereby exposing the distal shaping interlinking portion of shaping catheter connection 344 and permitting it to self-expand and disengage with distal shaping catheter connection portion, 343, of the shaping catheter distal portion, 340. The bottom drawing of FIG. 12A shows how the components have moved responsive to actuation. In the bottom drawing, the shaping catheter is in a disengaged configuration where the distal, implantable portion is designed to remain implanted in the patient with the prosthetic device while the proximal, delivery portion can be removed from the patient.

Initially, shaping catheter lock 348 is disposed over distal shaping interlinking portion 347 of shaping catheter connection 344 while distal shaping interlinking portion 347 is in its collapsed state and interlinked with distal shaping connection portion 342. As shown in FIG. 12A, wedged portion 353 may have a thickness that increases in the distal direction, thereby forming a ramped outer surface. Accordingly, as shaping catheter pusher 350 is advanced distally to push shaping catheter lock 348 distally over wedged portion 353 of distal shaping locking portion 342, wedged portion 353 causes shaping catheter lock 348 to expand radially outward away from the longitudinal axis of the shaping catheter. Accordingly, the outer surface of shaping catheter lock 348 will engage with the inner surface of the lumen of anchor tube 360, thereby constraining relative motion between shaping catheter distal portion 340 and anchor tube 360. One or more longitudinal slits 358 may expand slightly as shaping catheter lock 348 is advanced distally over wedged portion 353 of distal shaping locking portion 342.

While shaping catheter lock 348 is positioned over wedged portion 353 of distal locking portion 342 such that shaping catheter distal portion 340 is locked to anchor tube 360, shaping catheter pusher 350 may be retracted proximally responsive to actuation at actuator 108, e.g., by actuating a knob or button on actuator 108 in a second direction opposite to the first direction, to thereby expose distal shaping interlinking portion 347 of shaping catheter connection 344. When shaping catheter pusher 350 is retracted proximally enough such that distal shaping interlinking portion 347 is entirely exposed, distal shaping interlinking portion 347 may self-expand from its collapsed state within shaping catheter pusher 350 to its expanded state, thereby disengaging with distal shaping connection portion 343. When distal shaping interlinking portion 347 is disengaged from distal shaping connection portion 343, shaping catheter pusher 350, shaping catheter proximal portion 346, and shaping catheter connection 344 may be withdrawn into the delivery sheath and can subsequently be removed from the patient, while shaping catheter distal portion 340 remains implanted within the patient. Further, body support catheter distal portion 320 may be detached from the body support catheter proximal components and elongated rail distal portion 302 may be detached from elongated rail distal portion 304 as described above, such that the proximal components may be removed from the patient, while body support catheter distal portion 320 and elongated rail distal portion 302 may remain implanted within the patient, as shown in FIG. 12A.

As will be understood by a person having ordinary skill in the art, after distal shaping interlinking portion 347 is disengaged from distal shaping connection portion 343, distal body support interlinking portion 331 can subsequently be disengaged from distal body support connection portion 327 as described above, through the action of withdrawal so that body support catheter pusher 332, body support catheter proximal portion 326, and body support catheter connection 324 may be removed from the patient, while body support catheter distal portion 320 and elongated rail distal portion 302 remain implanted within the patient. In addition, elongated rail proximal portion 304 must be disengaged from elongated rail distal portion 302 after distal body support interlinking portion 331 is disengaged from distal body support connection portion 327 so that elongated rail proximal portion 304 may be removed from the patient.

Figure 12B:
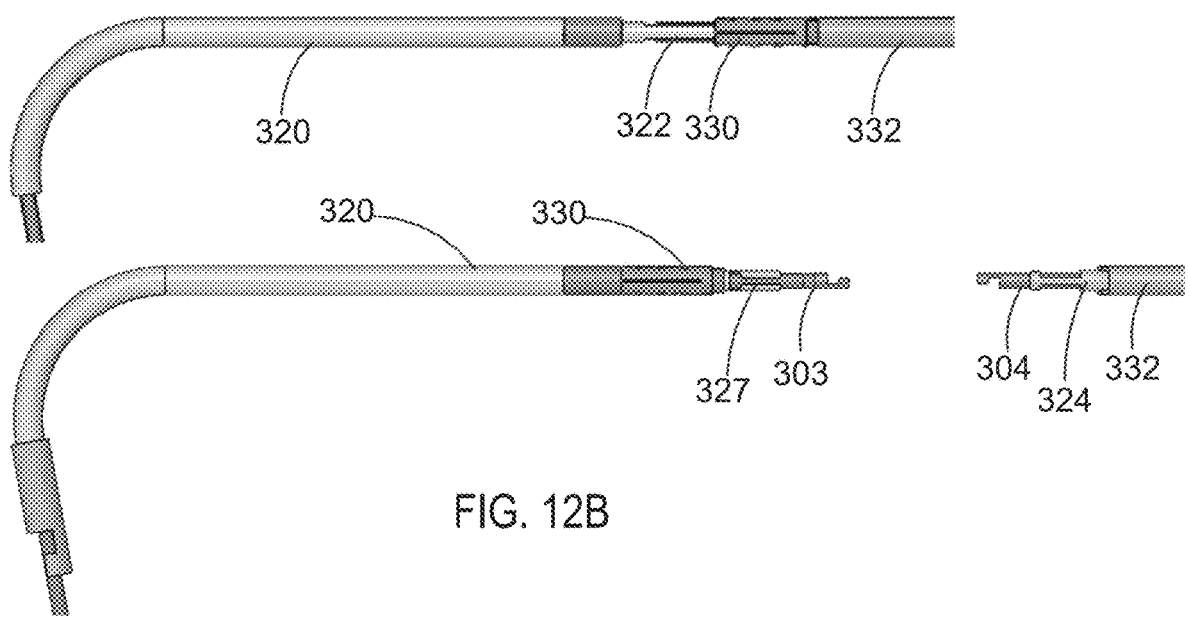
FIG. 12B illustrates the body support catheter in an engaged configuration suitable for delivering the prosthetic device to the cardiac valve and a disengaged configuration where the distal, implantable portion remains implanted and the proximal, delivery portion can be removed from the patient.

Referring now to FIG. 12B, further details on the exemplary method for disengaging the body support catheter after the shaping catheter is disengaged is described, in accordance with some aspects. The top drawing illustrates the body support catheter in an engaged configuration suitable for delivering the prosthetic device to the cardiac valve. Responsive to actuation at the actuator, e.g., at the handle, components of body support catheter are moved to cause the distal portion to lock with the distal portions of the shaping catheter and the elongated rail, and to cause the proximal portion to detach from the distal portion of the body support catheter. For example, moving an interface (e.g., button, knob, etc.) on the actuator (which may be the same or different interface moved for unlocking the shaping catheter) distally may push body support catheter pusher 332 distally thereby pushing body support catheter lock 330 distally causing body support catheter distal portion 320 to lock with elongated rail distal portion 302 shaping catheter distal portion 340. Subsequently moving the interface on the actuator proximally may cause body support catheter pusher 332 to retract proximally, thereby exposing distal body support interlinking portion 331 of body support catheter connection 324 and permitting it to self-expand and disengage with the distal portion of the body support catheter. Preferably, body support catheter pusher 332 only exposes distal body support interlinking portion 331, and remains disposed over proximal body support interlinking portion 335 and proximal body support connection portion 339. The bottom drawing of FIG. 12B shows how the components have moved responsive to actuation. In the bottom drawing, the body support catheter is in a disengaged configuration where the distal, implantable portion is designed to remain implanted in the patient with the prosthetic device while the proximal, delivery portion can be removed from the patient.

Initially, body support catheter lock 330 and/or body support catheter pusher 332 are disposed over distal body support interlinking portion 331 of body support catheter connection 324 while distal body support interlinking portion 331 is in its collapsed state and interlinked with distal body support connection portion 327. As body support catheter pusher 332 is advanced distally to push body support catheter lock 330 distally over interference locking portion 323 of distal body support locking portion 322, interference locking portion 323 is pushed radially inward toward the longitudinal axis of the body support catheter. The bottom surface of interference locking portion 323 will extend into the lumen of distal body support locking portion 322 where elongated rail distal portion 302 may be disposed, and thus, interference locking portion 323 will lock body support catheter distal portion 320 to elongated rail distal portion 302 when body support catheter lock 330 is positioned over interference locking portion 323. In addition, interference locking portion 323 may cause support catheter lock 330 to expand radially outward such that support catheter lock 330 engages with the inner surface of the lumen of shaping catheter distal portion 340, to thereby lock body support catheter distal portion 320 with shaping catheter distal portion 340 when body support catheter lock 330 is positioned over interference locking portion 323. One or more longitudinal slits 328 may expand slightly as body support catheter lock 330 is advanced distally over interference locking portion 323 of distal locking portion 322.

While body support catheter lock 330 is positioned over interference locking portion 323 of distal body support locking portion 322 such that body support catheter distal portion 320 is locked to elongated rail distal portion 302, body support catheter pusher 332 may be retracted proximally to thereby expose distal body support interlinking portion 331 of body support catheter connection 324. When body support catheter pusher 332 is retracted proximally enough such that distal body support interlinking portion 331 is entirely exposed, distal body support interlinking portion 331 may self-expand from its collapsed state within body support catheter pusher 332 to its expanded state, thereby disengaging with distal body support connection portion 327. When distal body support interlinking portion 331 is disengaged from distal body support connection portion 327, body support catheter pusher 332, body support catheter proximal portion 326, and body support catheter connection 324 may be removed from the patient, while shaping catheter distal portion 340, body support catheter distal portion 320 remains implanted within the patient, as shown in FIG. 12B.

After or while distal body support interlinking portion 331 is disengaged from distal body support connection portion 327, elongated rail proximal portion 304 must be disengaged from elongated rail distal portion 302 so that elongated rail proximal portion 304 may be removed from the patient. For example, once the components of the body support catheter over the detachment portion of the elongated rail have been disengaged and no longer hold the detachment portion of the elongated rail together, the elongated rail may be detached.

Figure 12C:
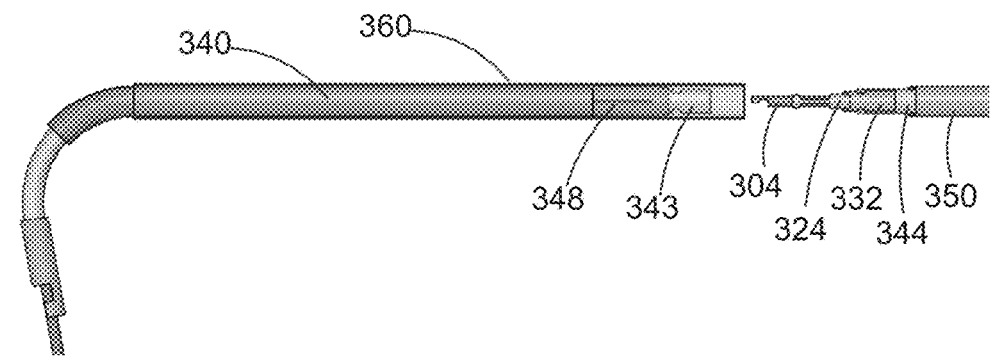
FIGS. 12C to 12F illustrate exemplary components of the detachable support in a disengaged configuration.
Figure 12D:
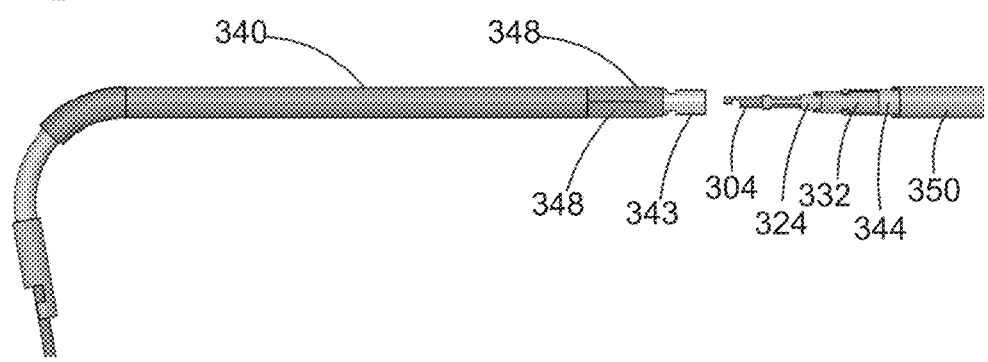

FIG. 12C illustrates support 300 in a disengaged configuration where shaping catheter pusher 350, shaping catheter proximal portion 346, shaping catheter connection 344, body support catheter pusher 332, body support catheter connection 324, and elongated rail proximal portion 304 are disengaged from shaping catheter distal portion 340, shaping catheter lock 348, body support catheter distal portion 320, body support catheter lock 330, and elongated rail distal portion 302. In addition, as shown in FIG. 12C, anchor tube 360 is disposed over body support catheter distal portion 320. FIG. 12D illustrates support 300 in the disengaged configuration as described with regard to FIG. 12C, without anchor tube 360 shown.

Figure 12E:
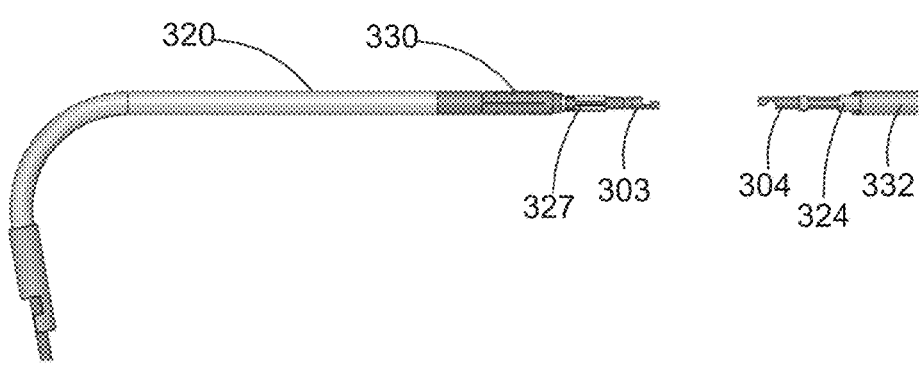
Figure 12F:
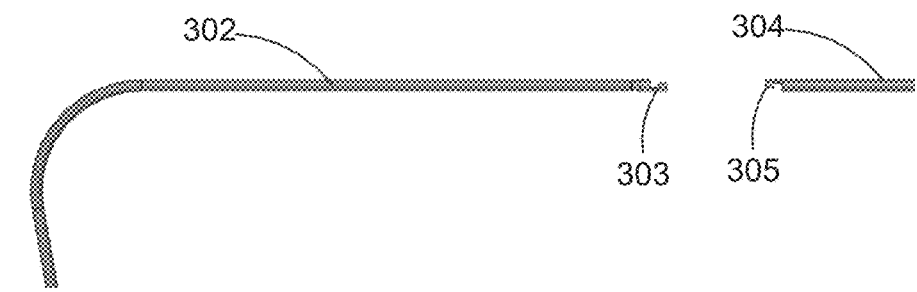

FIG. 12E illustrates support 300 in the disengaged configuration as described with regard to FIG. 12D, without shaping catheter distal portion 340, shaping catheter lock 348, shaping catheter connection 344, and shaping catheter pusher 350 shown. FIG. 12F illustrates the elongated rail of support 300 in the disengaged configuration as described with regard to FIG. 12E, without body support catheter distal portion 320, body support catheter lock 330, body support catheter pusher 332, and body support catheter connection 324 shown.

Referring now to FIG. 13 an exemplary valve connection area for coupling support 300 with prosthetic coaptation body 200 is described. As shown in FIG. 13, the distal end of body support catheter 320 may be coupled to spine 201 of prosthetic coaptation body 200 at valve connection area 222. For example, body support catheter 320 may be coupled to spine 201 of prosthetic coaptation body 200 via a snap fit connection, as described in further detail below with regard to FIGS. 14A to 14E.

Figure 14C:
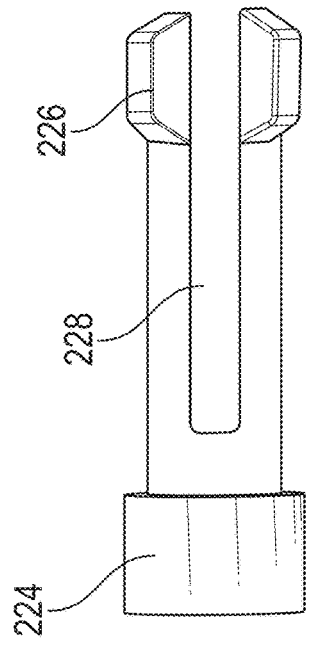
FIGS. 14A to 14E illustrate an exemplary snap fit system for coupling the prosthetic device to the detachable support.
Figure 14D:
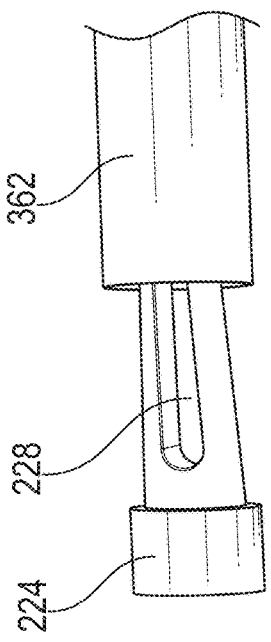
Figure 14E:
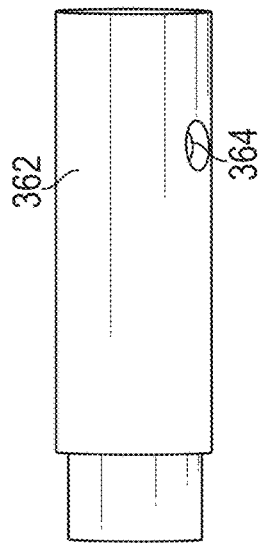
Figure 14A:
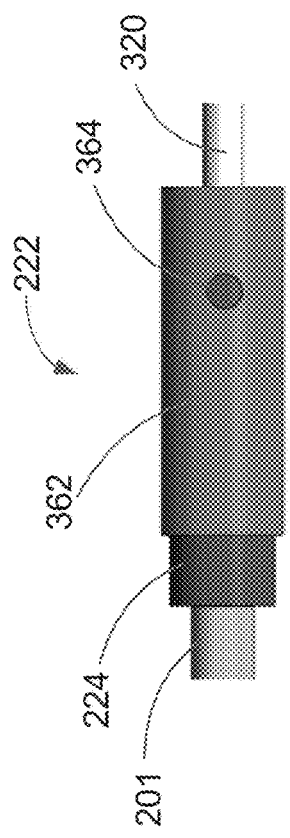
Figure 14B:
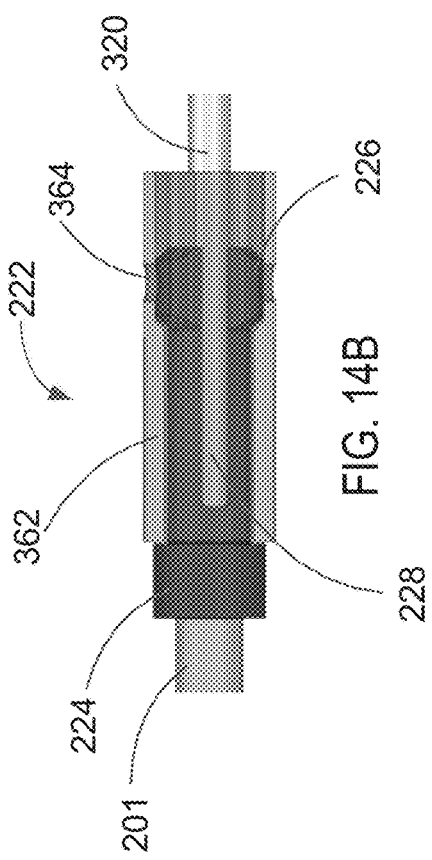

Referring now to FIGS. 14A to 14E, an exemplary snap fit system for coupling the prosthetic coaptation body to the detachable support is described. As shown in FIGS. 14A and 14B, spine 201 of prosthetic coaptation body 200 may be coupled at its proximal end to spine connector 224 via snap fit system 222. The distal portion of spine connector 224, e.g., the portion of spine connector 224 coupled to spine 201, may have a first outer diameter, which may be larger than the outer diameter of spine 201. The mid-portion of spine connector 224 proximal to the distal portion may have an outer diameter that is smaller than the outer diameter of the distal portion of spine connector 224, and the proximal-most portion of spine connector 224 may have an outer diameter that is larger than the mid-portion of spine connector 224. As shown in FIGS. 14B and 14C, at least a portion of the mid-portion and the proximal portion of spine catheter 224 may have an opening 228, thereby defining two prongs 226. Accordingly, upon application of sufficient force via the proximal portion of support connector 224, prongs 226 may be moved radially inward, and may return to its natural state upon the removal of the external force. As shown in FIG. 14C, the proximal and distal edges of the proximal portion of spine connector 224 may be rounded and/or sloped to facilitate moving prongs 226 radially inward.

In addition, the proximal end of spine connector 224 may be coupled to support connector 362. Support connector 362 may have a tubular shape and an internal cavity having a geometry corresponding with the shape of prongs 226 of spine connector 224. As shown in FIG. 14B, a distal portion of the cavity of support connector 362 may have a diameter equal to the outer diameter of the mid-portion of spine connecter 224, and a proximal portion of the cavity of support connector 362 may have a diameter equal to the outer diameter of the proximal portion of spine connector 224. Accordingly, as the proximal end of spine connector 224 is pushed into the cavity of support connector 362, the distal portion of the internal cavity of support connector 362 will push prongs 226 radially inward as shown in FIG. 14D. Spine connector 224 may be pushed into the cavity of support connector 362 until the proximal portion of spine connector 224 reaches the proximal portion of the cavity of support connector 362, such that prongs 226 return to its natural state as shown in FIGS. 14B and 14E. Moreover, as shown in FIG. 14B, the outer diameter of the distal portion of spine connector 224 may prevent further distal movement of support connector 362 relative to spine connector 224. In addition, the distal end of the elongated rail distal portion may be positioned within the cavity of support connector 362 when prongs 226 are disposed within the cavity, thereby preventing spine connector 224 from disengaging from support connector 362, e.g., via press fit.

As shown in FIG. 14A, support connector 362 may include one or more openings 364 adjacent to the proximal portion of the cavity of support connector 362. For example, when the elongated rail is removed, a dislodging tool may be inserted through one or more openings 364 to push the proximal portion of spine connector 224 radially inward, such that spine connector 224 may be disengaged from support connector 362. As will be understood by a person having ordinary skill in the art, support connector 362 may be coupled to the distal end of elongated rail distal portion 302 instead of, or in addition to, the distal end of body support catheter distal portion 320. In addition to, or alternatively, support connector 362 may be coupled to the distal end of shaping catheter distal portion 340.

Figure 15A:
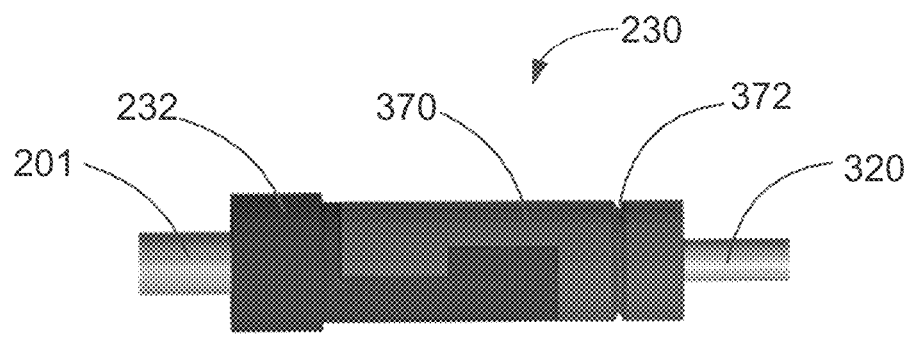
FIGS. 15A and 15B illustrate an exemplary interlinking connector system for coupling the prosthetic device to the detachable support.
Figure 15B:
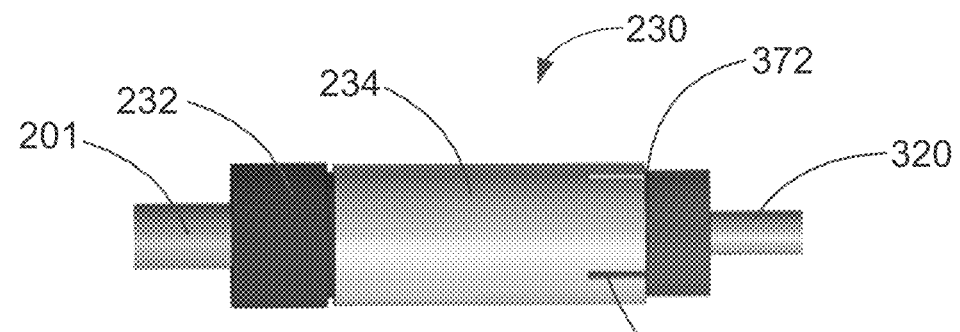

Referring now to FIGS. 15A and 15B, an exemplary interlinking connector system for coupling the prosthetic coaptation body to the detachable support is described. As shown in FIGS. 15A and 15B, spine 201 of prosthetic coaptation body 200 may be coupled at its proximal end to spine connector 232 via interlinking connector system 230. The distal portion of spine connector 232, e.g., the portion of spine connector 232 coupled to spine 201, may have a first outer diameter, which may be larger than the outer diameter of spine 201. The portion of spine connector 232 proximal to the distal portion of spine connector 232 may have a first hook geometry as shown in FIG. 15A. Spine connector 232 may be made of, e.g., Nitinol or other metals or polymers such as PEEK.

The distal end of body support catheter 320 may be coupled to support connector 370. The distal portion of support connector 370 may have a second hook geometry that corresponds with the first hook geometry of the proximal portion of spine connector 232 as shown in FIG. 15A. When engaged, the outer diameter of both the proximal portion of spine connector 232 and the distal portion of support connector 370 may form a tubular shape, and may be smaller than the outer diameter of the distal portion of spine connector 232. Support connector 370 may be made of, e.g., Nitinol or other metals or polymers such as PEEK. Accordingly, the interlinking connector system may have a polymer interface between spine connector 232 and support connector 370 to avoid galvanic corrosion between the two components. Alternatively, support connector 370 may be made of, e.g., stainless steel, and spine connector 232 may be made of, e.g., Nitinol. As will be understood by a person having ordinary skill in the art, all the spine connectors and support connectors described herein may be made of differing materials, e.g., Nitinol and stainless steel, and therefore may all have a polymer interface between support connector and spine connector to avoid galvanic corrosion between the two components. Support connector 370 may be made entirely of, e.g. PEEK. In addition, support connector 370 may be coupled to the distal end of body support catheter distal portion 320 via, e.g., gluing, overmoulding, welding, or soldering, depending on the material of support connector 370.

As further shown in FIG. 15A, support connector 370 may have groove 372 extending circumferentially around a proximal portion of support connector 370. In some embodiments, support connector 370 may have a plurality of grooves, which may have a barb-like feature to bias travel of the sleeve in one direction. As shown in FIG. 15B, when the proximal portion of spine connector 232 and the distal portion of support connector 370 are engaged, a sleeve, e.g., compression sleeve 234, may be advanced distally over support connector 370 and at least a portion of the proximal portion of spine connector 232, to apply a force thereon and maintain the engagement between spine connector 232 and support connector 370. As shown in FIG. 15B, the outer diameter of the distal portion of spine connector 232 may prevent further distal movement of compression sleeve 234. In addition, the proximal portion of compression sleeve 234 may include a plurality of slits 236, such that a plurality of protrusions circumferentially disposed along the proximal end of compression sleeve 234 may cause the proximal end of compression sleeve 234 to move slightly radially outward as compression sleeve 234 advances over support connector 370 until the plurality of protrusions engage with groove 372. Once compression sleeve 234 is engaged with groove 372 of support connector 370, engagement between spine connector 232 and support connector 370 will be maintained within compression sleeve 234.

Figure 16A:
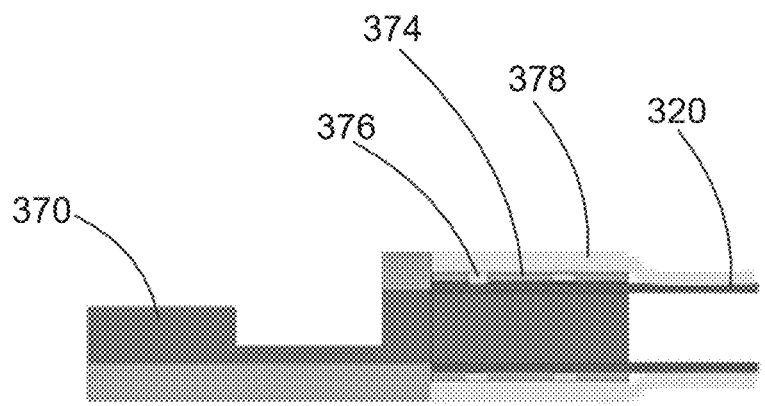
FIG. 16A illustrates an exemplary system for coupling the interlinking connector system to the body support catheter.

Referring now to FIG. 16A, an exemplary system for coupling the support connector of the interlinking connector system to the body support catheter is described. As shown in FIG. 16A, proximal portion 374 may have a tubular shape and a lumen sized and shaped to receive the distal end of body support catheter 320. Proximal portion 374 may have a plurality of openings 376 extending from the lumen of proximal portion 374 to the outer surface of proximal portion 374. In addition, outer sleeve 378 may be wrapped over proximal portion 374 and at least a portion of body support catheter 320, as shown in FIG. 16A. Accordingly, a polymer may be disposed through the plurality of openings 376 to bond outer sleeve 378 to body support catheter 320.

Figure 16B:
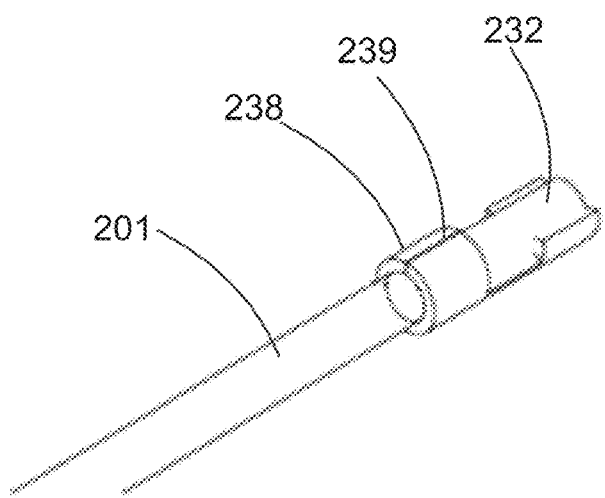
FIGS. 16B and 16C illustrate an exemplary system for coupling the interlinking connector system to the prosthetic device.
Figure 16C:
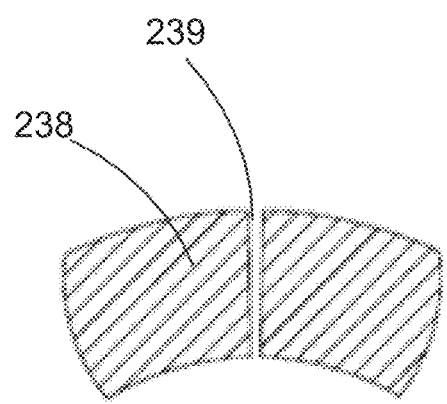

Referring now to FIGS. 16B and 16C, an exemplary system for coupling the interlinking connector system to the prosthetic coaptation body is described. As shown in FIGS. 16B and 16C, proximal portion 238 of spine connector 232 may include slit 239 extending from an inner surface of proximal portion 238 to the outer surface of proximal portion 238. Accordingly, spine 201 may be slightly larger than the lumen of proximal portion 238, such that slit 239 may provide relief to proximal portion 238 as support connector 232 is advanced over spine 201.

Referring now to FIGS. 17A to 17H, an exemplary method of inserting and positioning prosthetic coaptation body 200 across a native valve is shown. Prior to the implantation procedure, the patient may undergo a cardiac gated-CT to define the right heart and SVC anatomy. For the procedure, the patient may be fully anesthetized and may undergo right atrial and ventricular angiography. A sheath (e.g., 26 French sheath) may be inserted into the right internal jugular vein and a femoral venous (e.g., 9 Fr) line may be inserted for delivery of an intracardiac echo probe. All venous access may be obtained by ultrasound guidance. As shown in the figures described below, the prosthetic device may be deployed out of the delivery sheath and into the right atrium. The anchor system may then be manipulated under x-ray guidance to increase the bend angle and advance the prosthetic device until it crosses the tricuspid annulus. Once the initial device position is achieved with the prosthetic device across the tricuspid valve, a sheath may be retracted further to deploy the stent in the SVC and then positioning may be further adjusted to determine the final, optimal position. Correct device positioning may be confirmed by fluoroscopy and echocardiography. Clinical, hemodynamic, and echocardiographic outcomes may be assessed serially during the procedure to achieve optimum position. Echocardiography may be performed at baseline and after device placement to assess device function and tricuspid regurgitation. Once the optimal position is achieved, the locks in the handle may be released to lock and detach the system (e.g., a plurality of locks such as two locks and a plurality of disconnected elements such as four disconnected elements), and the handle and sheath can then be removed.

Figure 17A:
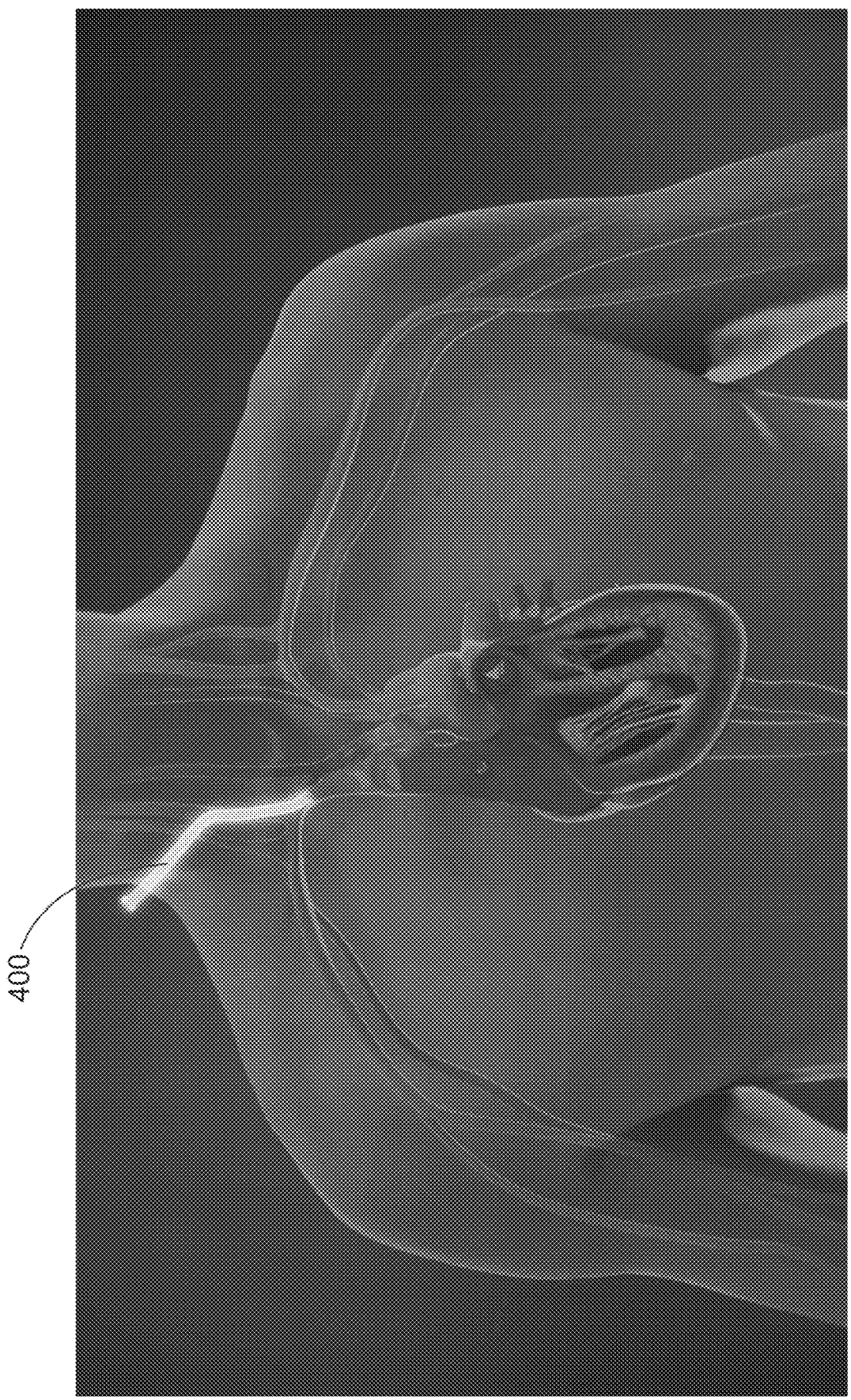
Figure 17B:
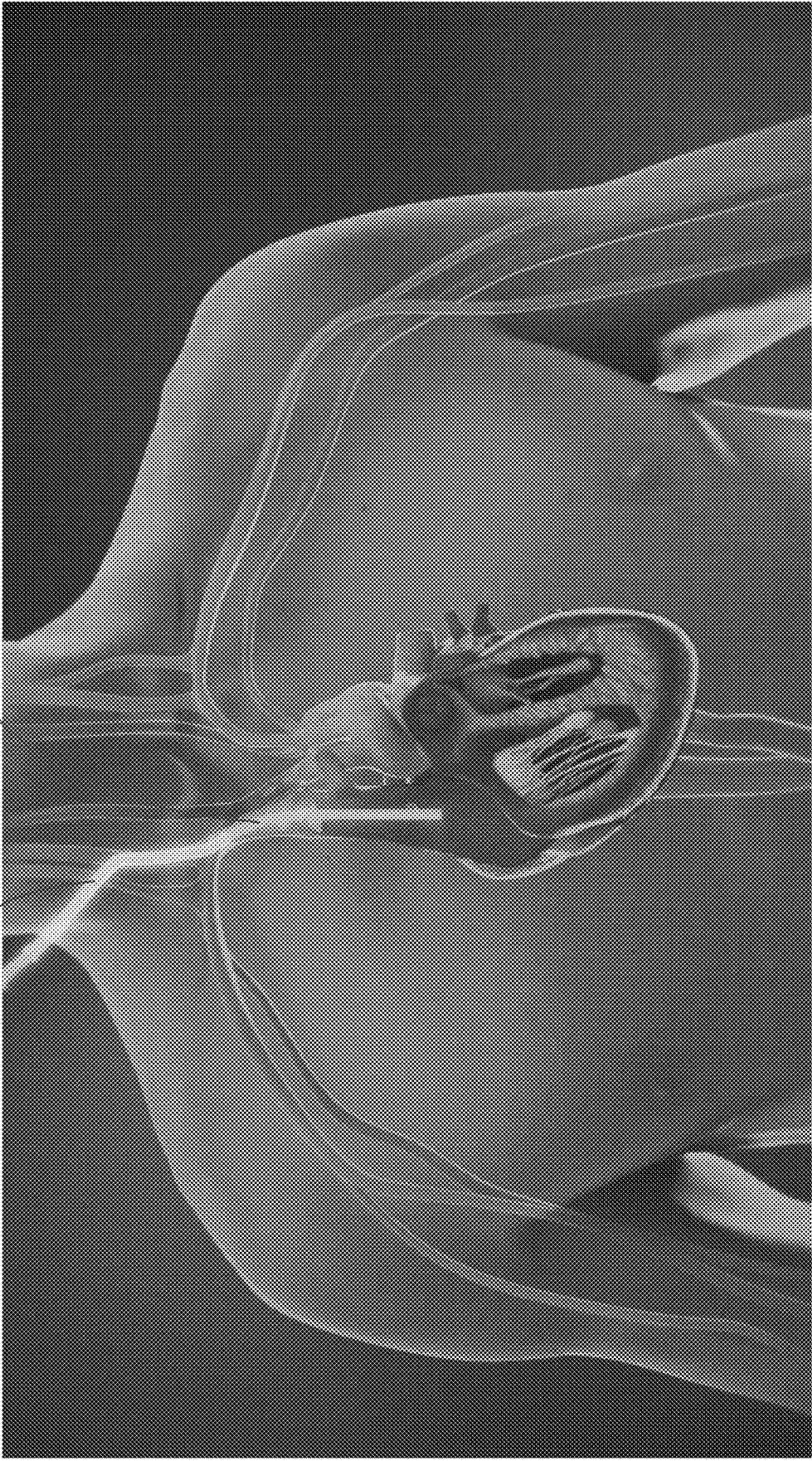

In FIG. 17A, sheath introducer 400 is inserted percutaneously into a blood vessel, e.g., through the jugular vein near a patient's neck or via the femoral artery. Sheath introducer 400 provides an opening for a clinician to percutaneously insert prosthetic coaptation body 400 and support 300 into the blood vessel. In FIG. 17B, delivery sheath 402 is inserted through sheath introducer 400 and advanced distally into the area in which prosthetic coaptation body 200 will be deployed. In the case of a damaged tricuspid valve, for example, delivery sheath 402 will extend through the inferior or superior vena cava into the right atrium such that the distal end of delivery sheath 402 is in the right atrium. In some cases, a guide wire may be introduced prior to inserting delivery sheath 402 to guide delivery sheath 402 through the blood vessel. Delivery sheath 402 preferably contains prosthetic coaptation body 200 in its compressed delivery state and support 300. Preferably, anchor 500 and anchor tube 360 may also be contained in delivery sheath 402, where anchor 500 is in a compressed delivery state.

Figure 17D:
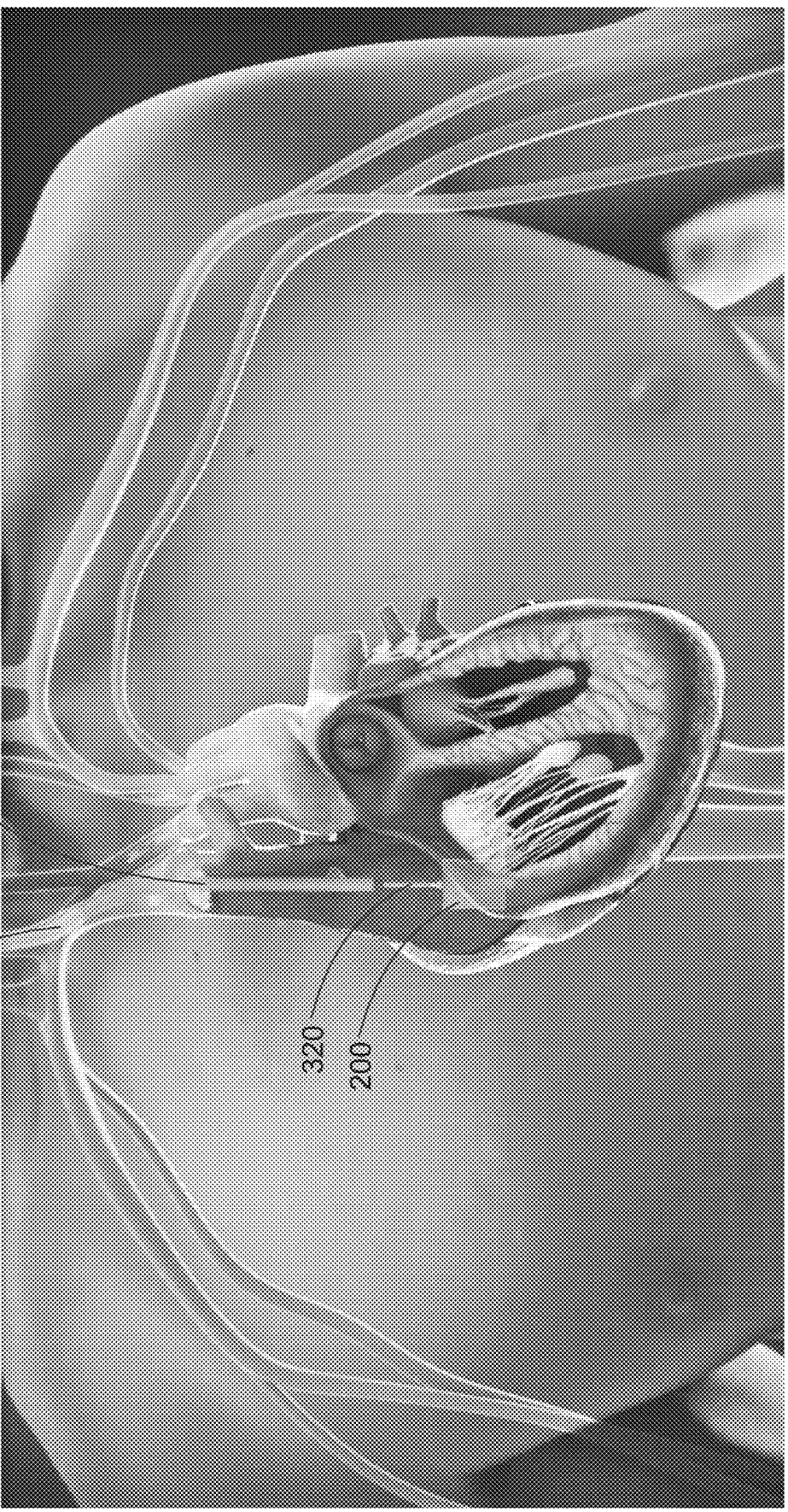
Figure 17E:
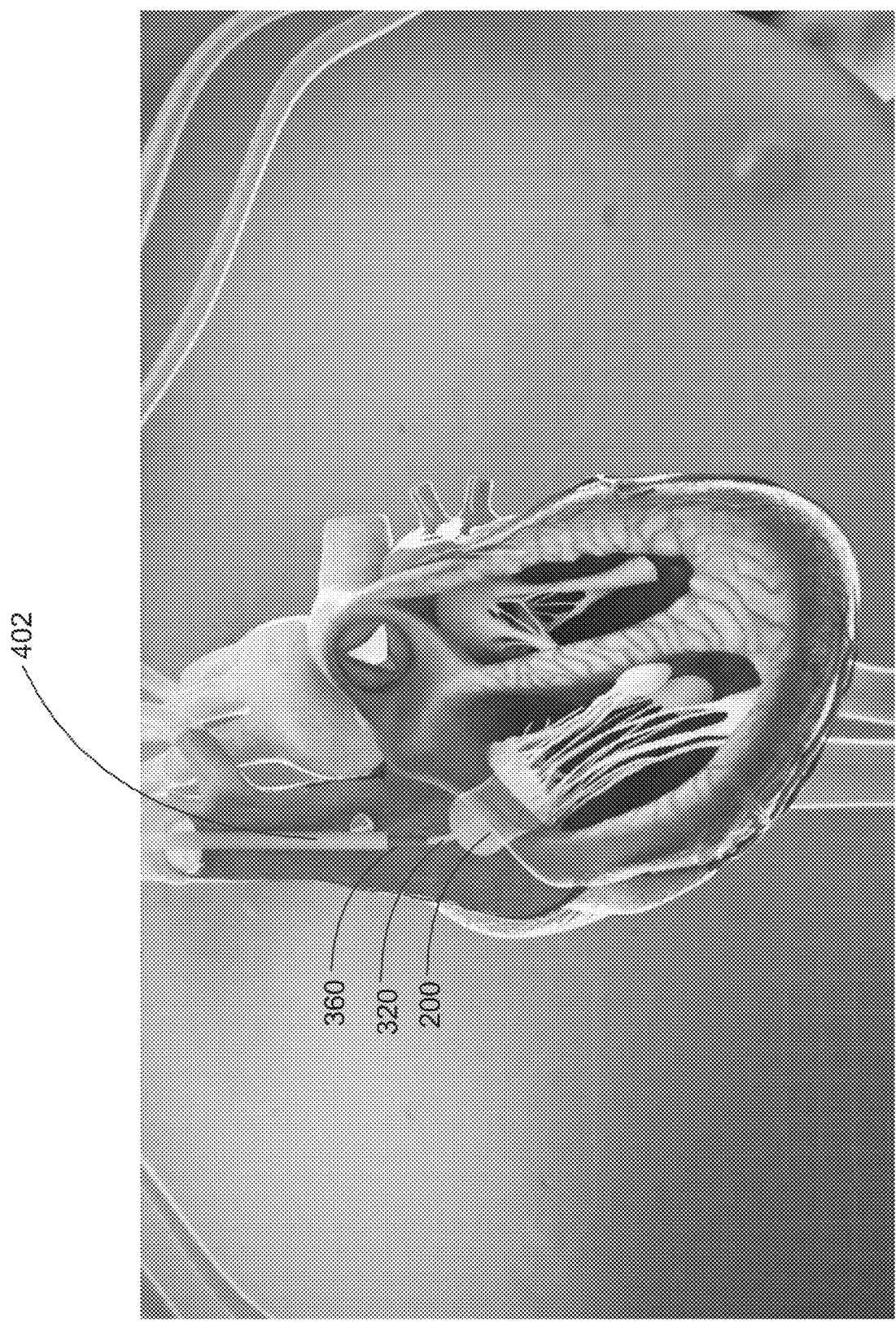

As illustrated in FIG. 17C, prosthetic coaptation body 200 is moved distally, e.g., using actuator 108 and/or interfaces 110, 112, 114, 116, 118, 120 out the distal end of delivery sheath 402, exposing prosthetic coaptation body 200, which expands to an expanded deployed state. For example, a clinician may move actuator 108 distally while holding delivery sheath 402 in place such that the prosthetic device moves out the distal end of the sheath and self-expands upon deployment. Support 300 may alternatively be held in place while delivery sheath 402 is withdrawn to expose prosthetic coaptation body 200. FIG. 17D shows prosthetic coaptation body 200 in its fully expanded state. As illustrated in FIG. 17E, body support catheter 320 may be steered to orient prosthetic coaptation body 200 in its deployed orientation using actuator 108 and/or one or more interfaces 110, 112, 114, 116, 118, 120.

Figure 17F:
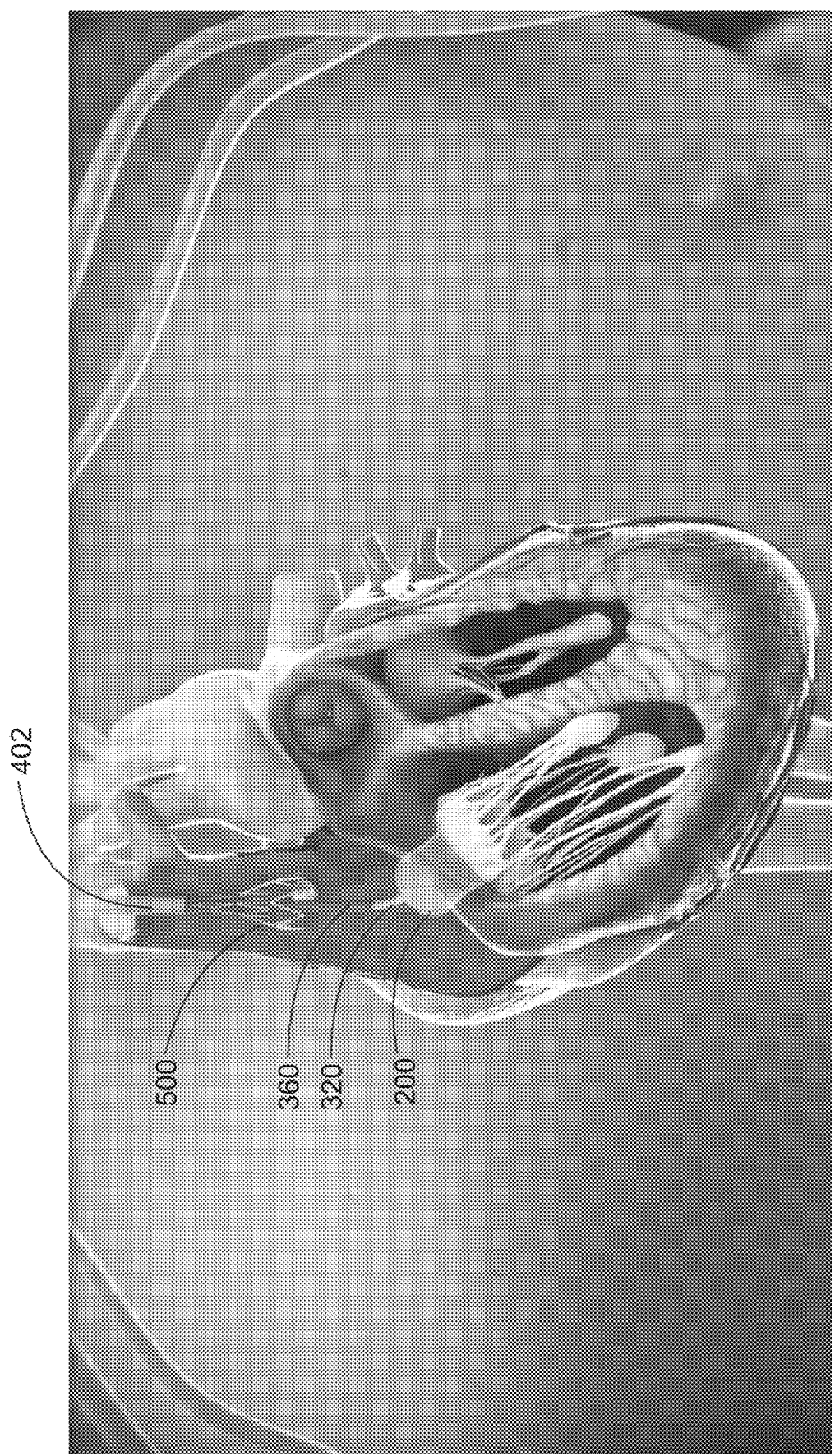
Figure 17G:
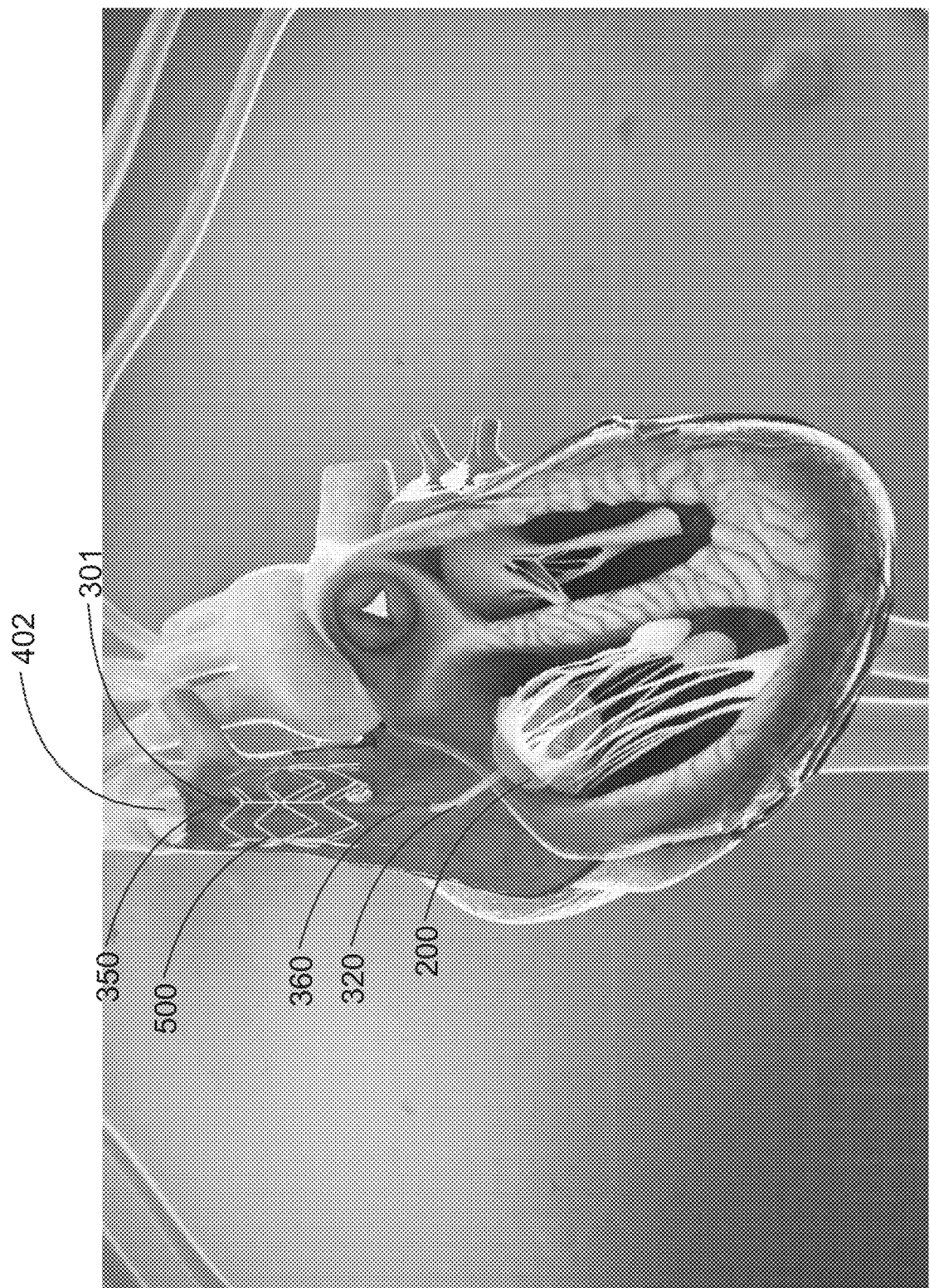

Anchor tube 360 is partially exposed, either by being pushed through delivery sheath 402 or by withdrawing delivery sheath 402 while holding in place anchor tube 360. As illustrated in FIG. 17F, delivery sheath 402 is further withdrawn, exposing anchor 500, which expands upon exposure from delivery sheath 402. As illustrated in FIG. 17G, anchor 500 is fully exposed and expanded, and engages with the walls of a blood vessel, holding itself in position. In the case of a damaged tricuspid valve, as shown, anchor 500 may engage the walls of the superior vena cava. Prosthetic coaptation body 200 may then be moved into its final deployed position using actuator 108 and/or interfaces 110, 112, 114, 116, 118, 120. For example, the interface operatively coupled to the shaping catheter may be actuated to adjust extension of the shaping catheter relative to the anchor tube to extend prosthetic coaptation body 200 to the desired distance within the native heart valve. In addition, the interface operatively coupled to the elongated rail may be actuated to adjust the angle of the elongated rail relative to the shaping catheter such that prosthetic coaptation body 200 is a positioned at the desired angle relative to anchor 500. Moreover, the interface operatively coupled to body support catheter may be actuated to telescope the body support catheter relative to the elongated rail to position prosthetic coaptation body 200 in the desired position within the native valve. Additionally, the catheters of support 300 may be rotated, e.g., by rotating actuator 108, relative to anchor 500. Once prosthetic coaptation body 200 is properly positioned, the locking and disengagement process described above with regard to FIGS. 12A and 12B may be implemented to lock the distal components of support 300 together, and disengage the proximal components of support 300 from the distal components at the detachment area so that the proximal components may be removed from the patient.

For example, anchor 500 and anchor tube 360 are positioned in a location close to detachment area 301, at the proximal ends of shaping catheter distal portion 340, body support catheter distal portion 320, and elongated rail distal portion 302. The interface operatively coupled to body support catheter pusher 332 may be actuated to push body support catheter lock 330 such that body support catheter lock 330 causes interference locking portion 323 to clamp down on elongated rail distal portion 302 to lock body support catheter distal portion 320 to elongated rail distal portion 302 and body support catheter lock 330 expands radially outward against shaping catheter distal portion 340 to lock body support catheter distal portion 320 to shaping catheter distal portion 340. The interface may then be actuated in the opposite direction such that body support catheter pusher 332 is retracted proximally to cause body support catheter connection 324 to detach from body support catheter distal portion 320. The interface operatively coupled to shaping catheter pusher 350 may be actuated to push shaping catheter lock 348 such that shaping catheter lock 348 expands radially outward against anchor tube 360, locking shaping catheter distal portion 340 to anchor tube 360, while anchor 500 is fixed in position and coupled to shaping catheter distal portion 340 via anchor tube 360. The interface may then be actuated in the opposite direction such that shaping catheter pusher 350 is retracted proximally to cause shaping catheter connection 344 to detach from shaping catheter distal portion 340. The interface operatively coupled to anchor tube sleeve 390 may be actuated to retract anchor tube sleeve 390 to cause anchor tube connection 384 to detach from anchor tube distal portion 380. As will be understood by a person having ordinary skill in the art, when detachment of the proximal components from the distal components of the support does not require self-expanding connections, the detachment of the elongated rail, body support catheter, shaping catheter, and anchor tube may be performed independently and in any order.

Figure 17H:
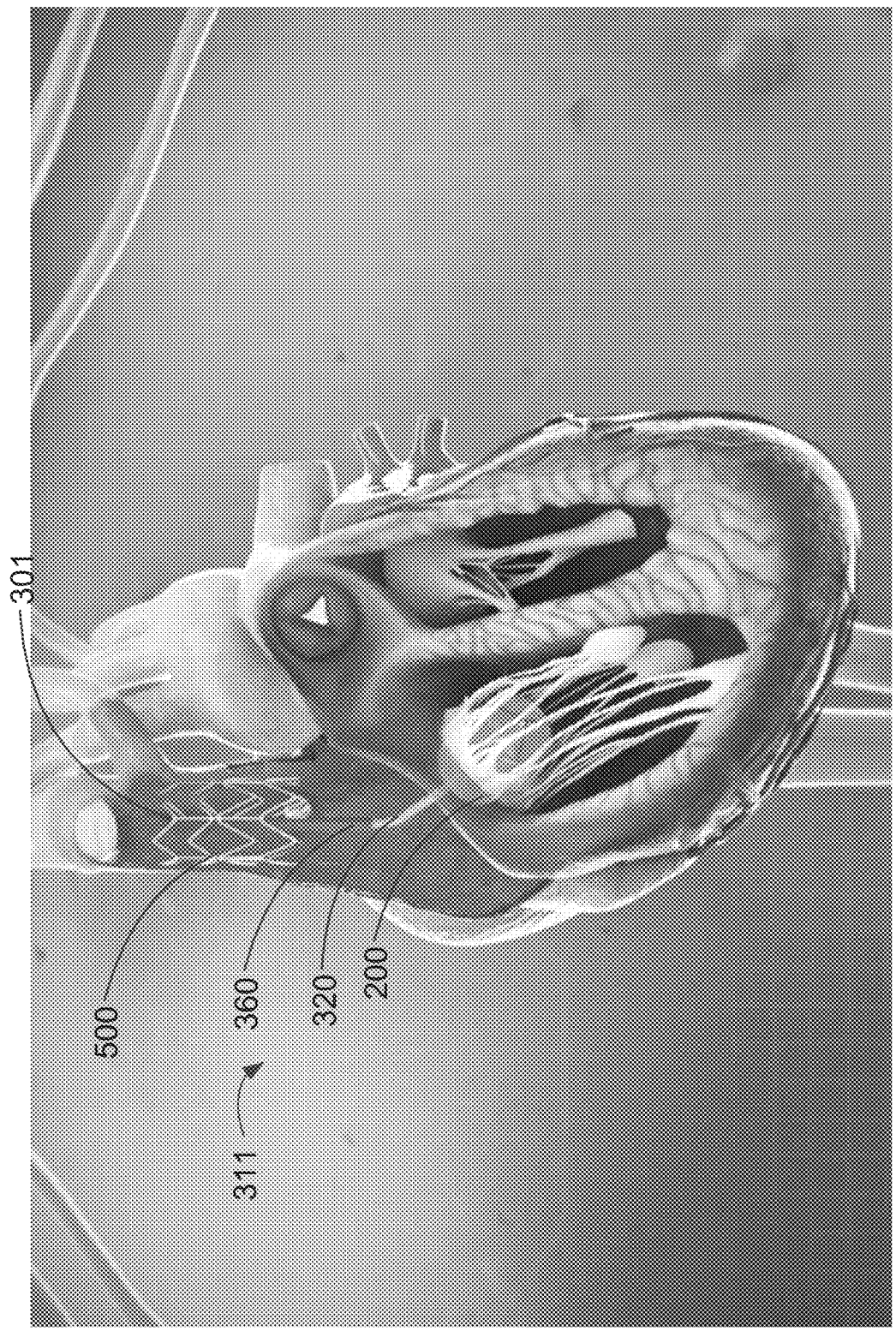
Figure 17I:
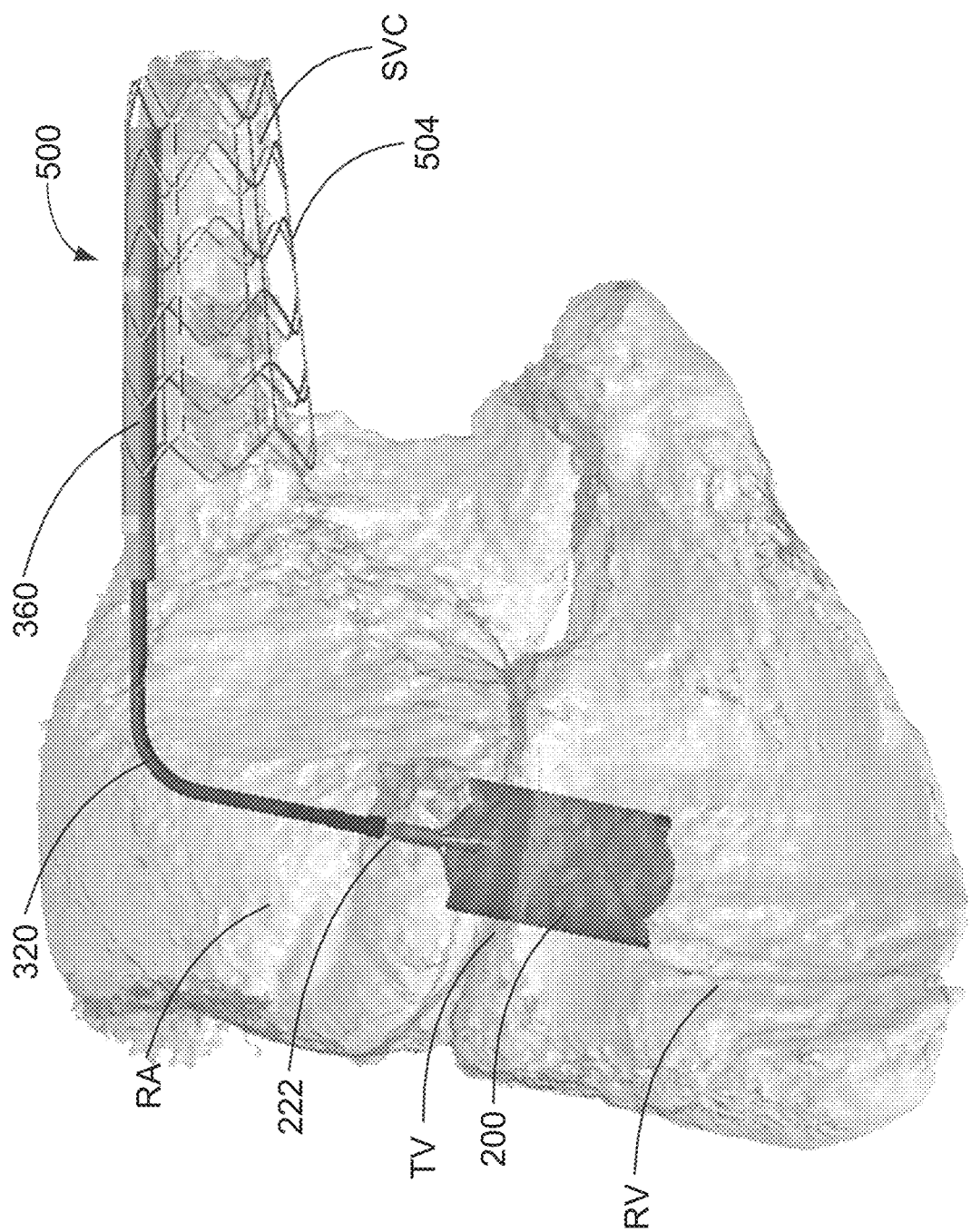
FIG. 17I illustrates the implantable portion of the heart valve therapeutic device of FIG. 1 maintained at a native heart valve via the support in accordance with the principles of the present invention.

Because anchor tube 360 is coupled to anchor 500, prosthetic coaptation body 200 will remain in place suspended across the native valve. As illustrated in FIG. 17H, distal, implantable portion 311 remains implanted while proximal, delivery portion 310, e.g., shaping catheter proximal portion, body support catheter proximal portion, 326, elongated rail proximal portion 304, and delivery sheath 402 and sheath introducer 400 are withdrawn, e.g., by pulling actuator 108 proximally. FIG. 17I illustrates the prosthetic coaptation body 200 in an implanted, deployed state for treating cardiac valve regurgitation. As shown, anchor 500 is implanted in the superior vena cava SVC while the support extends into the right atrium RA, bends a predefined angle (e.g., about 100 degrees) toward right ventricle RV, such that prosthetic coaptation body 200 is positioned across the tricuspid valve TV.

Figure 18:
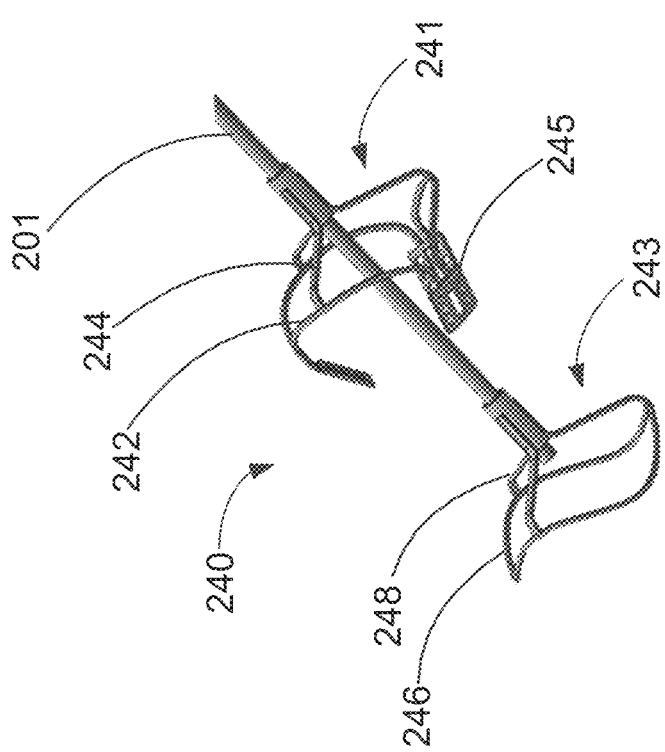
FIG. 18 is a perspective view of an alternative exemplary frame of the prosthetic coaptation body.

Referring now to FIG. 18, an alternative exemplary frame of the prosthetic coaptation body is described. Frame 240 is constructed similar to frame 205 of FIG. 2D. For example, frame 240 preferably includes spine 201, proximal portion 241 having proximal ring 242 coupled to slotted prosthetic leaflets anchors 245, and distal portion 243 having distal ring 246. Proximal ring 242 may be coupled to spine 201 via a plurality of proximal tethers 244 and an optional step, and distal ring 246 may be coupled to spine 201 via a plurality of distal tethers 248 and an optional step. Frame 240 differs from frame 205 in that frame 240 does not have an inner ring coupled to proximal ring 242. As shown in FIG. 18, the distal end of plurality of proximal tethers 244 may be coupled to proximal ring 242 at a midpoint of a segment of proximal ring 242 extending from one slotted prosthetic leaflets anchor 245 to an adjacent slotted prosthetic leaflets anchor, instead of at slotted prosthetic leaflets anchors 245. In addition, the distal end of plurality of distal tethers 248 may be coupled to distal ring 246 at a peak of the sinusoid of distal ring 246, instead of at the peak.

Figure 19:
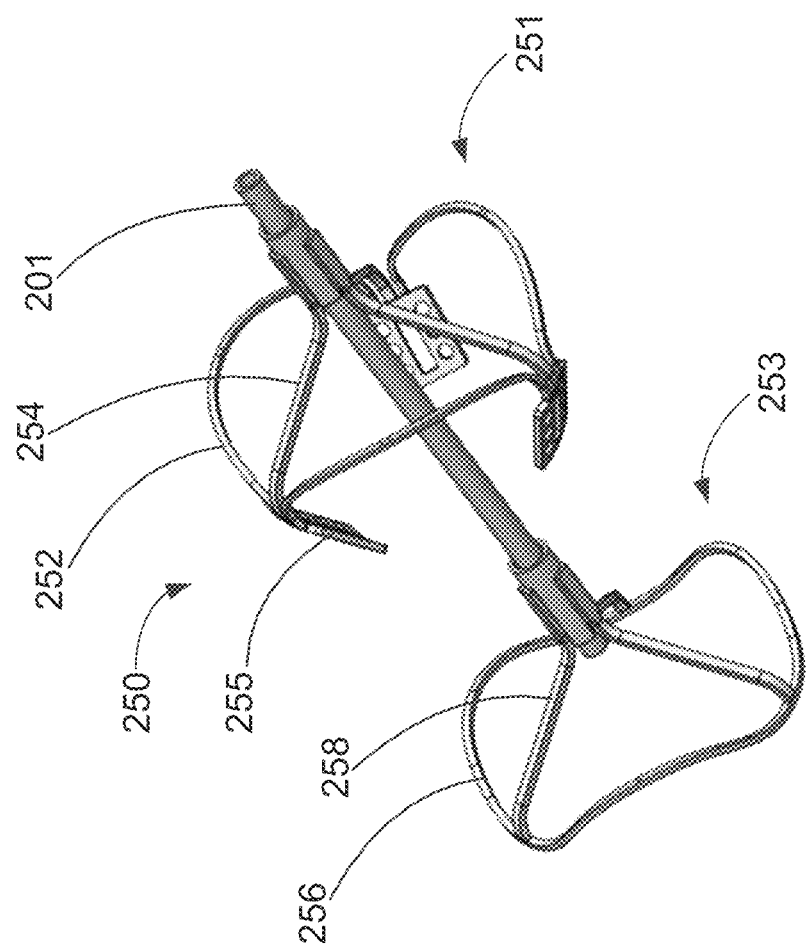
FIG. 19 is a perspective view of another alternative exemplary frame of the prosthetic coaptation body.

Referring now to FIG. 19, another alternative exemplary frame of the prosthetic coaptation body is described. Frame 250 is constructed similar to frame 205 of FIG. 2D. For example, frame 250 preferably includes spine 201, proximal portion 251 having proximal ring 252 coupled to slotted prosthetic leaflets anchors 255, and distal portion 253 having distal ring 256. Proximal ring 252 may be coupled to spine 201 via a plurality of proximal tethers 254 and an optional step, and distal ring 256 may be coupled to spine 201 via a plurality of distal tethers 258 and an optional step. Frame 250 differs from frame 205 in that frame 250 does not have an inner ring coupled to proximal ring 252.

Figure 20:
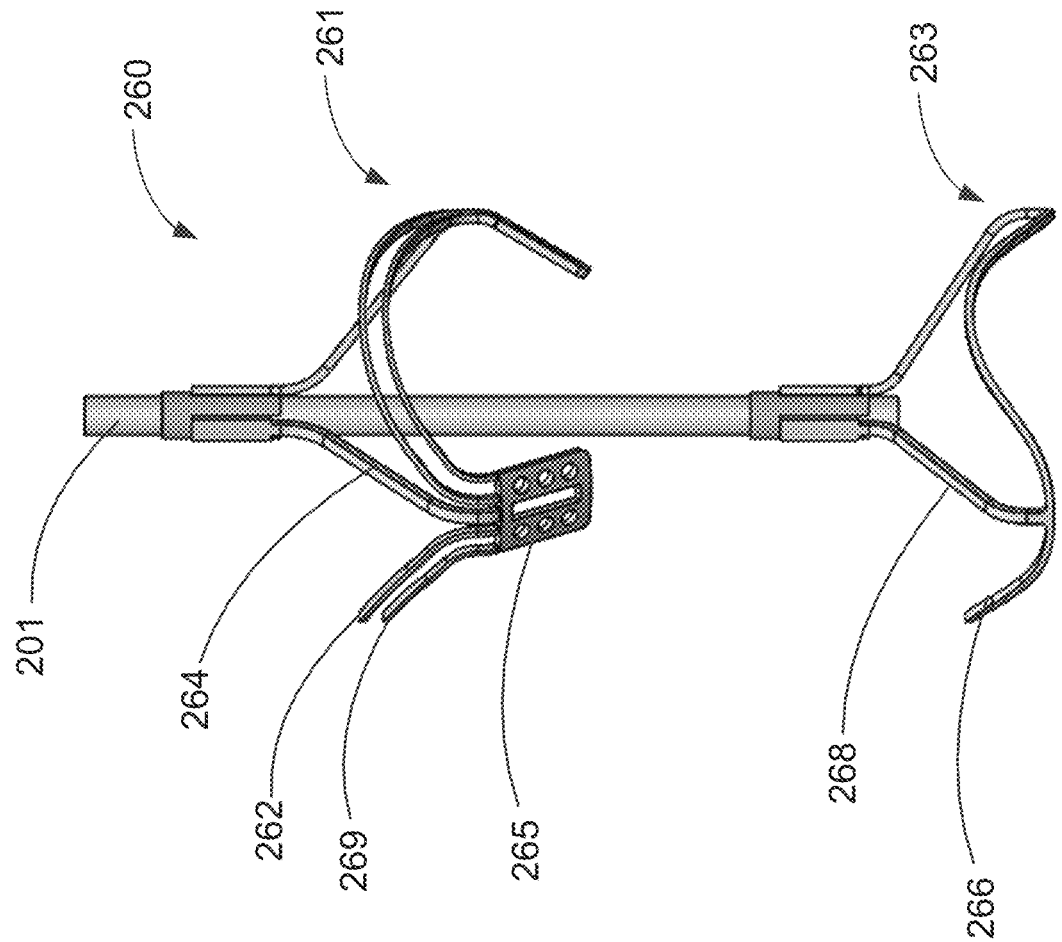
FIG. 20 is a perspective view of yet another alternative exemplary frame of the prosthetic coaptation body.

Referring now to FIG. 20, yet another alternative exemplary frame of the prosthetic coaptation body is described. Frame 260 is constructed similar to frame 205 of FIG. 2D. For example, frame 260 preferably includes spine 201, proximal portion 261 having proximal ring 262 coupled to slotted prosthetic leaflets anchors 265, and distal portion 263 having distal ring 266. Proximal ring 262 may be coupled to spine 201 via a plurality of proximal tethers 264 and an optional step, and distal ring 266 may be coupled to spine 201 via a plurality of distal tethers 268 and an optional step. Frame 260 differs from frame 205 in that frame 260 does not have an inner ring coupled to proximal ring 262. Instead, as shown in FIG. 20, frame 260 preferably includes second proximal ring 269 adjacent to proximal ring 262. Accordingly, the prosthetic leaflets may be sutured to proximal ring 262, while the skirt may be sutured to second proximal ring 269, or vice versa. In one embodiment, the prosthetic leaflets and the skirt may be joined together via an additional suture and/or an additional biocompatible material.

As will be understood by a person having ordinary skill in the art, a frame may be constructed with any combination of connections points and features of frame 205, frame 240, frame 250, or frame 260.

Moreover, the frame may be designed with predefined kink points to allow the conduit to be compressed into a delivery sheath without being damaged, and to more reliably expand upon delivery. The frame may have a proximal outer ring and distal outer ring, as well as an inner ring to which prosthetic valve leaflets may be attached. One or more of the rings may exhibit a sinusoidal or zig-zag shape in the expanded state to further improve the compression and expansion of the frame. The prosthetic coaptation body may have a proximal skirt joining a proximal inner ring and proximal outer ring, as well as an outer skirt joining the proximal outer ring to a distal outer ring to improve coaptation of the native valve against the outer skirt. The prosthetic coaptation body may be coupled to the support by a plurality of tethers that may be formed of shape-memory material such as Nitinol. The tethers may be rigid or stiff and hold the prosthetic coaptation body in position more accurately than tensile wires.

Figure 21B:
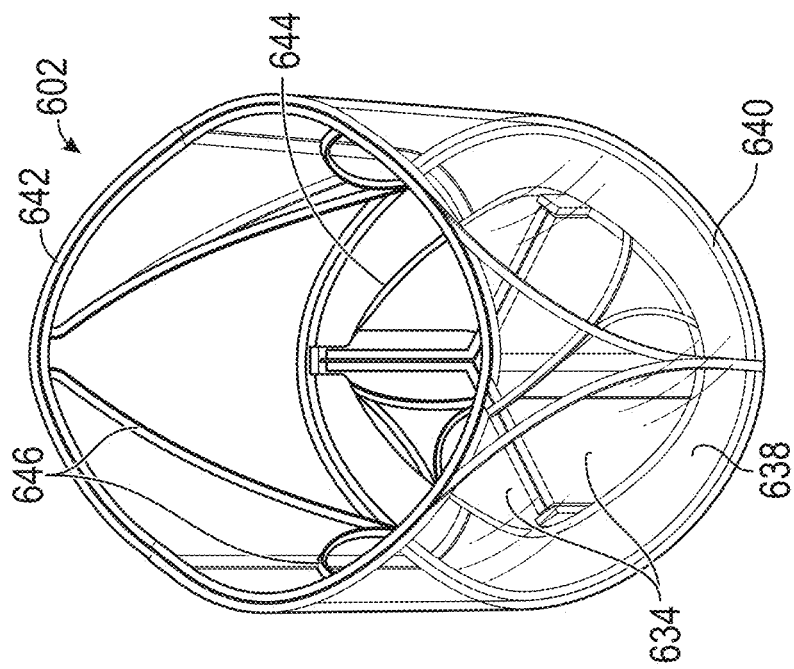
FIGS. 21A and 21B are perspective views of an alternative exemplary prosthetic coaptation body.
Figure 21A:
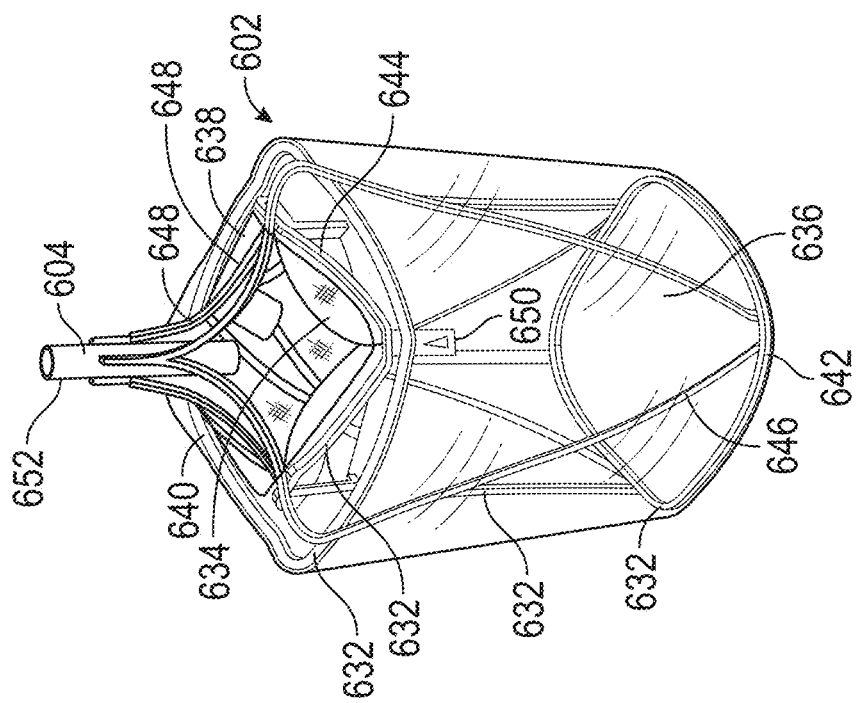

Referring now to FIGS. 21A and 21B, exemplary prosthetic coaptation body 602 of the heart valve therapeutic device is described. FIG. 21A shows prosthetic coaptation body 602 viewed from the proximal end downward, whereas FIG. 21B is a flipped over version of FIG. 21A. Prosthetic coaptation body 602 preferably includes frame 632 having prosthetic leaflets 634 coupled thereto, and may contain one or more biocompatible materials coupled to frame 632 such as outer skirt 636 and/or proximal skirt 638. The shape of prosthetic coaptation body 602 is formed by frame 632, which is designed to transition from a contracted, delivery state to an expanded, deployed state and may be formed from shape memory material such as Nitinol. For example, frame 632 may form a conduit that, together with prosthetic leaflets 634 and the biocompatible material covering form a channel to allow blood to travel through prosthetic leaflets 634, when opened during the cardiac cycle, and through prosthetic coaptation body 602. Outer skirt 636 is coupled to frame 632 and may radially extend around frame 632 to form an outer surface to which the native leaflets coapt when closed during the cardiac cycle.

Frame 632 preferably includes proximal outer ring 640, distal outer ring 642, and inner ring 644. In a preferred embodiment, inner ring 644 has a diameter less than that of proximal outer ring 640 and may also have a diameter less than that of distal outer ring 642. Frame may include longitudinal struts 646, tethers 648, slotted leaflet mounting features 650, and/or support tube 652. Proximal outer ring 640 and distal outer ring 642 may be coupled together by longitudinal struts 646. Longitudinal struts 646 may be angled towards one another around frame 632. For example, longitudinal struts 646 may form a plurality of triangle-like shapes extending radially around frame 632, as shown in FIG. 21A.

Inner ring 644 is preferably disposed (e.g., concentrically disposed) within proximal outer ring 644 and spaced apart from proximal outer ring 640 such that proximal outer ring 640 protects inner ring 644 from forces on frame 632 resulting from pressure changes during the cardiac cycle, thereby protecting the plurality of prosthetic leaflets 634. Proximal outer ring 640, distal outer ring 642, and inner ring 644 may have a generally-circular shape, but may be other shapes such as ovals or diamonds. As illustrated, inner ring 644 also preferably has a sinusoidal wave shape around its circumference. Proximal outer ring 640 and distal outer ring 642 may also be different sizes, forming prosthetic coaptation body 602 roughly into the shape of a truncated cone.

Frame 632 may be made of metal, such as Nitinol or stainless steel. Frame 632 may be made of various components including wires, tubes, or flat strips. In a preferred embodiment, frame 632 is laser cut from a single tube of Nitinol.

Frame 632 may be coupled to support 604 by tethers 648, which are preferably formed of a solid metal. Tethers 648 extend radially outward from support 604 to couple to inner ring 640. Tethers 648 are collapsible and/or compressible for delivery and may be self-expandable. Tethers 648 may also couple together proximal outer ring 640 and inner ring 644. Tethers 648 and longitudinal struts 646 may also be formed from the same member. Tethers 648 may be coupled to support tube 652, which may be formed as part of frame 632 or may be formed as part of elongated rail distal portion 302. If separately formed, support tube 652 is securely coupled to elongated rail distal portion 302 to form part of support 604.

Tethers 648 may extend from support tube 652 outwardly toward inner ring 644 such that tethers 648 are coupled to inner ring 644, further extending toward proximal outer ring 640 such that tethers 648 are coupled to proximal outer ring 640, thereby coupling inner ring 644 and proximal outer ring 640. In addition, tethers 648 may continue as longitudinal struts 646, and bend downward toward distal outer ring 642, thereby coupling proximal outer ring 640 and distal outer ring 642. Preferably, pairs of adjacent tethers 648 merge into a single member before reaching inner ring 644 or where they couple to inner ring 644. The merged tethers 648 couple together inner ring 644 and proximal outer ring 640 and then split into two longitudinal struts 646. The two longitudinal struts 646 may split diagonally from each other to form an upside-down V shape.

Additionally, frame 632 may have slotted leaflet mounting features 650 extending distally from inner ring 644. Prosthetic leaflets 634 may be coupled directly to inner ring 644 and may also be coupled at their edges to slotted leaflet mounting features 650. Coupling to slotted leaflet mounting features 650 may improve coaptation of prosthetic leaflets 634.

Outer skirt 636 may be a thin sheet of biocompatible material surrounding frame 632, extending from proximal outer ring 640 to distal outer ring 642 to form the outside surface of the conduit. Outer skirt 636 may be made of a rigid or compliant material. In some examples, outer skirt 636 expands and contracts responsive to pressure changes during the cardiac cycle. In this manner, outer skirt 636 may provide better coaptation with native leaflets. Preferably, outer skirt 636 is made of pericardium. Outer skirt 636 may be sewn to proximal outer ring 640 and distal outer ring 642. Proximal skirt 638 may be coupled to and cover the space between proximal outer ring 640 and inner ring 644. Proximal skirt 638 may be of rigid or compliant material. Preferably, proximal skirt 638 is made of pericardium. Proximal skirt 638 may be sewn to the proximal outer ring 640 and inner ring 644. In some embodiments, proximal skirt 638 and outer skirt 636 are formed from a single piece of material.

Prosthetic leaflets 634 are coupled to inner ring 644 and may also be coupled to slotted leaflet mounting features 650. Prosthetic leaflets 634 fill the space inside inner ring 644 to form a prosthetic valve which allows blood to flow in the distal direction, but prevents blood from flowing in the proximal direction. Though three prosthetic leaflets 634 are shown in FIGS. 21A and 21B, certain embodiments may have more or fewer prosthetic leaflets. Preferably, prosthetic leaflets 634 will match the number and arrangement of the native leaflets in the native valve.

Referring now to FIGS. 22A through 22E exemplary frame 632 of prosthetic coaptation body 602 is illustrated. As shown in FIG. 22A, frame 632 may have a number of predefined kink points 654 to allow frame 632 to reliably compress into the delivery sheath for insertion into the blood vessel and to expand upon delivery into the heart. This reduces the likelihood that frame 632 or prosthetic leaflets 634 will be damaged when they are pulled into the delivery sheath or that frame 632 will not fully expand upon delivery. One or more of proximal outer ring 640, distal outer ring 642, or inner ring 644 may be sinusoidal in shape to further aid compression and expansion of frame 632. Preferably, proximal outer ring 640 and inner ring 644 may be sinusoidal. As shown in FIG. 22A, the amplitude of the sinusoidal shape may be greater in inner ring 644 than proximal outer ring 640 and/or distal outer ring 642. Tethers 648 and longitudinal struts 646 preferably couple to proximal outer ring 640 and inner ring 644 at the crest of the sinusoid. FIG. 22E shows a laser-cut, flat pattern of the exemplary frame.

FIGS. 23A, 23B, and 23C are perspective views of another exemplary frame of a prosthetic coaptation body for the heart valve therapeutic device that are well-suited for an acute treatment and FIGS. 23D and 23E show exemplary laser-cut, flat pattern of the exemplary frame. A plurality of prosthetic leaflets may be coupled to the frame for the acute treatment.

FIGS. 23F and 23G show illustrative photos of the reflown polymer coatings over the Nitinol frame components and the stainless steel positioning tubes. Holes (e.g., oval-shaped holes) in the frame elements are configured to be able to allow the frame to be connected to the support via reflown polymer.

Figure 24A:
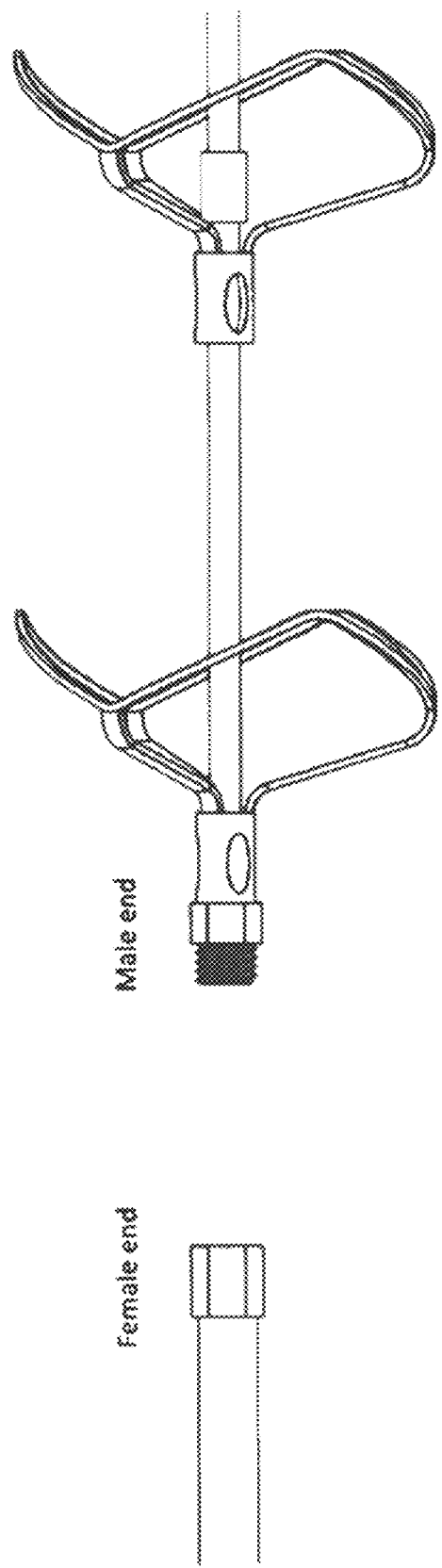
FIG. 24A illustrates an exemplary threaded system for coupling the device to the detachable support.

FIG. 24A illustrates an exemplary system for removably coupling the prosthetic coaptation body to the support, for example, at the catheter. By permitting separation of the prosthetic coaptation body and the catheter/support, the two components may be packaged separately. For example, the prosthetic coaptation body may be packaged in a liquid sterilant and the catheter may be packaged dry. The coupling may occur ex vivo prior to implantation. The prosthetic coaptation body may be removably coupled to the support (e.g., at the catheter) using a threaded mechanism. For example, a threaded screw at the male end may be screwed into the female end.

As shown in FIG. 24A, the frame assembly may have a distal and proximal frame component fastened to the central spine. The frame assembly also shows multiple layers of polymer interface elements. These polymer layers may be melted and fused together locking the Nitinol frame tube to the other components without having the Nitinol touch other metals, and thus avoiding the corrosion issues between dissimilar metals. The frame assembly also may include safety collars that are securely crimped to provide additional resistance to pull out of the polymer bonded Nitinol frame components during device retrieval and collapse into a retrieval sheath, where the polymer components may fail in shear or delamination. The frame sub-assembly could then be fastened to the spine with crimping or adhesive or another suitable method. Additionally, the frame could be bonded directly to the spine using the same polymer reflowing method.

Figure 24D:
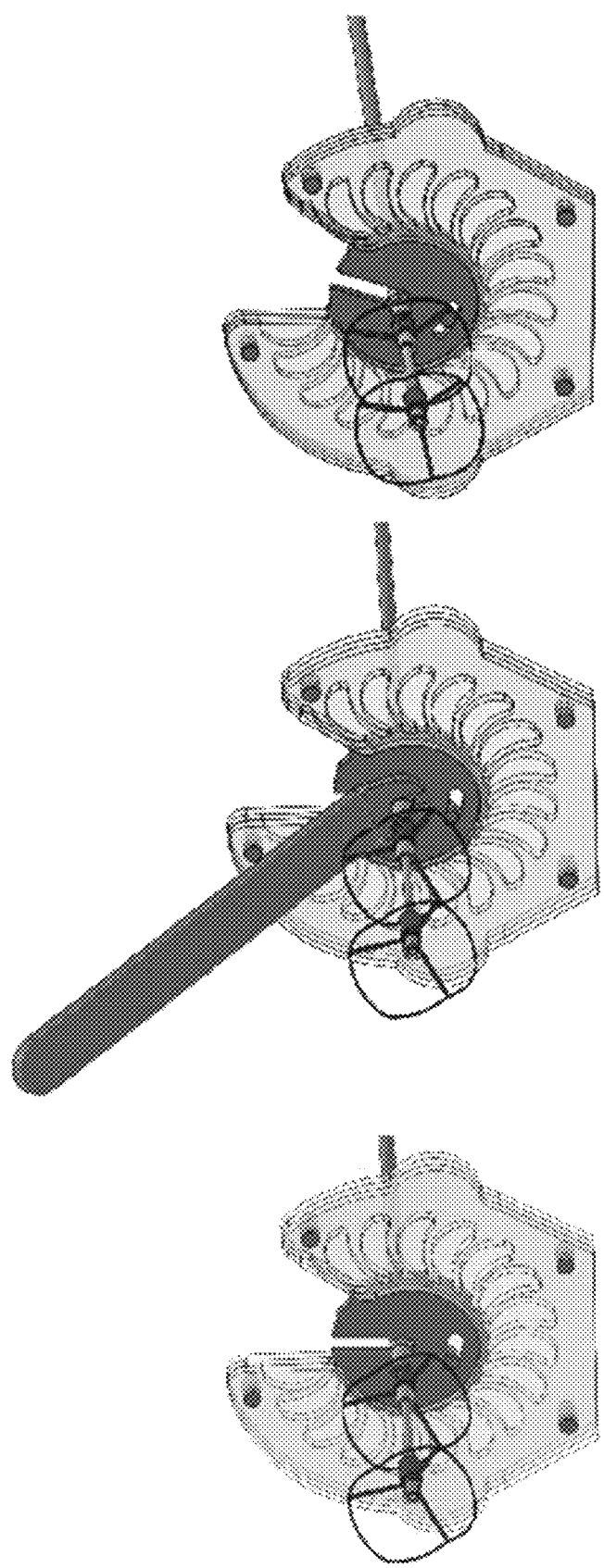

FIG. 24B illustrates a torque limiting system that may be used to limit torqueing during coupling. As illustrated, two torque limiting components may be used. An outer ring is coupled to an inner ring via flexible vanes or struts. The inner ring is placed against the distal end of the body support catheter and twisted by hand via the outer ring. Once the two components are coupled together and the threads tight, the torque that is applied by the outer ring is exceeded by the resistance of the tightened threads, the struts deflect and slip past the inner features within the outer ring. This limits the torque that can be applied to the threaded coupler via the outer ring. The length, shape, thickness and stiffness of flexible struts (FIG. 24C) may thus be calibrated to provide the desired torque limiting characteristics. The torque limiting components may be made from plastic. Once the suitable torque has been reached, the two nested plastic pieces slip within each other and click into place. FIG. 24D illustrates the steps of using the torque limiting system to limit torqueing during coupling of the prosthetic coaptation body to the body support catheter.

Figure 25A:
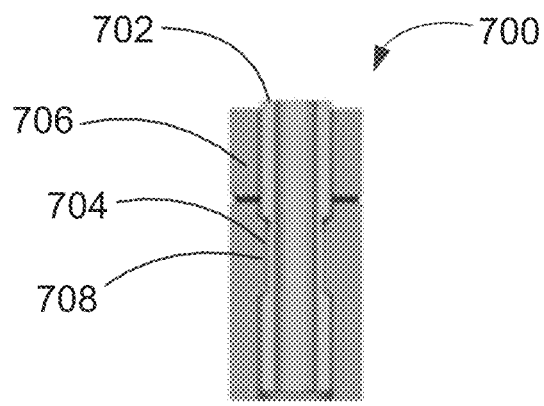
FIGS. 25A and 25B illustrate an alternative exemplary snap fit system for coupling the prosthetic device to the detachable support.
Figure 25B:
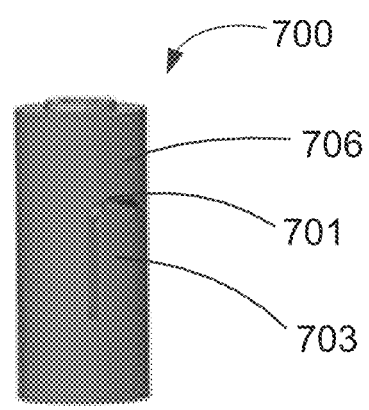

Referring now to FIGS. 25A and 25B, alternative exemplary snap fit system 700 for coupling the prosthetic coaptation body to the detachable support is described. As shown in FIG. 25A, spine connector 702, which may be coupled to the spine of the prosthetic coaptation body, may have a tubular shape with one or more grooves 704 disposed on its outer surface along its mid-portion. Support connector 706, which may be coupled to the body support catheter, may have an internal lumen having one or more protrusions 708 disposed therein. Protrusions 708 have a geometry corresponding to grooves 704 of spine connector 702. Protrusions 708 may be disposed on flexible portion 703 of support connector 706 defined by U-shaped slit 701, as shown in FIG. 25B. Accordingly, as the proximal end of spine connector 702 is inserted within the lumen of support connector 706, the proximal end of spine connector 702 pushes against protrusions 708 such that flexible portion moves radially outward until protrusions 708 are aligned with grooves 704, and flexible portion 703 returns to its natural state, thereby locking spine connector 702 to support connector 706. Grooves 704 may include a number of grooves corresponding with the number of protrusions 708, or alternatively, groove 704 may be a single groove extending circumferentially around the mid-portion of spine connector 702. In addition, the distal end of the elongated rail may be positioned within the inner diameter of spine connector 702 to prevent detachment of spine connector 702 from support connector 706.

Figure 26A:
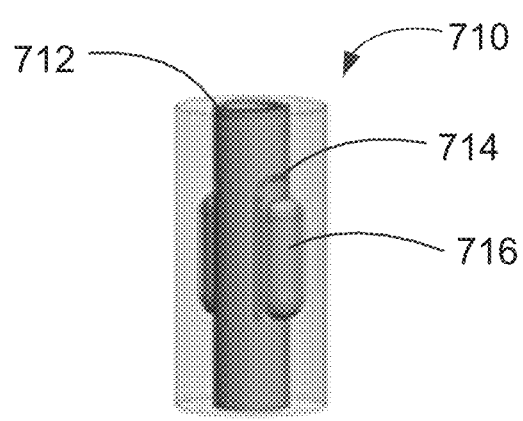
FIGS. 26A and 26B illustrate another alternative exemplary snap fit system for coupling the prosthetic device to the detachable support.
Figure 26B:
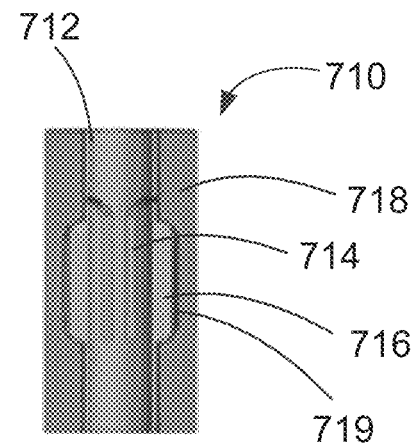

Referring now to FIGS. 26A and 26B, alternative exemplary snap fit system 710 for coupling the prosthetic coaptation body to the detachable support is described. As shown in FIG. 26A, spine connector 712, which may be coupled to the spine of the prosthetic coaptation body, may have a tubular shape with a lumen extending therethrough. Spine connector 712 may have one or more protrusions 716 disposed on its outer surface on a flexible portion defined by U-shaped slit 714. Support connector 718, which may be coupled to the body support catheter, may have a tubular shape having a lumen with one or more grooves 719 along its mid-portion. Protrusions 716 have a geometry corresponding to grooves 719 of support connector 718. Accordingly, as the proximal end of spine connector 712 is inserted within the lumen of support connector 718, the internal lumen of support connector 718 pushes against protrusions 716 such that the flexible portion moves radially inward into the lumen of spine connector 712 until protrusions 716 are aligned with grooves 719, and the flexible portion of spine connector 712 returns to its natural state, thereby locking spine connector 712 to support connector 718. Grooves 719 may include a number of grooves corresponding with the number of protrusions 716, or alternatively, groove 719 may be a single groove extending circumferentially around the mid-portion of support connector 718. In addition, the distal end of the elongated rail may be positioned within the inner diameter of spine connector 712 to prevent detachment of spine connector 712 from support connector 718.

Figure 27A:
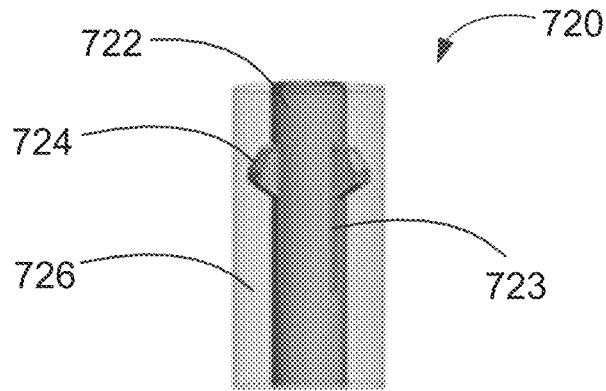
FIGS. 27A and 27B illustrate yet another alternative exemplary snap fit system for coupling the prosthetic device to the detachable support.
Figure 27B:
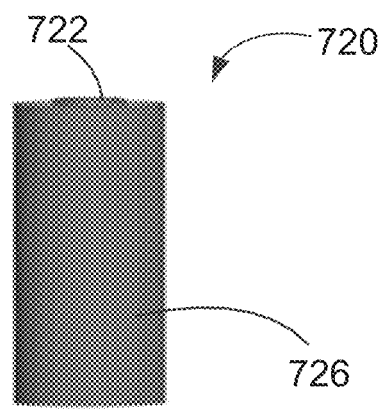

Referring now to FIGS. 27A and 27B, alternative exemplary snap fit system 720 for coupling the prosthetic coaptation body to the detachable support is described. As shown in FIG. 27A, spine connector 722, which may be coupled to the spine of the prosthetic coaptation body, may have a tubular shape with a lumen extending therethrough. Spine connector 722 may have one or more protrusions 724 disposed on its outer surface on a flexible portion defined by U-shaped slit 723. Support connector 726, which may be coupled to the body support catheter, may have a tubular shape having a lumen with one or more grooves along its mid-portion. Protrusions 724 have a geometry corresponding to the one or more grooves of support connector 726. Accordingly, as the proximal end of spine connector 722 is inserted within the lumen of support connector 726, the internal lumen of support connector 726 pushes against protrusions 724 such that the flexible portion moves radially inward into the lumen of spine connector 722 until protrusions 724 are aligned with the one or more grooves of support connector 726, and the flexible portion of spine connector 722 returns to its natural state, thereby locking spine connector 722 to support connector 726. The one or more grooves may include a number of grooves corresponding with the number of protrusions 724, or alternatively, may be a single groove extending circumferentially around the mid-portion of support connector 726.

Figure 28A:
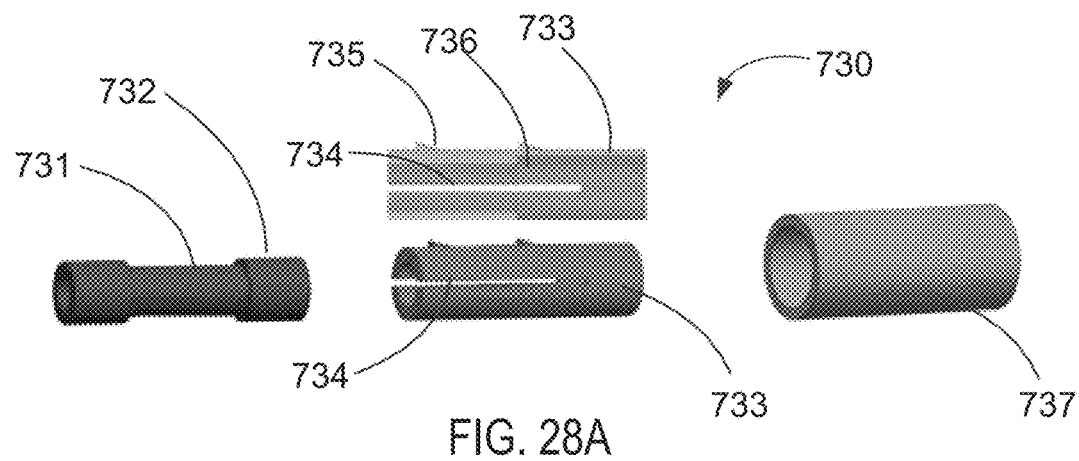
FIGS. 28A and 28B illustrate an exemplary hybrid snap and interlinking connector system for coupling the prosthetic device to the detachable support.
Figure 28B:
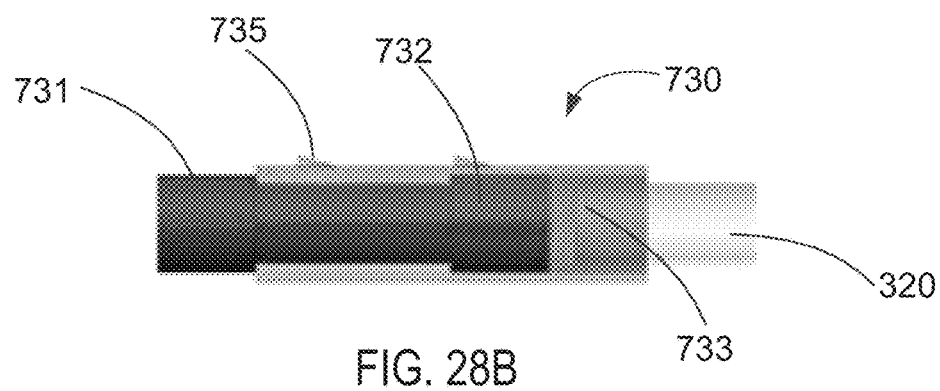

Referring now to FIGS. 28A and 28B, exemplary hybrid snap and interlinking connector system 730 for coupling the prosthetic coaptation body to the detachable support is described. Spine connector 731, which may be coupled to the spine of the prosthetic coaptation body, may have proximal portion 732 having an outer diameter that is larger than an outer diameter of a mid-portion of spine connector 731. In addition, spine connector 731 may have a distal portion having an outer diameter that is larger than an outer diameter of a mid-portion of spine connector 731. Support connector 733, which may be coupled to body support catheter distal portion 320 of the support, may have a tubular shape having a cavity therein. The distal portion of the cavity may have a diameter equal to the outer diameter of the mid-portion of spine connector 731, and proximal portion 736 of the cavity may have a diameter equal to the outer diameter of proximal portion 732 of spine connector 731. Support connector 733 may have one or more slits 734 for providing relief to support connector 733 as spine connector 731 is inserted within the cavity of support connector 733. In addition, support connector 733 may have a plurality of ridges 735 disposed along its outer surface. Accordingly, as spine connector 731 is inserted into the cavity of support connector 733, the distal portion of support connector 733 will expand radially outward via slits 734 until proximal portion 732 of spine connector 731 is aligned with proximal portion 736 of the cavity of support connector 733, and the distal portion of support connector 733 returns to its natural state, thereby locking spine connector 731 to support connector 733. Hybrid snap and interlinking connector system 730 further may include compression sleeve 737, which may be slidably disposed over support connector 733. When compression sleeve 737 is disposed over support connector 733, plurality of ridges 735 engage with the inner surface of compression sleeve 737 to further lock compression sleeve 737 with support connector 733.

Figure 29:
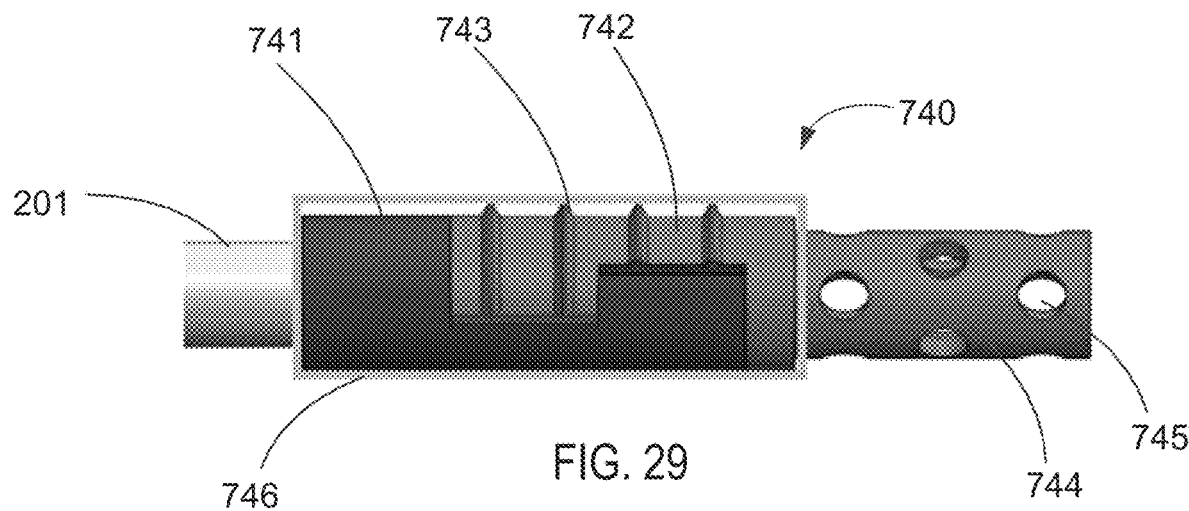
FIG. 29 illustrates another alternative exemplary snap fit system for coupling the prosthetic device to the detachable support.

Referring now to FIG. 29, another exemplary hybrid snap and interlinking connector system 740 for coupling the prosthetic coaptation body to the detachable support is described. System 740 is constructed similar to interlinking connector system 230 of FIGS. 15A and 15B. For example, system 740 includes spine connector 741, support connector 742, and sleeve which may be a compression sleeve or other mean to keep interlinking element together 746. In addition, support connector 742 may have proximal portion 744 having a plurality of openings 745 for facilitating coupling of support connector 742 to the body support catheter, as described with regard to the interlinking connector system of FIG. 16A. System 740 differs from system 230 in that support connector 742 may have a plurality of ridges 743 disposed along its outer surface. The ridges may have a directional bias, like a barb, to allow movement of sleeve 746 in one direction, while inhibiting movement of sleeve 746 in the other direction. Accordingly, when spine connector 741 is engaged with support connector 742, and compression sleeve 746 is disposed over spine connector 741 and support connector 742, plurality of ridges 743 engage with the inner surface of compression sleeve 746 to further lock compression sleeve 746 with spine connector 741 and support connector 742.

Figure 30:
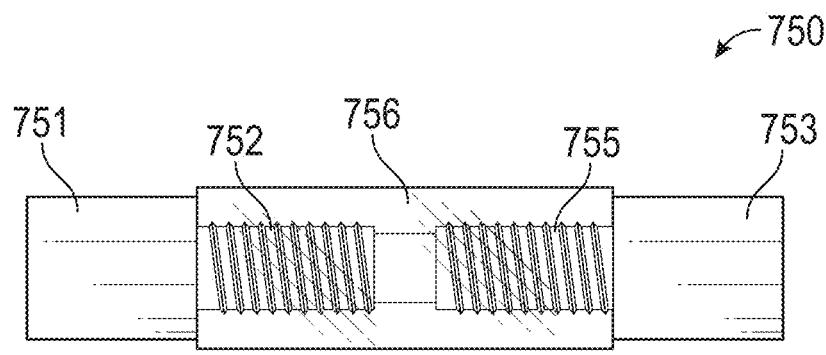
FIG. 30 illustrates an exemplary threaded system for coupling the prosthetic device to the detachable support.

Referring now to FIG. 30, an exemplary threaded system for coupling the prosthetic coaptation body to the detachable support is described. Threaded system 750 includes spine connector 751 having first threaded portion 752, support connector 753 having second threaded portion 755, and compression sleeve 765 having a third threaded portion for engaging with first threaded portion 752 and second threaded portion 755. As shown in FIG. 30, spine connector 751 may be coupled to support connector 753 via first threaded portion 752, second threaded portion 755, and compression sleeve 756.

Figure 31A:
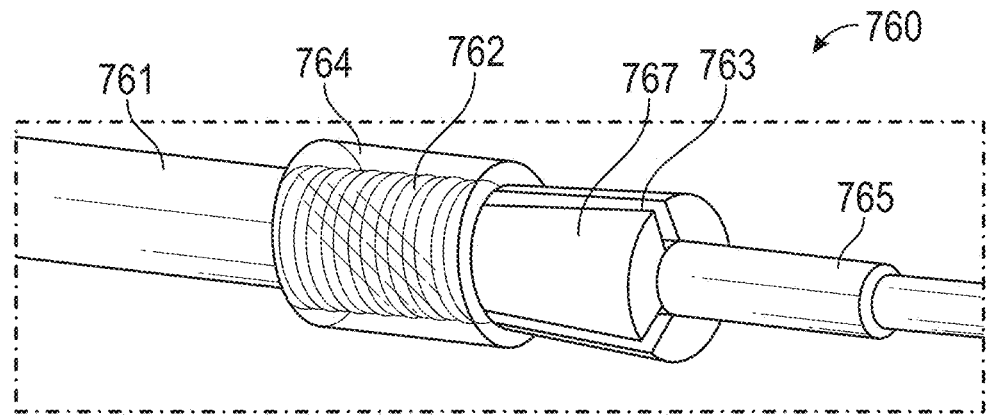
FIGS. 31A and 31B illustrate another exemplary threaded system for coupling the prosthetic device to the detachable support.
Figure 31B:
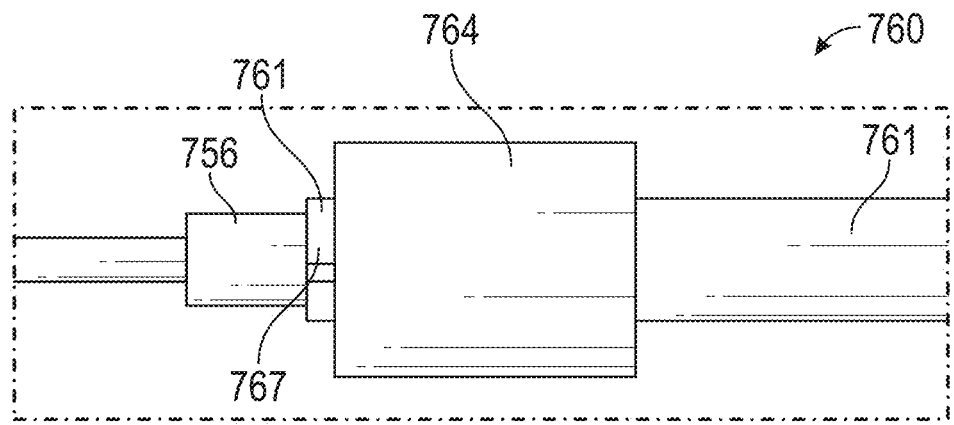

Referring now to FIGS. 31A and 31B, another exemplary threaded system for coupling the prosthetic coaptation body to the detachable support is described. As shown in FIG. 31A, spine connector 765, which may be coupled to the spine of the prosthetic coaptation body, may have a tubular shape. Support connector 761, which may be coupled to the body support catheter, may have threaded portion 762 and one or more prongs 767 defined by one or more slits 763 distal to threaded portion 762. Slits 763 provide relief to prongs 767 as spine connector 765 is inserted into the lumen of support connector 761. When spine connector 765 is inserted into the lumen of support connector 761, threaded compression sleeve 764 may be advanced distally, e.g., via rotation of threaded compression sleeve 764, over threaded portion 762 and prongs 767, thereby causing prongs 767 to move radially inward and push against spine connector 765 to lock spine connector 765 to support connector 761.

Figure 32:
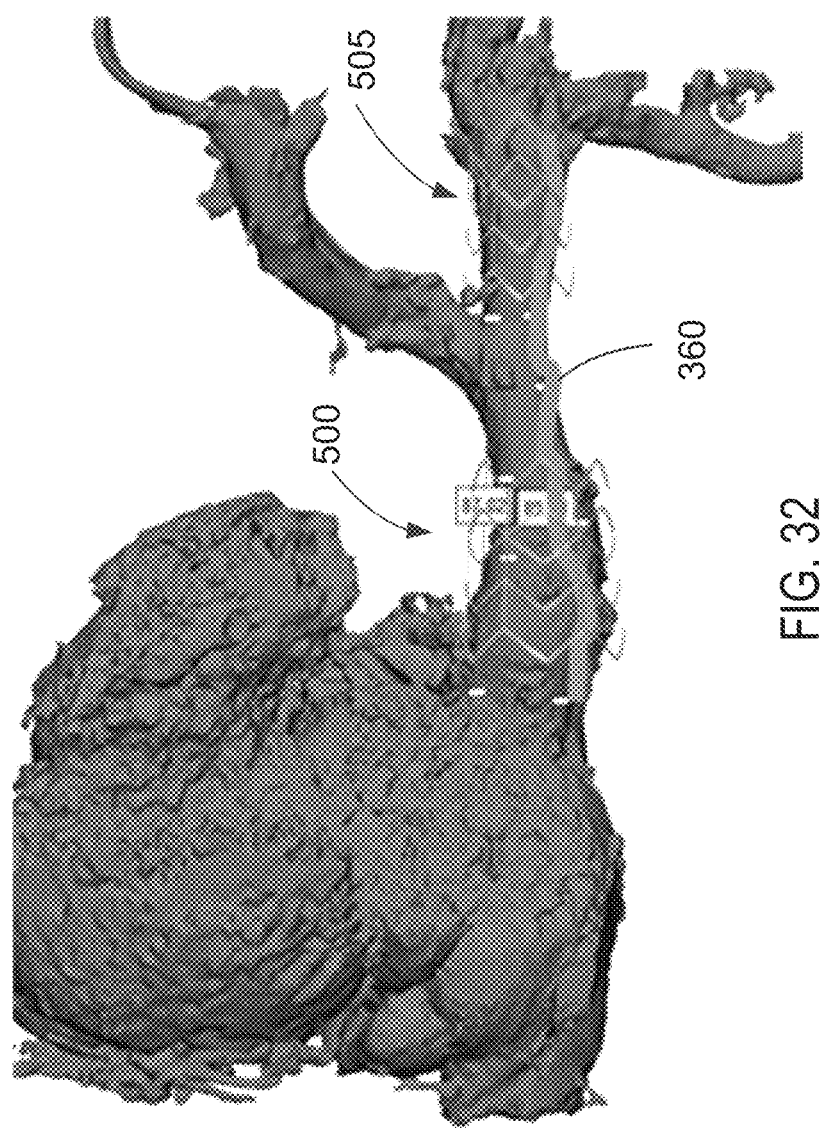
FIG. 32 illustrates select implantable components of an alternative exemplary heart valve therapeutic device having two anchors.

Referring now to FIG. 32, an alternative exemplary heart valve therapeutic device having two anchors is described. As shown in FIG. 32, anchor tube 360 may be coupled to anchor 500 for implantation at a first location within the patient's vasculature to support and maintain the prosthetic coaptation body (not shown) within the native heart valve. In addition, anchor tube 360 may be coupled to a second anchor 505, constructed similar to anchor 500, at a second location proximal to the first location within the patient's vasculature to provide additional support in maintaining anchor 500 at the first location and the prosthetic coaptation body within the native heart valve. Anchor 500 and second anchor 505 may have similar or different stiffness, and may exhibit the same or different radial force for anchoring in their respective locations. The anchor tube may also be shaped set so as to bias it away from the vessel wall to reduce the risk of trauma.

The invention is not limited to the embodiments described but may be varied in construction and detail. For example, the order in which the elongated rail, the body support catheter, and the shaping catheter are disposed within each other to form the support may vary. The described embodiments are to be considered in all respects only as illustrative and not restrictive. Any part of the device may be of a material that is visible to equipment such as echo or x-ray imaging equipment. The device may further comprise a controller arranged to be implanted subcutaneously on the support to allow the position of the prosthetic coaptation body to be changed after insertion. Electromagnetic switches may be used to activate to alter the position of the distal end of the support.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A system for implanting a therapeutic heart valve device at a native heart valve of a patient's heart, the system comprising:
a prosthetic device configured to be implanted at the native heart valve;
a support coupled to the prosthetic device and configured to maintain the prosthetic device at the native heart valve, the support comprising an elongated rail disposed within a first catheter disposed within a second catheter, each of the elongated rail, the first catheter, and the second catheter comprising a distal, implantable portion detachably engaged with a proximal, delivery portion configured to extend from the distal, implantable portion to outside the patient's body when the support is in a delivery state; and
an actuator coupled to the support, the actuator configured to cause the proximal, delivery portion to detach from the distal, implantable portion at a detachment area of the support while within the patient responsive to actuation such that the distal, implantable portion and the prosthetic device are configured to remain implanted within the patient's body.

2. The system of claim 1, wherein the distal, implantable portion of the elongated rail is configured to be attached to the proximal, delivery portion of the elongated rail during delivery and detached at the detachment area by the actuator for implantation of the distal, implantable portion of the elongated rail.

3. The system of claim 2, wherein the first catheter comprises a body support catheter, and wherein the distal, implantable portion of the body support catheter is configured to be attached to the proximal, delivery portion of the body support catheter during delivery and detached at the detachment area by the actuator for implantation of the distal, implantable portion of the body support catheter.

4. The system of claim 1, wherein the support comprises a lock at the distal, implantable portion, and wherein the actuator is configured to activate the lock to lock the distal, implantable portion in an implantable configuration within the patient responsive to actuation.

5. The system of claim 4, wherein the support is adjustable prior to locking and the lock is configured to move from a first delivery position to a second locked position to lock in the implantable configuration.

6. The system of claim 4, further comprising a second lock configured to lock the distal, implantable portion to an anchor system within the patient responsive to actuation at the actuator.

7. The system of claim 1, wherein the proximal, delivery portion is configured to interlink with the distal, implantable portion at the detachment area during delivery and to detach responsive to actuation at the actuator.

8. The system of claim 1, wherein the support comprises a connection configured to transition between a collapsed configuration where the connection engages with the distal, implantable portion and an expanded configuration where the connection disengages from the distal, implantable portion.

9. The system of claim 8, wherein a pusher is configured to be retracted proximally to expose the connection such that the connection transitions from the collapsed configuration to the expanded configuration.

10. The system of claim 3, wherein the second catheter comprises a shaping catheter, and wherein, when in a locked position, the distal, implantable portion of the body support catheter locks to the distal, implantable portion of the elongated rail and to the distal, implantable portion of the shaping catheter in the implantable configuration.

11. The system of claim 10, wherein the distal, implantable portion of the shaping catheter is configured to be attached to the proximal, delivery portion of the shaping catheter during delivery and detached at the detachment area by the actuator for implantation of the distal, implantable portion of the shaping catheter.

12. The system of claim 1, wherein the support comprises an anchor configured to anchor the support within the patient.

13. The system of claim 12, wherein the anchor is configured to anchor the support to a blood vessel coupled to the heart.

14. The system of claim 12, wherein the anchor comprises a stent.

15. The system of claim 14, wherein the stent is tapered.

16. The system of claim 12, wherein the anchor is disposed adjacent to the detachment area.

17. The system of claim 12, wherein the support comprises an anchor tube coupled to the distal, implantable portion of the support, and wherein the anchor is coupled to the anchor tube.

18. The system of claim 17, wherein the detachment area is within the anchor tube.

19. The system of claim 17, wherein a distal, implantable portion of the anchor tube is configured to be attached to a proximal, delivery portion during delivery and detached at the detachment area by the actuator for implantation of the distal, implantable portion of the anchor tube.

20. The system of claim 1,
wherein the distal, implantable portions of each of the elongated rail, the first catheter, and the second catheter are configured to lock together within the patient responsive to actuation.

21. The system of claim 1, wherein the prosthetic device comprises a frame forming a conduit, an outer skirt, and a plurality of prosthetic leaflets, the frame comprising a proximal ring and a distal ring.

22. The system of claim 21, wherein the proximal ring is coupled to a plurality of prosthetic leaflets anchors, the plurality of prosthetic leaflets anchors comprising a plurality of suture eyelets configured to permit suturing of the plurality of prosthetic leaflets to the frame.

23. The system of claim 21, wherein the prosthetic device comprises a spine configured to be coupled to the support.

24. The system of claim 23, wherein the proximal ring is coupled to the spine via a plurality of proximal tethers, and the distal ring is coupled to the spine via a plurality of distal tethers.

25. The system of claim 23, wherein the spine comprises a spine connector having a first geometry, and
wherein a distal end of the support comprises a support connector having a second geometry configured to engage with the first geometry of the spine connector.

26. The system of claim 25, wherein the support further comprises a sleeve configured to be disposed over the support connector and the spine connector when the support connector is engaged with the spine connector.

27. The system of claim 1, wherein the prosthetic device is a prosthetic valve with a plurality of prosthetic leaflets configured to open and close during the cardiac cycle.

28. A delivery system for implanting a therapeutic heart valve device at a native heart valve of a patient's heart, the delivery system comprising:
- a proximal elongated shaft configured to be detachably coupled, in a delivery state, to a distal elongated shaft configured to be coupled to a prosthetic device, the proximal elongated shaft and the distal elongated shaft having a length, when coupled, to percutaneously deliver the prosthetic device to the native heart valve for implantation, the proximal elongated shaft and the distal elongated shaft comprising an elongated rail disposed within a first catheter disposed within a second catheter, each of the elongated rail, the first catheter, and the second catheter comprising a distal, implantable portion detachably engaged with a proximal, delivery portion configured to extend from the distal, implantable portion to outside the patient's body when in the delivery state; and
- an actuator coupled to the proximal elongated shaft, the actuator configured to cause the proximal elongated shaft to detach from the distal elongated shaft at a detachment area of a support comprising the proximal elongated shaft and the distal elongated shaft while within the patient responsive to actuation to implant the prosthetic device and the distal elongated shaft within the patient in the deployed state.

29. The delivery system of claim 28, wherein the first catheter comprises a body support catheter and the second catheter comprises a shaping catheter each configured to attach to a corresponding component in the distal elongated shaft during delivery and to detach for implantation.

30. A method for implanting a therapeutic heart valve device at a native heart valve of a patient's heart, the method comprising:
- advancing a prosthetic device to the native heart valve, the prosthetic device coupled to a support comprising an elongated rail disposed within a first catheter disposed within a second catheter, each of the elongated rail, the first catheter, and the second catheter comprising a distal, implantable portion and a proximal, delivery portion configured to extend from the distal, implantable portion to outside the patient's body when the support is in a delivery state;
- anchoring the distal, implantable portion of the support within the patient to maintain the prosthetic device at the native heart valve; and
- actuating an actuator coupled to the support to cause the proximal, delivery portion to detach from the distal, implantable portion at a detachment area of the support while within the patient responsive to actuation such that the distal, implantable portion and the prosthetic device remain implanted within the patient's body.

* * * * *